(12) United States Patent
Weiner et al.

(10) Patent No.: US 10,934,549 B2
(45) Date of Patent: Mar. 2, 2021

(54) NUCLEIC ACID APTAMERS

(71) Applicant: UNIVERSITY OF IOWA RESEARCH FOUNDATION, Iowa City, IA (US)

(72) Inventors: George Weiner, Iowa City, IA (US); William Thiel, Iowa City, IA (US); Paloma Giangrande, Iowa City, IA (US); Suresh Veeramani, Iowa City, IA (US); Sue Blackwell, Iowa City, IA (US)

(73) Assignee: UNIVERSITY OF IOWA RESEARCH FOUNDATION, Iowa City, IA (US)

(*) Notice: Subject to any disclaimer, the term of this patent is extended or adjusted under 35 U.S.C. 154(b) by 124 days.

(21) Appl. No.: 16/104,970

(22) Filed: Aug. 20, 2018

(65) Prior Publication Data
US 2019/0136240 A1    May 9, 2019

Related U.S. Application Data

(60) Provisional application No. 62/547,357, filed on Aug. 18, 2017.

(51) Int. Cl.
| | | |
|---|---|---|
| *C12N 15/115* | (2010.01) | |
| *C07K 14/55* | (2006.01) | |
| *A61P 35/00* | (2006.01) | |
| *A61K 47/64* | (2017.01) | |
| *A61K 47/54* | (2017.01) | |
| *C07K 14/705* | (2006.01) | |
| *C07K 14/715* | (2006.01) | |

(52) U.S. Cl.
CPC .......... *C12N 15/115* (2013.01); *A61K 47/549* (2017.08); *A61K 47/642* (2017.08); *A61P 35/00* (2018.01); *C07K 14/55* (2013.01); *C07K 14/70532* (2013.01); *C07K 14/7155* (2013.01); *C12N 2310/16* (2013.01); *C12N 2320/13* (2013.01)

(58) Field of Classification Search
None
See application file for complete search history.

(56) References Cited

U.S. PATENT DOCUMENTS

| | | | |
|---|---|---|---|
| 5,270,163 A | 12/1993 | Gold et al. | |
| 5,475,096 A | 12/1995 | Gold et al. | |
| 5,589,332 A | 12/1996 | Shih et al. | |
| 5,741,679 A | 4/1998 | George et al. | |
| 6,261,783 B1 | 7/2001 | Jayasena et al. | |
| 2003/0175703 A1 | 9/2003 | Sullenger et al. | |
| 2005/0239134 A1* | 10/2005 | Gorenstein .......... | C12N 15/115 435/7.1 |
| 2008/0233132 A1 | 9/2008 | Miller et al. | |
| 2009/0004667 A1 | 1/2009 | Zichi et al. | |
| 2009/0023655 A1 | 1/2009 | Luttrell et al. | |
| 2010/0240732 A1 | 9/2010 | Gilboa | |

OTHER PUBLICATIONS

Blank, et al., "Systematic evolution of a DNA aptamer binding to rat brain tumor microvessels. selective targeting of endothelial regulatory protein pigpen", Journal of Biological Chemistry vol. 276 (19), 16464-16468 (2001).
Cao, Z, et al., "Molecular Aptamers for Real-Time Protein—Protein Interaction Study", Chem Eur J 11, 4502-4508 (2005).
Choi, Y, et al., "The RNA aptamer disrupts protein—protein interaction between b-catenin and nuclear factor-kB p50 and regulates the expression of C-reactive protein", FEBS Letters 583, 1415-1421 (2009).
Daniels, et al., "A tenascin-C aptamer identified by tumor cell SELEX: systematic evolution of ligands by exponential enrichment", Proc Natl Acad Sci 100 (26), 15416-15421 (2003).
Ellington, AD, et al., "Selection in vitro of single-stranded DNA molecules that fold into specific ligand-binding structures", Nature 355(6363); 850-852 (1992).
Hernandez, L, et al., "Methods for Evaluating Cell-Specific, Cell-Internalizing RNA Aptamers", Pharmaceuticals 6, 295-319 (2013).
Homann, et al., "Combinatorial selection of high affinity RNA ligands to live African trypanosomes", Nucleic Acids Res 27, 2006-2014 (1999).
Kahsai, A, et al. "Conformationally selective RNA aptamers allosterically modulate the beta 2-adrenoceptor", Nature Chemical Biology 12, 709-716 (2016).
Ku, T, et al., "Nucleic Acid Aptamers: An Emerging Tool for Biotechnology and Biomedical Sensing", Sensors 15(7), 16281-16313 (2015).
Morris, et al., "High affinity ligands from in vitro selection: complex targets", Proc Natl Acad Sci 95, 2902-2907 (1998).
Niozari, A, et al., "Aptamers for CD Antigens: From Cell Profiling to Activity Modulation", Molecular Therapy Nucleic Acids 6, 29-44 (2017).
Ohuchi, S, "Cell-SELEX Technology", Biores Open Access 1(6), 265-272 (2012).
Tripp, B, et al., "Carbonic anhydrase: new insights for an ancient enzyme", J Biol Chem 276(52), 48615-48618 (2001).
Veeramani, S, et al., "Abstract 1606: Targeting human T regulatory cells with novel Interleukin 2 alpha—IL2 complex-specific RNA aptamer", Cancer Research 77(13), Proceedings AACR Annual Meeting, Washington DC, Apr. 1-5, 2017.

(Continued)

*Primary Examiner* — Tracy Vivlemore
(74) *Attorney, Agent, or Firm* — Viksnins Harris Padys Malen LLP

(57) ABSTRACT

Disclosed herein are compositions including an aptamer bound to a complex, wherein the complex comprises at least two polypeptides. Accordingly, methods of using the aptamers and making the aptamers are also disclosed.

**17 Claims, 18 Drawing Sheets
(10 of 18 Drawing Sheet(s) Filed in Color)
Specification includes a Sequence Listing.**

(56) References Cited

OTHER PUBLICATIONS

Veeramani, S., et al., "Ligand-Receptor Complex-binding RNA aptamers to measure occupancy of IL2Rα (CD25) receptors by IL2", Cancer Center Scientific Retreat, Holden Comprehensive Cancer Center. Coralville Marriott Hotel and Convention Center, Coralville, IA (Jun. 20, 2018).

Wang, C., et al., "Single-stranded DNA aptamers that bind differentiated but not parental cells: subtractive systematic evolution of ligands by exponential enrichment", J Biotechnol 102(1), 15-22 (2003).

\* cited by examiner

A

B

Figures 8A-8B
Figure 8A
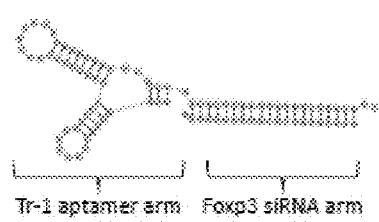
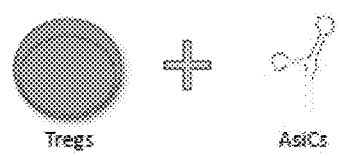
Figure 8B
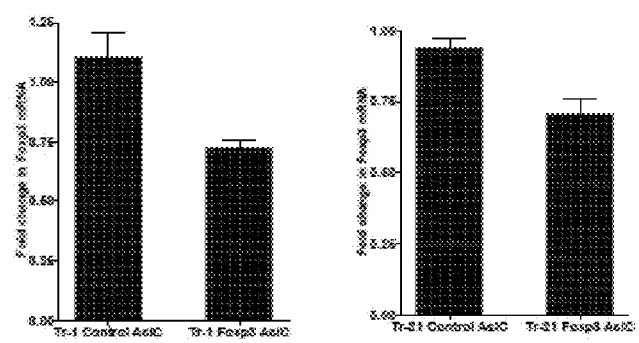

Figure 9A

Table 17

| Aptamer | Cluster |
|---|---|
| Tr-1 | Edit distance 1 cluster |
| Tr-2 | Tree distance 3 cluster |
| Tr-3 | Orphan |
| Tr-6 | Tree distance 5 cluster |
| Tr-7 | Tree distance 3 cluster |
| Tr-8 | Tree distance 1 cluster (first 30) |
| Tr-9 | Tree distance 0 and 1 cluster (first 30) |
| Tr-10 | Tree distance 3 cluster |
| Tr-11 | Tree distance 3 cluster |
| Tr-15 | Tree distance 3 cluster |
| Tr-16 | Tree distance 3 cluster |
| Tr-17 | Tree distance 3 cluster |
| Tr-19 | Tree distance 3 cluster |
| Tr-21 | Orphan |
| Tr-24 | Tree distance 1 cluster |
| Tr-26 | Tree distance 1 cluster |
| Tr-27 | Tree distance 7 cluster |
| Tr-30 | Tree distance 7 cluster |
| Tr-37 | Tree distance 1 cluster |
| Tr-61 | Orphan |
| Tr-177 | Tree distance 3 cluster |

Figure 9B

Table 18

| Code | Represents |
|---|---|
| A | Adenine |
| G | Guanine |
| C | Cytosine |
| T | Thymine |
| Y | Pyrimidine (C or U) |
| R | Purine (A or G) |
| W | weak (A or U) |
| S | strong (G or C) |
| K | keto (U or G) |
| M | amino (C or A) |
| D | A, G, U (not C) |
| V | A, C, G (not U) |
| H | A, C, U (not G) |
| B | C, G, U (not A) |
| X/N | any base |
| - | Gap |

A

B

C

D

E

SEQUENCE LISTING

```
<160> NUMBER OF SEQ ID NOS: 49

<210> SEQ ID NO 1
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
gggaggacga ugcggcacac cgaaaugucc cgacucagac gacucgcccg a            51

<210> SEQ ID NO 2
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
gggaggacga ugcgguccug ucgucuguuc gucccagac gacucgcccg a             51

<210> SEQ ID NO 3
<211> LENGTH: 51
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 3
gggaggacga ugcggcguuu ccucugguuc gucccagac gacucgcccg a            51

<210> SEQ ID NO 4
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
gggaggacga ugcggugagu cguucccuuc gucccagac gacucgcccg a            51

<210> SEQ ID NO 5
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
gggaggacga ugcgggccgu uguugugugc cgcccagac gacucgcccg a            51

<210> SEQ ID NO 6
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
gggaggacga ugcggauucu gguuacuggc cgcccagac gacucgcccg a            51

<210> SEQ ID NO 7
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
gggaggacga ugcggusmkk yskucysuuc gucccagac gacucgcccg a            51

<210> SEQ ID NO 8
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(23)
<223> OTHER INFORMATION: a, c, u, g, unknown or other
<220> FEATURE:
<221> NAME/KEY: modified_base
<222> LOCATION: (26)..(27)
<223> OTHER INFORMATION: a, c, u, g, unknown or other

<400> SEQUENCE: 8
gggaggacga ugcggunnnn nnnucnnuuc gucccagac gacucgcccg a            51
```

<210> SEQ ID NO 9
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
gggaggacga ugcggvbybu bsuydbkkkc skccccagac gacucgcccg a        51

<210> SEQ ID NO 10
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(17)
<223> OTHER INFORMATION: a, c, u, g, unknown or other
<220> FEATURE:
<221> NAME/KEY: modified_base
<222> LOCATION: (19)..(19)
<223> OTHER INFORMATION: a, c, u, g, unknown or other
<220> FEATURE:
<221> NAME/KEY: modified_base
<222> LOCATION: (21)..(21)
<223> OTHER INFORMATION: a, c, u, g, unknown or other
<220> FEATURE:
<221> NAME/KEY: modified_base
<222> LOCATION: (25)..(26)
<223> OTHER INFORMATION: a, c, u, g, unknown or other

<400> SEQUENCE: 10
gggaggacga ugcggnnynu nsuynnkkkc skccccagac gacucgcccg a        51

<210> SEQ ID NO 11
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(19)
<223> OTHER INFORMATION: a, c, u, g, unknown or other
<220> FEATURE:
<221> NAME/KEY: modified_base
<222> LOCATION: (21)..(22)
<223> OTHER INFORMATION: a, c, u, g, unknown or other
<220> FEATURE:
<221> NAME/KEY: modified_base
<222> LOCATION: (25)..(29)
<223> OTHER INFORMATION: a, c, u, g, unknown or other
<220> FEATURE:
<221> NAME/KEY: modified_base
<222> LOCATION: (31)..(32)
<223> OTHER INFORMATION: a, c, u, g, unknown or other

<400> SEQUENCE: 11
gggaggacga ugcggnnnnu nnuunnnnnc nnccccagac gacucgcccg a        51

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: Synthetic

```
                                primer

<400> SEQUENCE: 12
taatacgact cactataggg aggacgatgc gg                                    32

<210> SEQ ID NO 13
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tcgggcgagt cgtctg                                                      16

<210> SEQ ID NO 14
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(36)
<223> OTHER INFORMATION: a, c, t, g, unknown or other

<400> SEQUENCE: 14
tcgggcgagt cgtctgnnnn nnnnnnnnn nnnnnccgc atcgtcctcc c                  51

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tatagggagg acgatgcgg                                                   19

<210> SEQ ID NO 16
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
gaacagacga cagga                                                       15

<210> SEQ ID NO 17
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
gaaccagagg aaac                                                        14

<210> SEQ ID NO 18
<211> LENGTH: 15
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 18
gaagggaacg actca                                                         15

<210> SEQ ID NO 19
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
gcacacaaca acggc                                                         15

<210> SEQ ID NO 20
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
gggaggacga ugcggukuuu kwwkukgggc ygccccagac gacucgcccg a                  51

<210> SEQ ID NO 21
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
gggaggacga ugcgguuggu guagugggc cgccccagac gacucgcccg a                   51

<210> SEQ ID NO 22
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
gggaggacga ugcggcguky vsucugsyyy cuccccagac gacucgcccg a                  51

<210> SEQ ID NO 23
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
gggaggacga ugcggugruu uguucccyuc guccccagac gacucgcccg a                  51

<210> SEQ ID NO 24
<211> LENGTH: 51
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 24
gggaggacga ugcgggcyku wyuuuhuugc ygccccagac gacucgcccg a            51

<210> SEQ ID NO 25
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
gggaggacga ugcggwkyuu wwwuwyuugc cgccccagac gacucgcccg a            51

<210> SEQ ID NO 26
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
gggaggacga ugcggaccgu ggaguguugc cgccccagac gacucgcccg a            51

<210> SEQ ID NO 27
<211> LENGTH: 50
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
gggaggacga ugcgguagug agucgukgcc gccccagacg acucgcccga             50

<210> SEQ ID NO 28
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
gggaggacga ugcggguagu gagucguggc cgccccagac gacucgcccg a            51

<210> SEQ ID NO 29
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
gggaggacga ugcggawucu gguuwmukgc cgccccagac gacucgcccg a            51

<210> SEQ ID NO 30
<211> LENGTH: 51
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 30
gggaggacga ugcgguguwy uwkwuuyccc gucccagac gacucgcccg a         51

<210> SEQ ID NO 31
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
gggaggacga ugcgguguag uggguuccc gucccagac gacucgcccg a          51

<210> SEQ ID NO 32
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
gggaggacga ugcggudwuk wwkyyybyks ugcccagac gacucgcccg a         51

<210> SEQ ID NO 33
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
gggaggacga ugcgguguug auguucccug ugcccagac gacucgcccg a         51

<210> SEQ ID NO 34
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
gggaggacga ugcggusucu gyggwkksbs ykcccagac gacucgcccg a         51

<210> SEQ ID NO 35
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
gggaggacga ugcggugucu guggaguggc cgcccagac gacucgcccg a         51

<210> SEQ ID NO 36
<211> LENGTH: 51
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 36
gggaggacga ugcggugugd kkuwwuuysy ykccccagac gacucgcccg a         51

<210> SEQ ID NO 37
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
gggaggacga ugcggugugg gaucaguggc cgccccagac gacucgcccg a         51

<210> SEQ ID NO 38
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
gggaggacga ugcgguguwk rwacagukgc cgccccagac gacucgcccg a         51

<210> SEQ ID NO 39
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
gggaggacga ugcgguguug auacaguggc cgccccagac gacucgcccg a         51

<210> SEQ ID NO 40
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
gggaggacga ugcggucugw wswykuuysc skccccagac gacucgcccg a         51

<210> SEQ ID NO 41
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
gggaggacga ugcggucugu uguuguuccc gucccccagac gacucgcccg a         51

<210> SEQ ID NO 42
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
gggaggacga ugcgguccuk gmyukuyguk kkccccagac gacucgcccg a         51

<210> SEQ ID NO 43
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
gggaggacga ugcgguccug gcuugucguu guccccagac gacucgcccg a         51

<210> SEQ ID NO 44
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
gggaggacga ugcgguywbu yukyyccuks ygccccagac gacucgcccg a         51

<210> SEQ ID NO 45
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
gggaggacga ugcggucucu cgucccgugc cgccccagac gacucgcccg a         51

<210> SEQ ID NO 46
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
gggaggacga ugcggywukw uuwuuukgcc guccccagac gacucgcccg a         51

<210> SEQ ID NO 47
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
gggaggacga ugcgguguga uguaguggcc guccccagac gacucgcccg a         51

<210> SEQ ID NO 48
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 48
gggaggacga ugcggukukb yyywdkuccc gucccagac gacucgcccg a        51

<210> SEQ ID NO 49
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
gggaggacga ugcgguggcc uguaguuccc gucccagac gacucgcccg a        51
```

NUCLEIC ACID APTAMERS

RELATED APPLICATIONS

This application claims priority to U.S. Provisional Patent Application No. 62/547,357 filed Aug. 18, 2017, the entirety of which is incorporated herein by reference.

STATEMENT AS TO FEDERALLY SPONSORED RESEARCH

This invention was made with government support under R01 CA097274 awarded by the National Institutes of Health. The government has certain rights in the invention.

SEQUENCE LISTING

The instant application contains a Sequence Listing which has been filed electronically in ASCII format and is hereby incorporated by reference in its entirety. Said ASCII copy, created on Jan. 10, 2019, is named 17023_209US1_SL.txt and is 12,637 bytes in size.

BACKGROUND

Aptamers are nucleic acid molecules having specific binding affinity to non-nucleic acid or nucleic acid molecules through interactions other than classic Watson-Crick base pairing. Aptamers are described e.g., in U.S. Pat. Nos. 5,475,096; 5,270,163; 5,589,332; 5,589,332; and 5,741,679.

Aptamers, like peptides generated by phage display or monoclonal antibodies (MAbs), are capable of specifically binding to selected targets. Created by an in vitro selection process from pools of random sequence oligonucleotides, aptamers have been generated for many proteins including growth factors, transcription factors, enzymes, immunoglobulins, and receptors. A typical aptamer is 7.5-20 kDa in size (15-60 nucleotides), binds its target with sub-nanomolar affinity, and discriminates against closely related targets (e.g., will typically not bind other proteins from the same gene family). A series of structural studies have shown that aptamers are capable of using the same types of binding interactions (hydrogen bonding, electrostatic complementarity, hydrophobic contacts, steric exclusion, etc.) that drive affinity and specificity in antibody-antigen complexes.

Selection of aptamers is through a process termed SELEX (systematic evolution of ligands by exponential enrichment) (*Nature. 1992 Feb. 27; 355(6363):850-2). Targets of aptamers are usually pure molecules such as proteins and small molecules. More complex biological species, such as red blood cells membrane and a single protein on live trypanosomes, have also been used as the targets in SELEX (J Biol Chem. 2001 Dec. 28; 276(52):48644-54, Proc Natl Acad Sci USA. 2003 Dec. 23; 100(26):15416-21, J Biotechnol. 2003 Apr. 10; 102(1):15-22, Proc Natl Acad Sci USA. 1998 Mar. 17; 95(6):2902-7, Nucleic Acids Res. 1999 May 1; 27(9):2006-14, J Biol Chem. 2001 May 11; 276(19): 16464-8).

SUMMARY

Described herein are compositions that comprise aptamers that are bound to complexes. Complexes as used herein refers to groups of molecules having at least 2, at least 3, at least 4, at least 5, at least 6 or greater distinct molecules that are co-located near each other. The molecules can be described as members of a complex. The molecules can be selected from combinations of small organic, inorganic molecules or partially organic molecules. Examples of molecules include proteins, antibodies, active pharmaceutical ingredients including chemotherapeutics, and markers used in diagnostics. Complexes are when more than one molecule is located in a close enough proximity to another molecule that an aptamer can specifically bind to the combination of the more than on molecule. In some instances, the complexes are formed by a receptor-ligand, an antibody-epitope binding, a first domain and a second domain of a multi-domain protein, or an active pharmaceutic ingredient and its associated active site.

One of ordinary skill in the art will appreciate that specific binding is a relative term meaning that an aptamer binds more specifically to one molecule than it does to another molecule. Some processes described herein allow for the making of aptamers that preferentially bind to a particular complex as compared to the aptamers ability to bind to the individual members of the complex. This preferential binding is referred to as specific binding and it can be assessed using any method known in the art. For example, a particular aptamer can be separately contacted with an immobilized complex, an individual immobilized member of the complex, and a second immobilized individual member from the complex. The three samples can then be subjected to increasingly stringent physical conditions, for example changes in ionic strength, surfactant concentrations, temperatures and the like. The amount of aptamer that remains bound can then be determined, and, if there is a higher concentration or quantity of aptamer bound to the complex as compared to the individual molecules from that complex, the aptamer can be characterized as specifically binding to the complex. One of ordinary skill in the art will appreciate that specific binding can be additionally characterized by the strength of the binding. One example of characterizing the strength of the specific binding of an aptamer to a complex is by the amount of aptamer that remains bound to the complex as compared to the amount of aptamer that remains bound to one or more of the individual molecules in the complex. Expressed in this way an aptamer can be characterized as having at least 50%, 55%, 60%, 65%, 70%, 75%, 80%, 85%, 90%, or 95% more binding as compared to a specific individual molecule in the complex or to all of the individual molecules in the complex. The conditions under which such determination is made can be selected for the desired application of the aptamer. For example, physiological conditions may be appropriate if the aptamer is used to bind to complexes in a mammal such as a human.

One of ordinary skill in the art will appreciate that by using a pair of aptamers, a first aptamer that preferentially binds to a complex and a second aptamer that preferentially binds to an unbound member of the complex, one can quantify the amount of complexes in a sample as compared to the amount of unbound complex members. Accordingly, methods of detecting the relative bound amount of complex members are described herein. These methods can be used as research tools and diagnostics. Example 5, provided below illustrates a method that is useful for measuring IL2 occupancy on CD25 (also called as IL2RA and used interchangeably). This approach to using a pair of aptamers with one that preferentially binds to the complex and a second that preferentially to an unbound member of the complex has been designated LIRECAP for "LIgand REceptor Complex APtamer".

The aptamers described herein are useful, among other things, for binding to complexes that are located on or near the extracellular region of a cell. For example, a molecule in the complex can have an extracellular domain that is then associated with a second molecule to form a complex. The extracellular domain does not have to be from a molecule that is completely extracellular, one of ordinary skill in the art will appreciate that many molecules are partially extracellular and that a complex can be formed with the exposed portion of the molecule. One of ordinary skill in the art will also appreciate that a complex can be formed by molecules expressed by a single cell, by molecules on two cells with each contributing a molecule to the complex that is bound by the aptamer, by molecules where one or both are not on a cell but are in the extracellular matrix, or by molecules where one or both are in soluble form.

As described herein the complexes that are bound by the aptamers can include multiple molecules. Of specific interest are complexes that include at least one molecule selected from the group consisting of those identified in Tables 12, 13, and 14. Of particular interest are complexes that include immunologically active molecules such as cytokines, ligands and their receptors. As described below in an illustrative the example, aptamers that bind to a complex for CD25 and IL2 are described.

The aptamers described herein can be additionally modified to include at least 1, 2, 3, 4, 5, 6, 7, 8, 9 or 10 modifications that increase the stability or specificity of the aptamer. Such modifications are characterized as differences to the structure of the nucleotide sequence of the aptamer as compared to a natural nucleotide sequence. These modifications are described in detail herein.

One of ordinary skill in the art will appreciate that aptamers that specifically bind to a complex can be identified and sequenced and that once the sequence of the aptamer is known one of ordinary skill in the art can make alterations, substitutions and/or deletions to the aptamer sequence and test the modified sequence for its ability to selectively bind to a complex. One of ordinary skill in the art will appreciate that when a specific aptamer is referred to such reference includes sequences that share at least 95%, 90%, 85%, 80%, 75%, 70%, 65%, 60%, or 50% sequence identity to the identified sequence.

The aptamers described herein can also be linked to additional moieties. These moieties can be useful for detecting the presence of the aptamer, isolating molecules bound to the aptamer, delivering a therapeutic molecule to the location of the complex or stabilizing the complex. One of ordinary skill in the art will appreciate that there are a variety of moieties that can be used to fulfill these functions and any moiety known in the art to be useful can be used. Exemplary moieties are described further herein.

Methods of making and using the aptamers that bind selectively to complexes are also described. The aptamers can be made using any method known in the art. For example, methods based upon the SELEX method can be used to identify aptamers.

Once a complex-binding aptamer is made it can be used in a variety of methods depending upon the complex to which it binds. Accordingly, methods of using the aptamers are also included in the disclosure. One of ordinary skill in the art will appreciate that there are many uses for the aptamers and any such methods are intended. Exemplary methods can include the steps of contacting a sample with the aptamer and detecting the bound aptamer, isolating the biological material that is bound to the aptamer, delivering a therapeutic molecule to the location of the bound aptamer, stabilizing the complex to which the aptamer binds, or combinations thereof. In instances where the aptamer is used to isolate biological material, such as cells, the aptamer bound to the complex on the cells can be isolated. Isolating can be accomplished using multiple methods, for example the aptamer can be immobilized, thus allowing for cells displaying the complex to be immobilized upon aptamer binding or the aptamer can be linked to a moiety that facilitates separation of the bound aptamer from the remainder of the sample.

In some embodiments the cell type that is detected and/or isolated using the aptamer is an immune cell. Any immune cell type can be detected and/or isolated, for example the cell types described in Tables 12 and 13 can be detect and/or isolated. In some examples, the immune samples are T cells, such as regulatory T cells (Tregs). In other examples the cells can be cancer cells such as circulating tumor cells.

The samples described herein can be any sample that includes the molecules that can form the complex. The aptamers can then be used to bind to the complex and the bound aptamers can be detected. In some instances when measuring the relative amount of bound members of a complex is desired, the sample can also include an aptamer recognizing one or more unbound members of the complex and the aptamer bound to the unbound member of the complex can be detected. The samples can be cells, culture samples, body fluid samples, tissue samples and the like. The aptamers can also be used to bind to complexes inside of a body cavity for instance during surgery when the aptamer is applied as part of a wash. In this context the aptamer can provide cell specific delivery and detection.

BRIEF DESCRIPTION OF DRAWINGS

The patent or application file contains at least one drawing executed in color. Copies of this patent or patent application publication with color drawing(s) will be provided by the Office upon request and payment of the necessary fee.

signifying reduction in sequence complexity as SELEX rounds progressed. (C) Percent of sequence enrichment during each round was calculated as 100−[(Unique sequences/Total reads)*100]. The data shows that a linear enrichment of Treg-binding sequences occurred from SELEX rounds 1 through 4, followed by a plateau in enrichment after round 7. (D) A progressive enrichment of copy numbers of individual aptamer candidates that were selected for further analysis are shown.

FIGS. 3A-3D. (A) Synthesized top enriched aptamers were evaluated for their ability to bind to CD4$^+$CD25$^{high}$ Tregs and CD4$^+$CD25$^{neg}$ Teff cells. All tested aptamers demonstrated preferential and greater binding to Tregs than they did to Teff cells. In addition, all the selected aptamers bound more than the control aptamer, C-248. Shown here is the representative data of two independent sets of experiments (Mean+/−SEM). (B) Five of the lead aptamers (Tr-1, Tr-6, Tr-7, Tr-8 and Tr-11) from the top selected candidates show significantly greater binding to recombinant human CD25 when compared to the control aptamer, C-248 ((Mean+/−SEM); N=2). (C) An ELISA-based assay demonstrated that none of the CD25-binding aptamers altered the EC$_{50}$ of the IL2-CD25 interaction (N=3). A representative plot from three independent sets of experiments is shown. (D) Phosphorylation of STAT5 as shown as median fluorescent intensity) in human Tregs induced by IL2 is not influenced by CD25 aptamers as demonstrated by flow cytometry. A representative plot of three independent sets is shown.

Figure 4A:
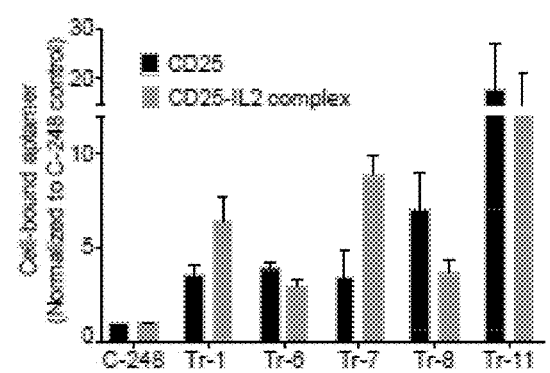
Figure 4B:
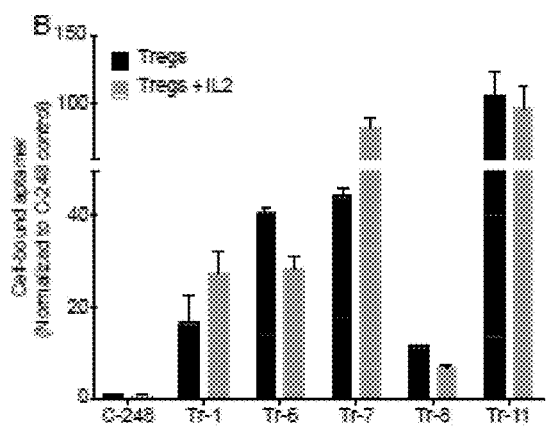

FIGS. 4A-4B. CD25-binding aptamers display differential binding when the receptor is occupied by its ligand, IL2. (A) Ability of the CD25-binding aptamers to recognize receptor-ligand complex formed by the interaction between CD25 and its natural ligand, IL2, was tested by comparing their binding to CD25 receptor-coated beads incubated in the presence (CD25-IL2 complex) or absence (CD25) of IL2. (B) The ability of the aptamers showing varying affinity to CD25-IL2 complex was further tested in a cell-based binding assay by measuring the binding of indicated aptamers to primary Tregs incubated in the presence (Tregs+IL2) or absence (Tregs) of IL2.

FIGS. 5A-5E. IL2 occupancy of CD25 using LIRECAPs in multiplex probe-based RT-qPCR assay. A multiplex TaqMan probe-based RT-qPCR assay was designed to quantify the fraction of CD25 receptors occupied in the sample. LIRECAPs that preferentially recognized IL2-CD25 ligand-receptor complexes (Tr-1 or Tr-7) was paired with aptamers that preferentially recognized unoccupied CD25 receptors (Tr-8). CD25 with different IL2 occupancy was created as described in the Methods section. Binding of aptamer pairs to the complex was measured by RT-qPCR assay using SEL2-specific primers and FAM-labeled (Tr-1 and Tr-7) or TET-labeled (Tr-8) TaqMan probes. (A) Binding of Tr-1 aptamer was plotted against log 2 concentrations of IL2 added to CD25. Tr-1 showed positive correlation with increasing receptor occupancy. (B) Binding of Tr-7 aptamer was plotted against logarithmic concentrations of IL2 added to CD25, which shows positive correlation with increasing receptor occupancy. (C) Binding of Tr-8 aptamer was plotted against logarithmic concentrations of IL2 added to CD25. Tr-1 showed negative correlation with increasing receptor occupancy. (D) Ratio of aptamer binding was obtained by dividing the protein-bound Tr-1 level to bound Tr-8 levels. Binding ratio was plotted against logarithmic concentrations of IL2. (E) Ratio of bound levels of Tr-7 to Tr-8 was derived and was plotted against the logarithmic concentrations of IL2.

Figures 6A, 6B, 6C:
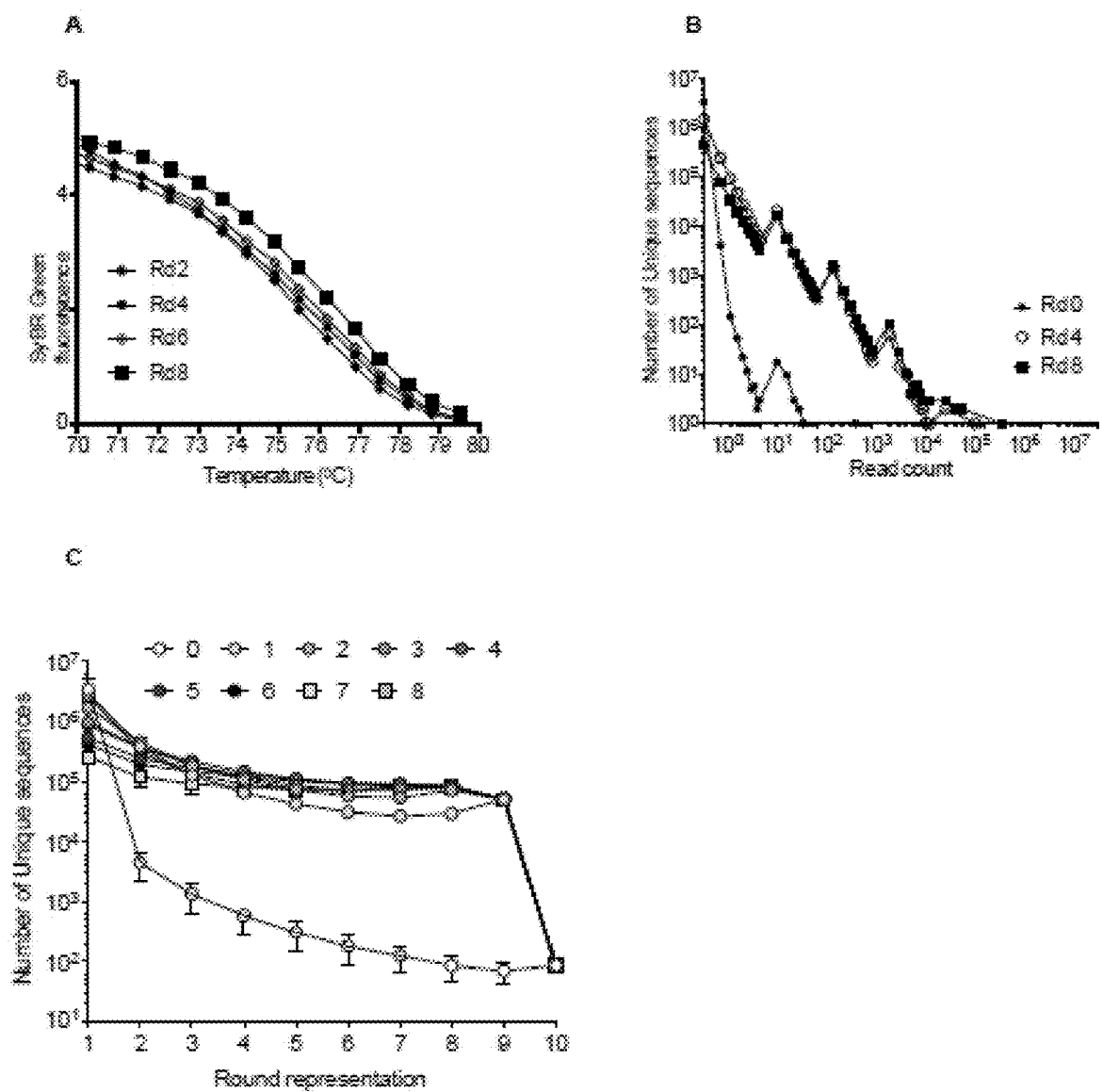

FIGS. 6A-6C. Bioinformatics analysis of primary human Treg cell-based SELEX-enriched aptamers. The complexity of the Treg-binding aptamer pools from every few rounds of SELEX were initially tested using a DNA melt assay (PLoS One 2012; 7(9):e43836). Aptamer pools from the later rounds of SELEX shows higher melting temperature than the earlier rounds indicative of enrichment of related sequence and reduced sequence complexity. Abundance analysis of the read counts plotted against the unique aptamer sequences from every few rounds of SELEX. Later rounds of SELEX (Rd 4 and Rd 8) showed increased abundance (read count) indicative of enrichment of highly homologous Treg-binding sequences than the initial library (Rd 0). Persistence analysis of the round representation of unique aptamer sequences from each round of SELEX (Rounds 1-8) as compared to the round representation of aptamer sequences from round 0.

Figure 7A:
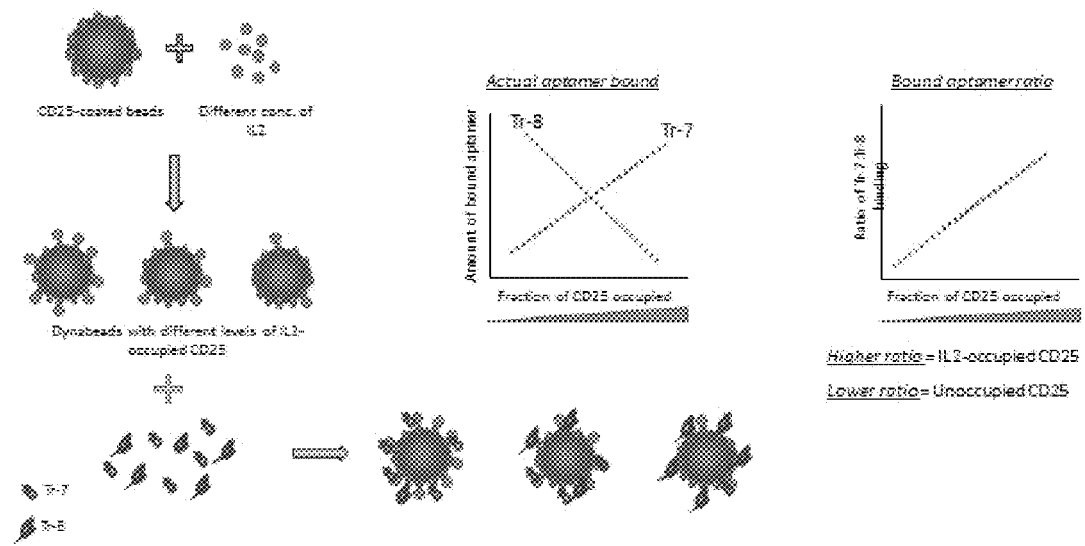
Figure 7B:
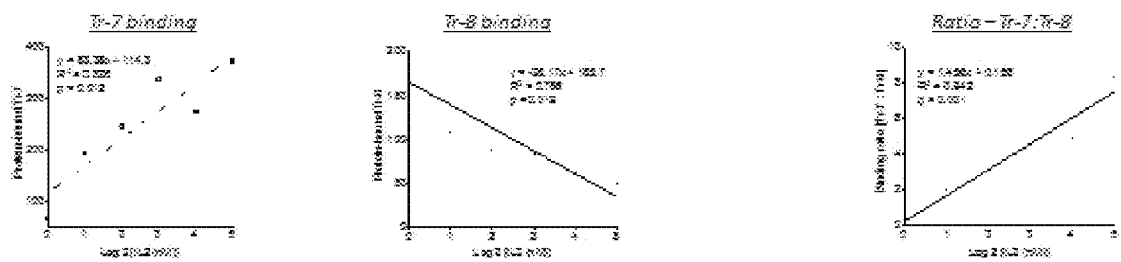

FIGS. 7A-7B. (A) Schematic representation of the occupancy assay to determine fraction of IL2R∝ receptors occupied by its ligand IL2. Aptamers binding preferentially to unoccupied IL2RA (Tr-8) versus the IL2-occupied IL2RA (Tr-7) were mixed in equimolar quantities. This was added to IL2RA-coated Dynabeads pre-incubated with various concentrations of IL2 to create receptor-ligand complexes with various levels of occupancy. Aptamer binding was quantified by RT-qPCR assay using primers that bind to both aptamers and fluorescent probes specific to the variable region in each aptamer. The amount of binding of aptamers and their ratios were plotted against the fraction of receptor occupied. The standard curve thus created using the binding ratio can be used to measure receptor occupancy in test samples (B) Actual binding assay done as explained above. Tr-7 binding showed a positive correlation with increasing concentrations of IL2 added, while Tr-8 binding showed an inverse correlation with the concentrations of IL2 added. The binding ratios between Tr-7 and Tr-8 showed significant linear correlation to the amount of IL2 added which in turn reflects the fraction of IL2RA occupied by IL2.

FIGS. 8A-8B. FIG. 8A shows a schematic of an aptamer-siRNA chimeras (AsiCs) created by linking Tr-1 aptamer with Foxp3 siRNA. Similar molecules were also created containing a 1) control siRNA linked to Tr-1 (Tr-1 Control AsiC), 2) Tr-1 aptamer with Foxp3 siRNA (Tr-1 Foxp3 AsiC, shown in schematic), 3) Tr-21 aptamer with control siRNA (Tr-21 Control AsiC) and 4) Tr-21 aptamer with Foxp3 siRNA (Tr-21 Foxp3 AsiC). Enriched human Tregs were treated with above-said chimeric aptamer molecules and cultured for 3 days. At the end of day 3, cells were lysed to extract mRNA. Foxp3 and β-Actin (house-keeping gene) mRNA was quantified by RT-qPCR using Foxp3 and β-Actin mRNA-specific PCR primers, respectively. Results are shown in FIG. 8B as the quantity of Foxp3 mRNA normalized to the quantity of β-actin mRNA.

FIGS. 9A-9B. FIG. 9A shows Table 17 which provides a list of the clusters found that are associated with the indicated aptamer and FIG. 9B Table 18 which provides the legend for the abbreviations for the nucleic acids used in FIG. 10. Data shows successful knock down of Foxp3 mRNA in Tr-1 Foxp3 and Tr-21 Foxp3 AsiC-treated Tregs when compared to the respective control AsiCs. Data is presented as fold changes in Foxp3 mRNA copy number.

Figure 10A:
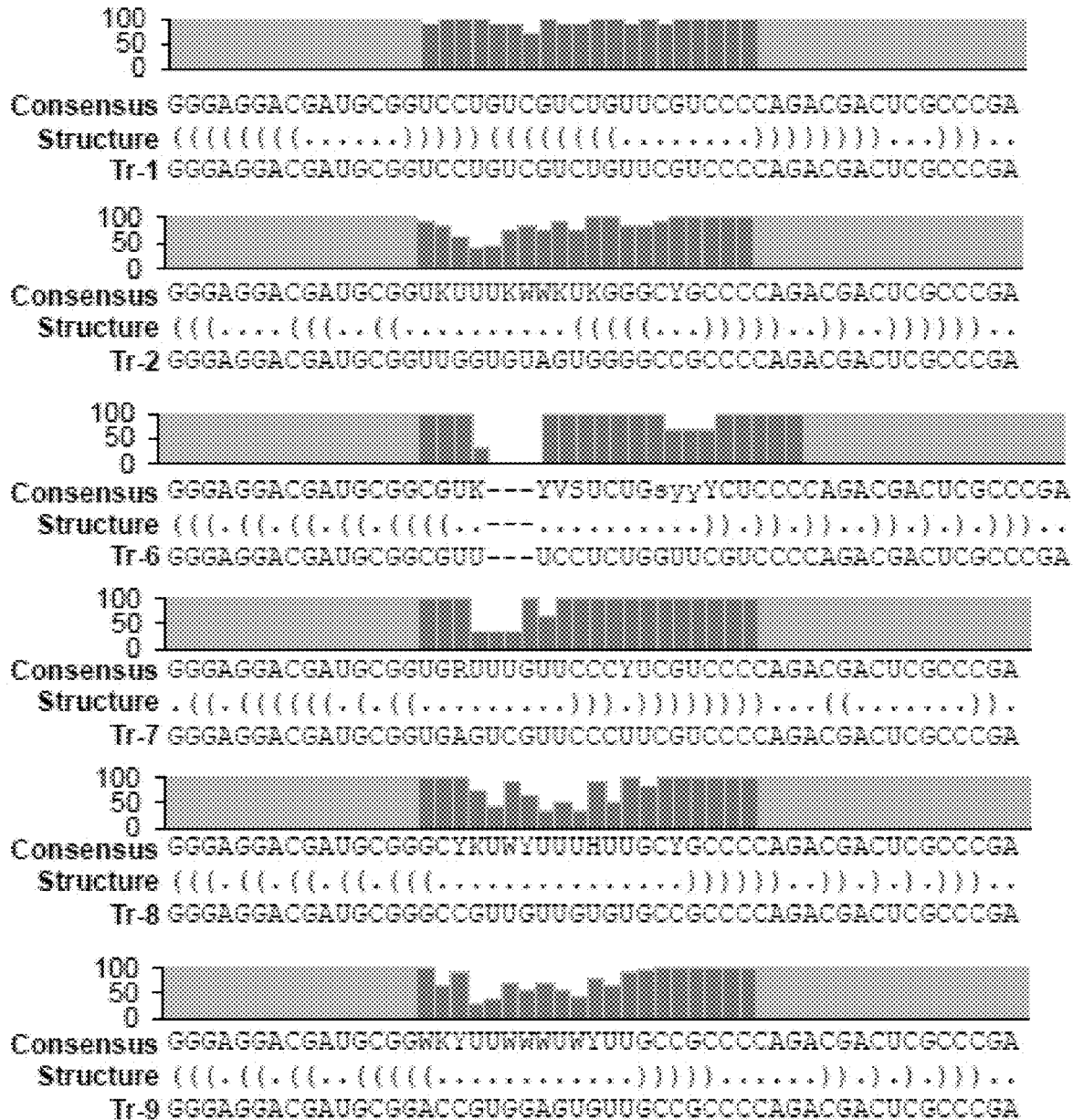
Figure 10B:
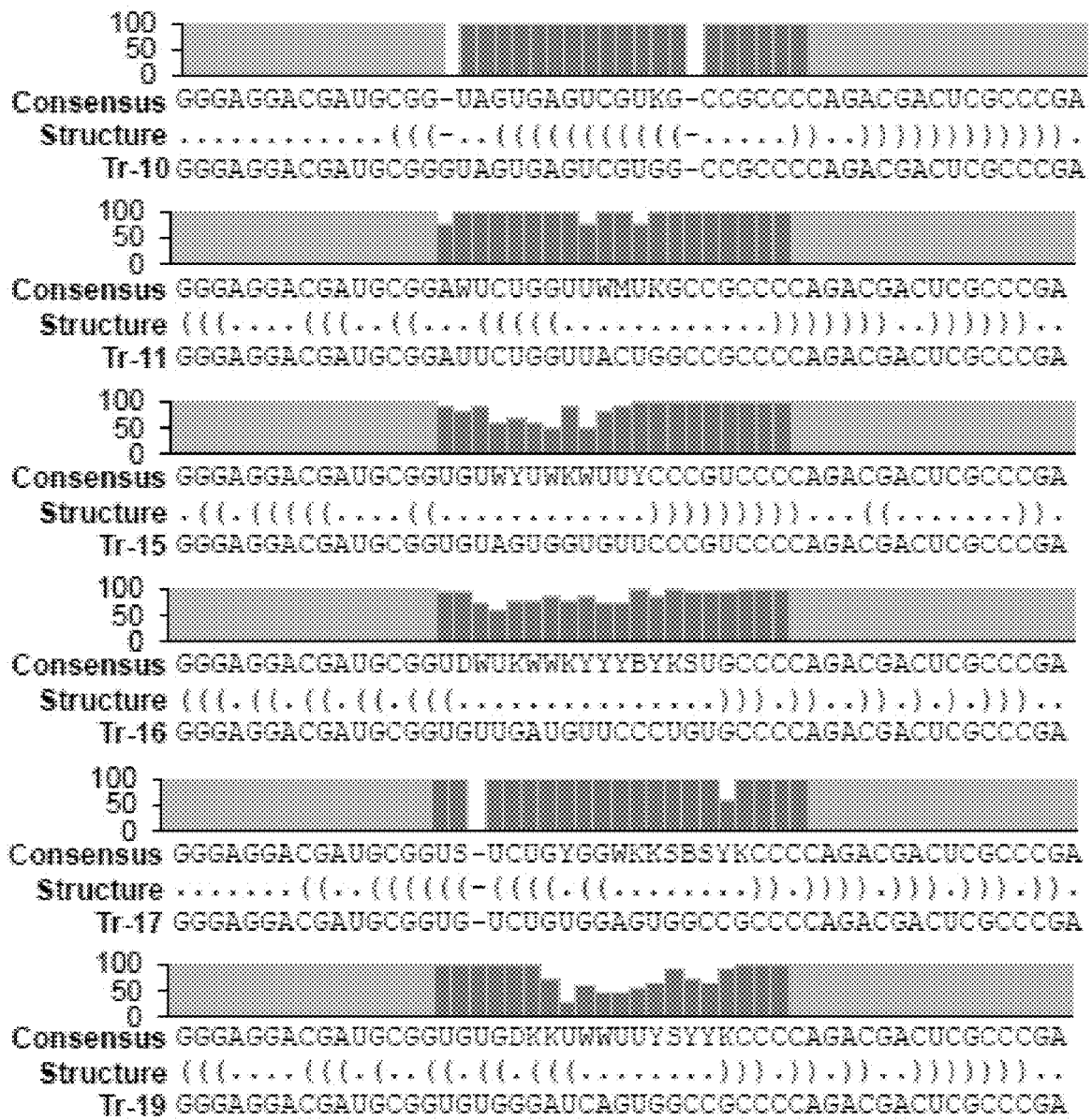
Figure 10C:
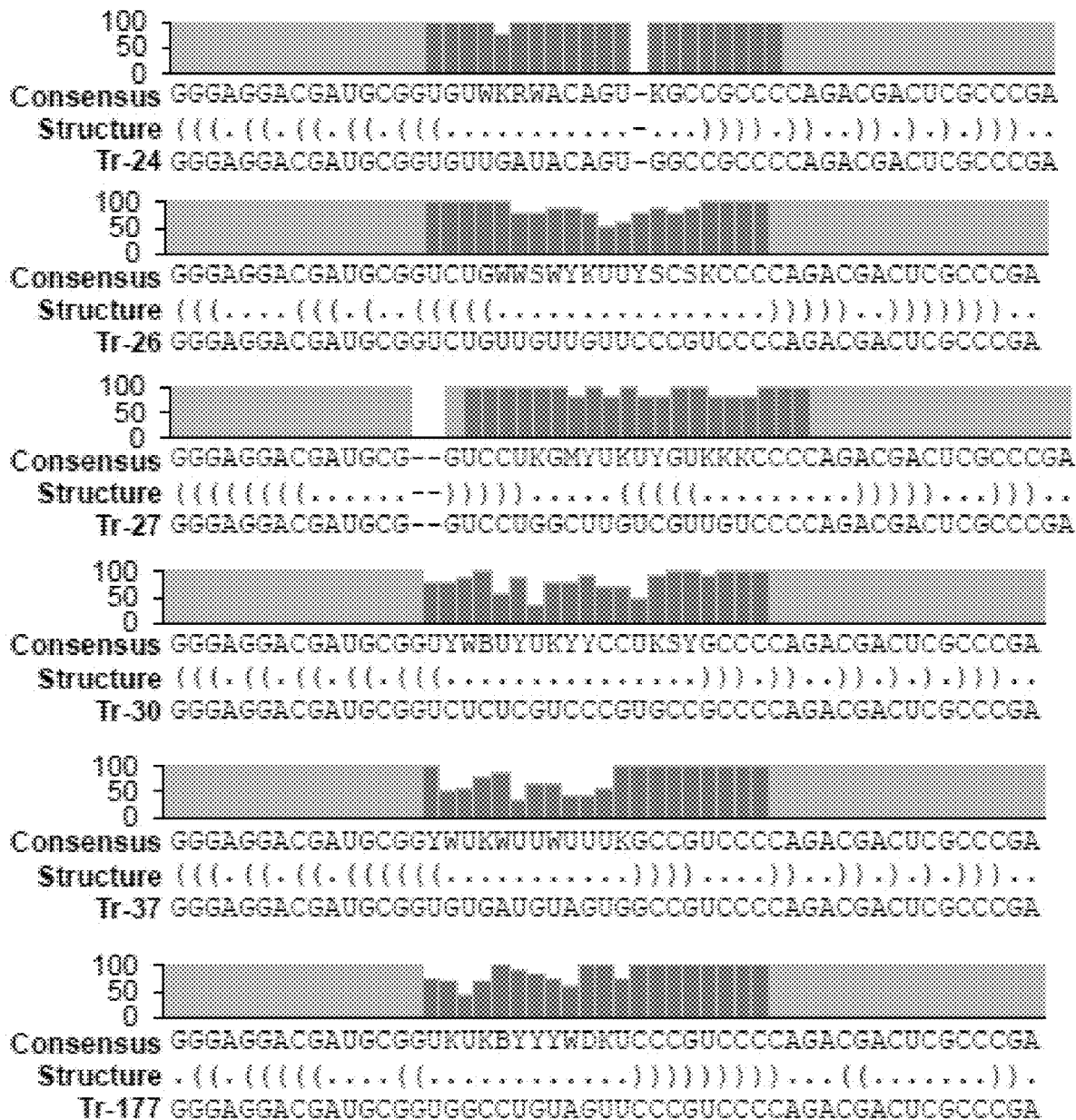

FIGS. 10A-10C show the consensus sequences for the aptamers identified in Table 17, FIG. 9. FIG. 10A discloses SEQ ID NOS 2, 2, 20-22, 3, 23, 4, 24, 5 and 25-26, FIG. 10B discloses SEQ ID NOS 27-29, 6 and 30-37 and FIG. 10C discloses SEQ ID NOS 38-49, all respectively, in order of appearance.

FIGS. 11A-11E. Tr-1 (A) and Tr-7 (B) bind more extensively to CD25 as its IL2 occupancy increases demonstrating its enhanced binding to the IL2-CD25 complex. In contrast, Tr-8 (C) binding to CD25 decreases as IL2 occupancy increases demonstrating its enhanced binding to the unoccupied CD25 compared to the IL2-CD25 complex. The ratio Tr-1 to Tr-8 binding (D) and Tr-7 to Tr-8 binding (E) correlates strongly with IL2 occupancy of CD25. A representative linear regression plot from four independent sets of experiment is shown.

Figures 12A, 12B, 12C:
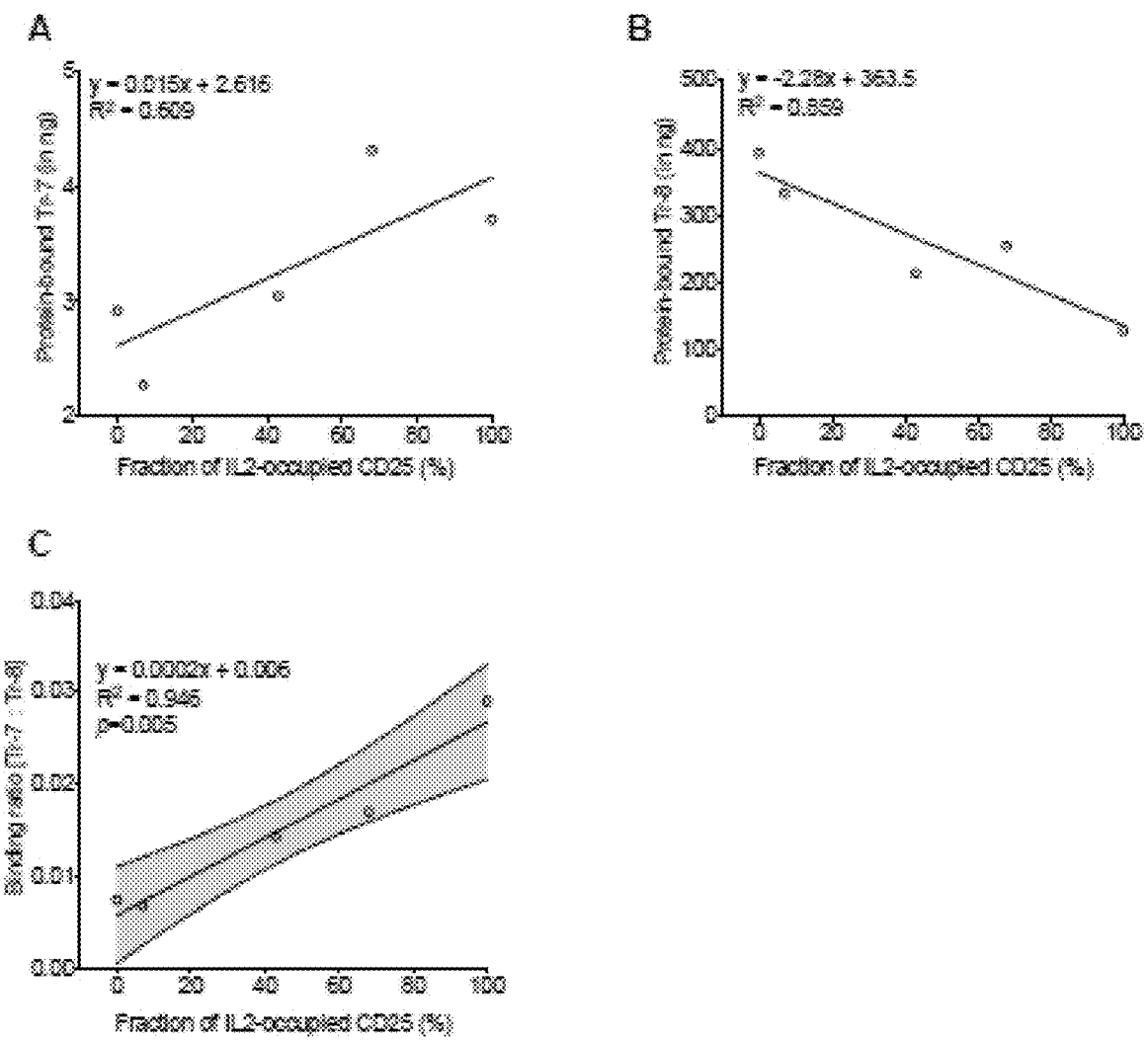

FIGS. 12A-12C. Healthy human serum samples containing CD25 with various levels of IL2 occupancy were created by addition of recombinant CD25 and IL2. A positive correlation is seen between Tr-7 binding and increasing IL2 occupancy of CD25 (A) and a negative correlation is seen between Tr-8 binding and increasing IL2 occupancy of CD25 increases is seen (B) The ratio of Tr-7 to Tr-8 binding correlates strongly with IL2 occupancy of CD25 in serum (C) as is seen in media. A representative linear regression plot of two independent sets of experiment is shown.

Figure 13:
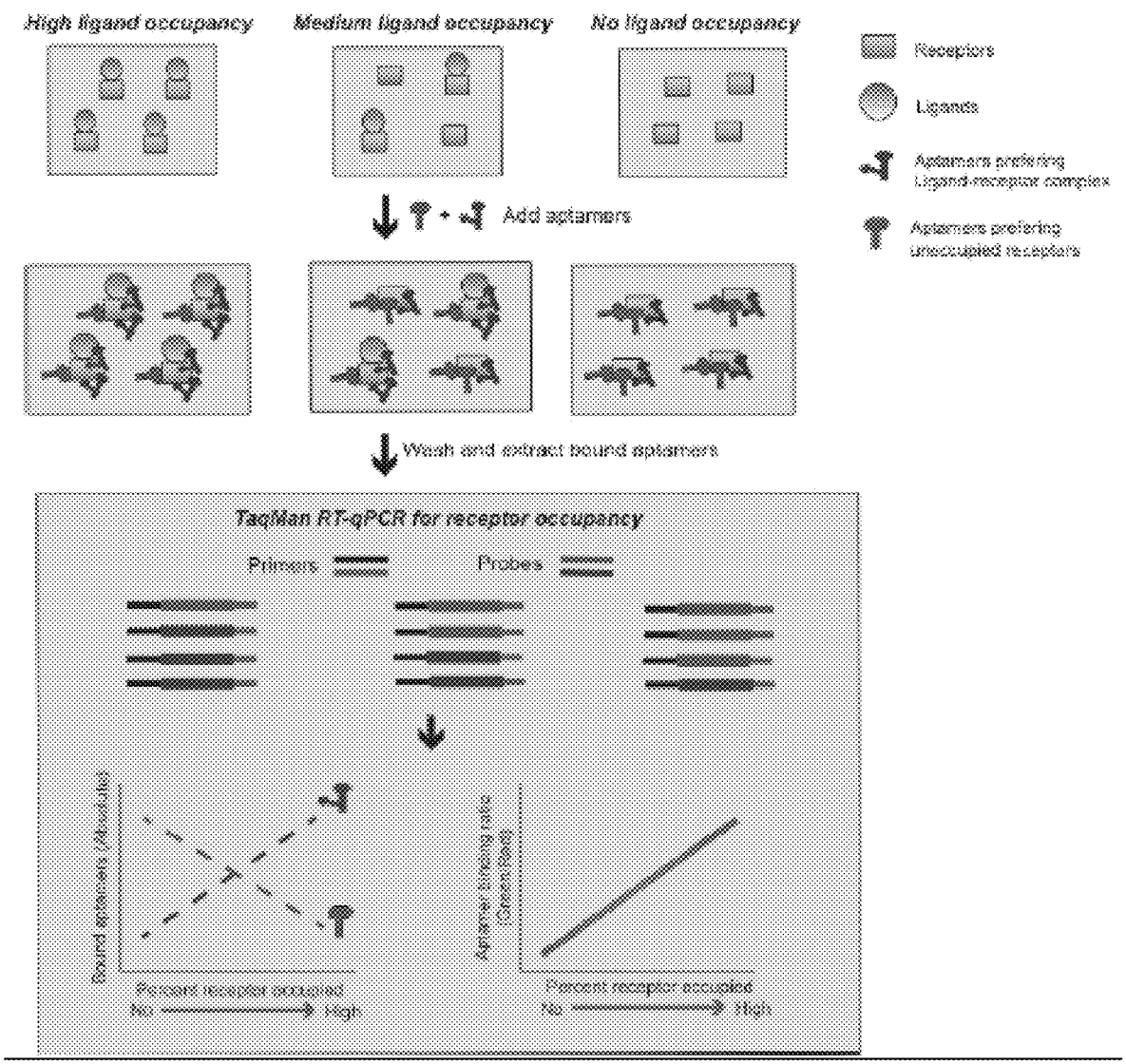

FIG. 13. Differential binding of aptamers to unoccupied versus ligand-occupied receptor can be used to determine the fraction of receptor occupancy in biospecimens. After preparation of cells or immunoprecipitation of soluble receptor, aptamer pairs consisting of equimolar mix of aptamers preferring the complex and aptamer preferring the unoccupied receptors are incubated with samples with unknown levels of receptor occupancy. Aptamers preferring the complex bind to a greater degree in samples with higher receptor occupancy by ligand. Aptamers preferring the unoccupied receptors bind to a greater degree in samples with lower receptor occupancy by ligand. Aptamer levels are then quantified by probe-based RT-qPCR. The ratio of binding of aptamers to each sample is determined and compared to a standard curve to determine the percent of receptors occupied by ligand in the sample.

Figure 14:
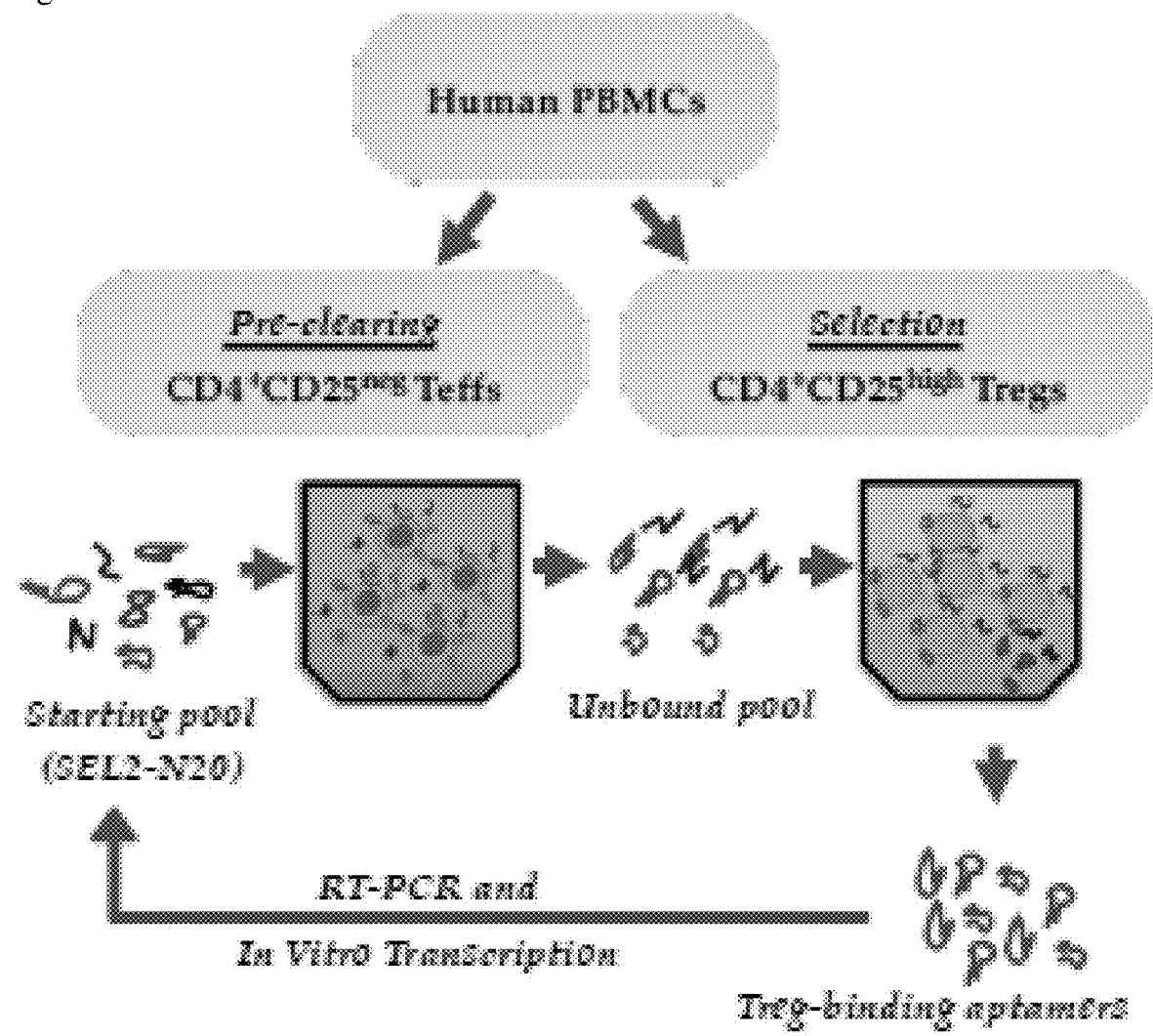

FIG. 14. Treg cell-based SELEX of LIRECAPs.

Figure 15:
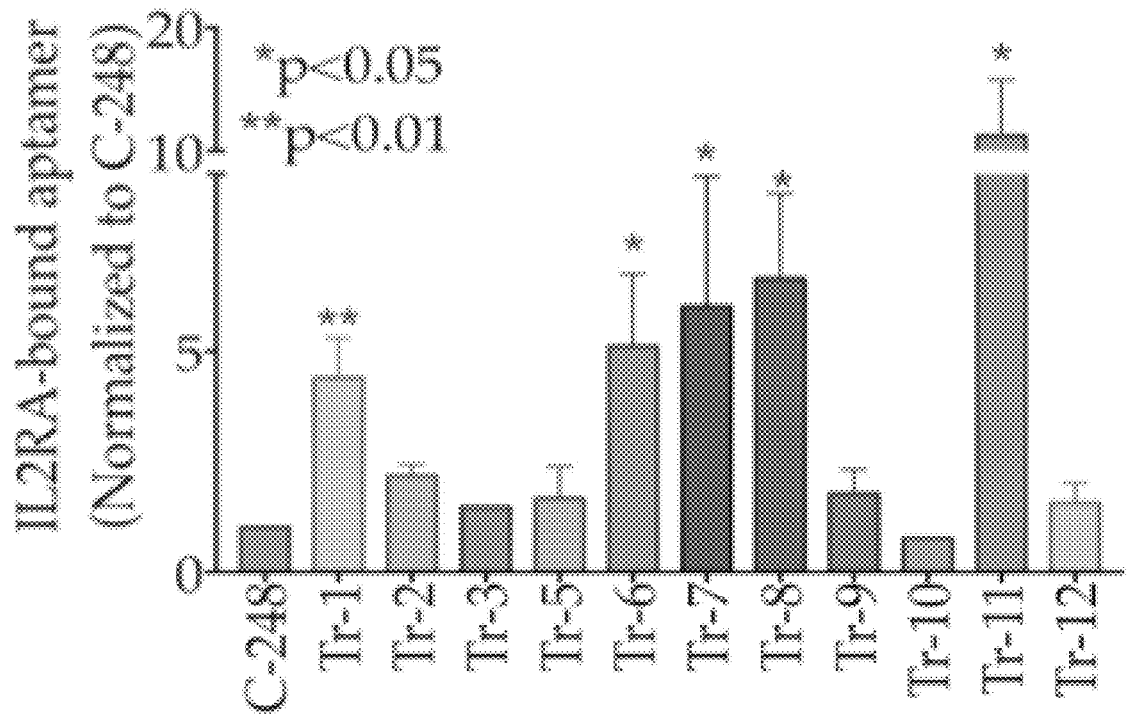

FIG. 15. A subset of Treg-binding aptamers recognize human IL2RA

Figure 16:
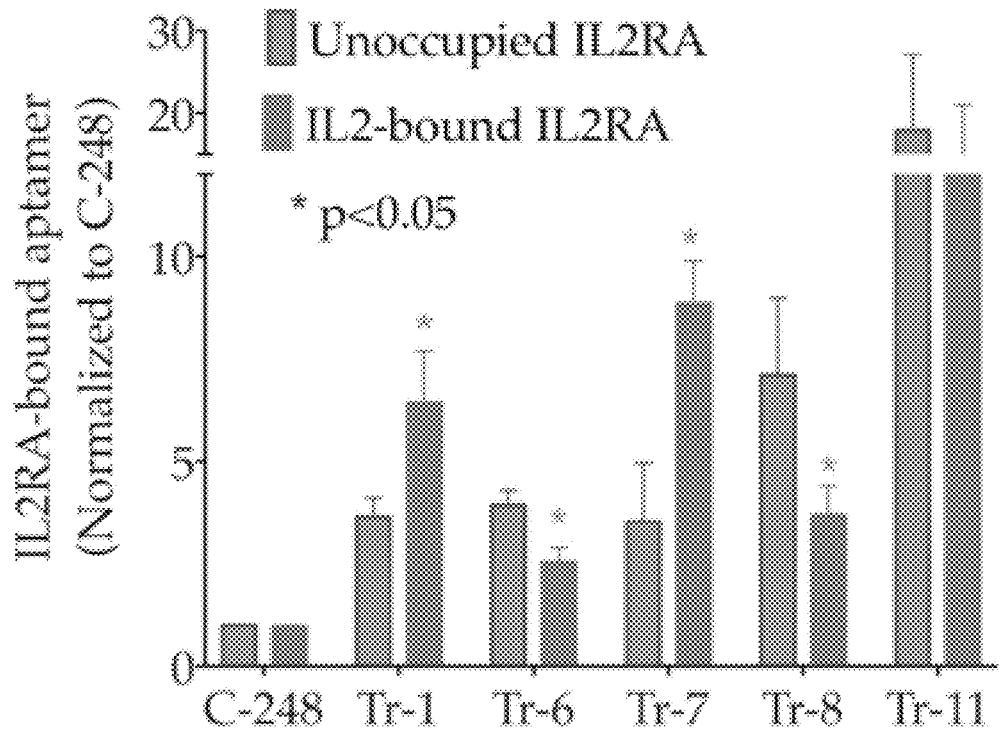

FIG. 16. IL2RA-binding aptamers show differential binding to unoccupied vs IL2-occupied IL2RA.

DETAILED DESCRIPTION

Introduction

Molecular complexes, including those that form between ligands and receptors, heterodimeric and other multimeric molecules, play a central role in mediating a broad range of biological processes. One example is regulation of immune cells as initiated by the interaction of interleukin-2 (IL2) with its alpha receptor subunit, IL2RA (CD25) that leads to recruitment of additional receptor subunits and mediation of activation signals (*Nat Rev Immunol. 2006 August; 6(8): 595-601). Agents that block such interactions have been explored as therapeutics (*Cancer Res. 2015 Feb. 1; 75(3): 497-507). Numerous studies have illustrated the importance of IL2-CD25 complexes on the immune response in a variety of diseases including cancer (*Clin Cancer Res. 2008 Jun. 15; 14(12):3706-15; *Immunity. 2017 Apr. 18; 46(4):577-586; *Immunity. 2010 Aug. 27; 33(2):153-65; *Int J Biomed Sci. 2011 September; 7(3):181-90). Measurement of the individual molecules involved in these interactions, e.g. IL2 or CD25, has been used as a measure of immune cell activation in a variety of settings (*Clin Cancer Res. 2004 Aug. 15; 10(16):5587-94; *J Pediatr Hematol Oncol. 2010 August; 32(6):462-71; *Arq Bras Oftalmol. 2010 September-October; 73(5):443-6; *Iran Red Crescent Med J. 2014 Nov. 17; 16(11):e5410; *Curr Opin Immunol. 2016 August; 41:23-31). Most such studies probe with either monoclonal antibodies or labeled ligand that recognize both the unoccupied receptors as well as receptors occupied by ligand. The ability to directly identify and quantify complexes such as the IL2-CD25 complex, as opposed to assessing its individual components, could provide an additional and valuable tool for assessing the presence or absence of such complexes in tissues or fluids and in targeting those complexes in diseases.

Nucleic acid aptamers are short oligonucleotides that recognize target antigens in a manner analogous to antibodies (*Nat Rev Drug Discov. 2017 June; 16(6):440). The specificity of aptamers, including RNA aptamers, is, in part, based on their nucleotide sequence, which determines their secondary and tertiary structures (*Nat Rev Drug Discov. 2017 June; 16(6):440). RNA aptamers bind to targets via structural complementarity and through forces, including van der Waals forces, hydrogen bonding and electrostatic interaction, and can have affinities similar to those of antibodies (*Molecules. 2015 Jun. 30; 20(7):11959-80).

Generally, RNA aptamers are generated by a process called SELEX (Systematic Evolution of Ligand by EXponential enrichment) that involves sequential enrichment of a diverse RNA library against known or unknown protein or cellular targets until high-affinity binders are selected (*Biomol Eng. 2007 October; 24(4):381-403). SELEX is generally done using the native primary target, i.e. it does not require antigen processing and presentation (*Nat Rev Drug Discov. 2010 July; 9(7):537-50). Thus, RNA aptamers can be developed against target antigens that are not easily targeted by antibodies such as self-antigens, molecular complexes or antigens that are altered with processing and presentation. The nucleic acid nature of RNA aptamers allows them to be sequenced, synthesized, multiplied and modified easily. RNA aptamers, such as VEGF-binding aptamers, can be effective therapeutics (Nat Rev Drug Discov. 2006 February; 5(2):123-32; *Clin Ophthalmol. 2007 December; 1(4):393-402) although their therapeutic utility has been limited by their short half-life in vivo, which is not a huge issue when using RNA aptamers as in vitro diagnostic agents.

Aptamers

Aptamers are single stranded oligonucleotides that can naturally fold into different 3-dimensional structures, which have the capability of binding specifically to biosurfaces, a target compound or a moiety. The term "conformational change" refers to the process by which a nucleic acid, such as an aptamer, adopts a different secondary or tertiary structure. The term "fold" may be substituted for conformational change.

Aptamers have advantages over more traditional affinity molecules such as antibodies in that they are very stable, can be easily synthesized, and can be chemically manipulated with relative ease. Aptamer synthesis is potentially far cheaper and reproducible than antibody production. Aptamers are produced by solid phase chemical synthesis, an accurate and reproducible process with consistency among production batches. An aptamer can be produced in large quantities by polymerase chain reaction (PCR) and once the sequence is known, can be assembled from individual naturally occurring nucleotides and/or synthetic nucleotides. Aptamers can be stored stably at room temperature, and, if denatured, aptamers can easily be renatured, a feature not shared by antibodies. Furthermore, aptamers have the potential to measure concentrations of ligand in orders of magnitude lower (parts per trillion or even quadrillion) than antibody-based diagnostic tests. These characteristics of aptamers make them attractive for diagnostic applications.

Aptamers are typically oligonucleotides that may be single stranded oligodeoxynucleotides, oligoribonucleotides, or modified oligodeoxynucleotide or oligoribonucleotides. The term "modified" encompasses nucleotides with a covalently modified base and/or sugar. For example, modified nucleotides include nucleotides having sugars which are covalently attached to low molecular weight organic groups other than a hydroxyl group at the 3' position and other than a phosphate group at the 5' position. Thus modified nucleotides may also include 2' substituted sugars such as 2'-O-methyl-; 2'-O-Amino; 2'-O-alkyl; 2'-O-allyl; 2'-S-alkyl; 2'-S-allyl; 2'-fluoro-; 2'-halo or 2-azido-ribose, carbocyclic sugar analogues a-anomeric sugars; epimeric sugars such as arabinose, xyloses or lyxoses, pyranose sugars, furanose sugars, and sedoheptulose.

Modified nucleotides are known in the art and include, by example and not by way of limitation, alkylated purines and/or pyrimidines; acylated purines and/or pyrimidines; or other heterocycles. These classes of pyrimidines and purines are known in the art and include, pseudoisocytosine; N4, N4-ethanocytosine; 8-hydroxy-N6-methyladenine; 4-acetylcytosine, 5-(carboxyhydroxylmethyl) uracil; 5-fluorouracil; 5-bromouracil; 5-carboxymethylaminomethyl-2-thiouracil; 5-carboxymethylaminomethyl uracil; dihydrouracil; inosine; N6-isopentyl-adenine; 1-methyladenine; 1-methylpseudouracil; 1-methylguanine; 2,2-dimethylguanine; 2-methyladenine; 2-methylguanine; 3-methyl cytosine; 5-methylcytosine; N6-methyladenine; 7-methylguanine; 5-methylaminomethyl uracil; 5-methoxy amino methyl-2-thiouracil; β-D-mannosylqueosine; 5-methoxycarbonylmethyluracil; 5-methoxyuracil; 2-methylthio-N6-isopentenyladenine; uracil-5-oxyacetic acid methyl ester; pseuouracil; 2-thiocytosine; 5-methyl-2 thiouracil, 2-thiouracil; 4-thiouracil; 5-methyluracil; N-uracil-5-oxyacetic acid methylester; uracil 5-oxyacetic acid; queosine; 2-thiocytosine; 5-propyluracil; 5-propyl cytosine; 5-ethyluracil; 5-ethylcytosine; 5-butyluracil; 5-pentyluracil; 5-pentylcytosine; and 2,6,-diaminopurine; methylpsuedouracil; 1-methylguanine; 1-methylcytosine.

The aptamers can be synthesized using conventional phosphodiester linked nucleotides and synthesized using standard solid or solution phase synthesis techniques which are known in the art. Linkages between nucleotides may use alternative linking molecules. For example, linking groups of the formula P(O)S, (thioate); P(S)S, (dithioate); P(O)NR'2; P(O)R'; P(O)OR6; CO; or CONR'2 wherein R is H (or a salt) or alkyl (1-12C) and R6 is alkyl (1-9C) is joined to adjacent nucleotides through —O— or —S—.

In certain embodiments of the present invention, the aptamer is specific for regulatory T cells. In certain embodiments, additional modifications are made to the aptamer. Additional modifications to the aptamer include 2'O-methyl modification of the pyrimidines. In other embodiments, all of the nucleotides in the aptamer are 2'O-methyl modified. Alternatively, the pyrimidines, or all the nucleotides, may be modified with 2'fluoros (both pyrimidines and purines). Additional modifications to the nucleotides in the aptamer include large molecular weight conjugates like PEGylation, agarose, lipid-based modifications (e.g., cholesterol or liposomes) or nanoparticles (e.g., PLGA, PEI or chitosan). The large molecular weight conjugates can improve the pharmacokinetic/dynamic profile of the chimera.

Generation of Aptamers

Aptamers are high affinity single-stranded nucleic acid ligands which can be isolated from combinatorial libraries through an iterative process of in vitro selection known as SELEX (Systemic Evolution of Ligands by Exponential enrichment). Aptamers exhibit specificity and affinity comparable to or exceeding that of antibodies, and can be generated against most targets. Unlike antibodies, aptamers can be synthesized in a chemical process and hence offer significant advantages in terms of reduced production cost and much simpler regulatory approval process. Also, aptamers are not expected to exhibit significant immunogenicity in vivo.

Aptamers specific for a given biomolecule can be identified using techniques known in the art. See, e.g., PCT Publication No. WO 92/14843; PCT Publication No. WO 91/19813; PCT Publication No. 92/05285; and Nature. 1990 Aug. 30; 346(6287):818-22. Briefly, these techniques typically involve the binding of the molecular target with a random mixture of oligonucleotides. The aptamer-molecular target complex is separated from the unbound oligonucleotides. The aptamer is recovered from the separated complex and amplified. This cycle is repeated to identify those aptamer sequences with the highest affinity for the molecular target.

The SELEX process is a method for the in vitro evolution of nucleic acid molecules with highly specific binding to target molecules and is described in, e.g., U.S. Pat. No. 5,270,163 (see also WO 91/19813) entitled "Nucleic Acid Ligands". Each SELEX-identified nucleic acid ligand is a specific ligand of a given target compound or molecule. The SELEX process is based on the unique insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets.

SELEX relies as a starting point upon a large library of single stranded oligonucleotides comprising randomized sequences derived from chemical synthesis on a standard DNA synthesizer. The oligonucleotides can be modified or unmodified DNA, RNA or DNA/RNA hybrids. In some embodiments, the pool comprises 100% random or partially random oligonucleotides. In other embodiments, the pool comprises random or partially random oligonucleotides containing at least one fixed sequence and/or conserved sequence incorporated within randomized sequence. In other embodiments, the pool comprises random or partially random oligonucleotides containing at least one fixed sequence and/or conserved sequence at its 5' and/or 3' end which may comprise a sequence shared by all the molecules of the oligonucleotide pool. Fixed sequences are sequences common to oligonucleotides in the pool which are incorporated for a pre-selected purpose such as, CpG motifs, hybridization sites for PCR primers, promoter sequences for RNA polymerases (e.g., T3, T4, T7, and SP6), restriction sites, or homopolymeric sequences, such as poly A or poly T tracts, catalytic cores, sites for selective binding to affinity columns, and other sequences to facilitate cloning and/or sequencing of an oligonucleotide of interest. Conserved sequences are sequences, other than the previously described fixed sequences, shared by a number of aptamers that bind to the same target.

The oligonucleotides of the pool can include a randomized sequence portion as well as fixed sequences necessary for efficient amplification. Typically the oligonucleotides of the starting pool contain fixed 5' and 3' terminal sequences which flank an internal region of random nucleotides. The randomized nucleotides can be produced in a number of ways including chemical synthesis and size selection from randomly cleaved cellular nucleic acids. Sequence variation in test nucleic acids can also be introduced or increased by mutagenesis before or during the selection/amplification iterations.

The random sequence portion of the oligonucleotide can be of any length and can comprise ribonucleotides and/or deoxyribonucleotides and can include modified or non-natural nucleotides or nucleotide analogs. See, e.g., U.S. Pat. Nos. 5,958,691; 5,660,985; 5,958,691; 5,698,687; 5,817,635; 5,672,695, and PCT Publication WO 92/07065. Random oligonucleotides can be synthesized from phosphodiester-linked nucleotides using solid phase oligonucleotide synthesis techniques well known in the art. See, e.g Nucleic Acids Res. 1986 Jul. 11; 14(13):5399-407 and Tetrahedron Lett. 1986; 27(46):5575-5578. Random oligonucleotides can also be synthesized using solution phase methods such as triester synthesis methods. See, e.g., Nucleic Acids Res. 1977 August; 4(8): 2757-2765 and Tetrahedron Lett. 1978; 19(28):2449-2452. Sufficiently large regions of random sequence in the sequence design increases the likelihood that each synthesized molecule is likely to represent a unique sequence.

The starting library of oligonucleotides may be generated by automated chemical synthesis on a DNA synthesizer. To synthesize randomized sequences, mixtures of all four nucleotides are added at each nucleotide addition step during the synthesis process, allowing for random incorporation of nucleotides. As stated above, in one embodiment, random oligonucleotides comprise entirely random sequences; however, in other embodiments, random oligonucleotides can comprise stretches of nonrandom or partially random sequences. Partially random sequences can be created by adding the four nucleotides in different molar ratios at each addition step.

The starting library of oligonucleotides may be either RNA or DNA. In those instances where an RNA library is to be used as the starting library it is typically generated by transcribing a DNA library in vitro using T7 RNA polymerase or modified T7 RNA polymerases and then purifying the transcribed products. The RNA or DNA library is then mixed with the target under conditions favorable for binding and subjected to step-wise iterations of binding, partitioning and amplification, using the same general selection scheme, to achieve virtually any desired criterion of binding affinity and selectivity. The target can be molecules of a certain type or types, cells of a certain type or types or any other target or targets of a certain type or types. The identity of the type or types of the molecules, cells, or other targets can be known, suspected, or unknown. More specifically, starting with a mixture containing the starting pool of nucleic acids, the SELEX method includes steps of: (a) contacting the mixture with the target under conditions favorable for binding; (b) partitioning unbound nucleic acids from those nucleic acids which have bound specifically to target molecules; (c) dissociating the nucleic acid-target complexes; (d) amplifying the nucleic acids dissociated from the nucleic acid-target complexes to yield a ligand-enriched mixture of nucleic acids; and (e) reiterating the steps of binding, partitioning, dissociating and amplifying through as many cycles as desired to yield highly specific, high affinity nucleic acid ligands to the target molecule. In those instances where RNA aptamers are being selected, the SELEX method further comprises the steps of: (i) reverse transcribing the nucleic acids dissociated from the nucleic acid-target complexes before amplification in step (d); and (ii) transcribing the amplified nucleic acids from step (d) before restarting the process.

Within a nucleic acid mixture containing a large number of possible sequences and structures, there is a wide range of binding affinities for a given target. Those which have the higher affinity constants for the target are most likely to bind to the target. After partitioning, dissociation and amplification, a second nucleic acid mixture is generated, enriched for the higher binding affinity candidates. Additional rounds of selection progressively favor the best ligands until the resulting nucleic acid mixture is predominantly composed of only one or a few sequences. These can then be cloned, sequenced and individually tested for binding affinity as pure ligands or aptamers.

Cycles of selection and amplification are repeated until a desired goal is achieved. In the most general case, selection/amplification is continued until no significant improvement in binding strength is achieved on repetition of the cycle. Generally, nucleic acid aptamer molecules are selected in a 5 to 20 cycle procedure. In one embodiment, heterogeneity is introduced only in the initial selection stages and does not occur throughout the replicating process. In many cases, it is not necessarily desirable to perform the iterative steps of SELEX until a single nucleic acid ligand is identified. The target-specific nucleic acid ligand solution may include a family of nucleic acid structures or motifs that have a number of conserved sequences and a number of sequences which can be substituted or added without significantly affecting the affinity of the nucleic acid ligands to the target. By terminating the SELEX process prior to completion, it is possible to determine the sequence of a number of members of the nucleic acid ligand solution family.

Counter-SELEX is a method for improving the specificity of nucleic acid ligands to a target molecule by eliminating nucleic acid ligand sequences with cross-reactivity to one or more non-target molecules. Counter-SELEX is comprised of the steps of: (a) preparing a candidate mixture of nucleic acids; (b) contacting the increased affinity nucleic acids with the one or more non-target molecules such that nucleic acid ligands that bind the non-target molecule(s) are removed; (c) discarding the nucleic acids that bind the non-targets from the candidate mixture; (c) contacting the remaining candidate mixture with the target, wherein nucleic acids having an increased affinity to the target relative to the candidate mixture may be partitioned from the remainder of the candidate mixture; (d) partitioning the increased affinity nucleic acids from the remainder of the candidate mixture; (e) dissociating the increased affinity nucleic acids from the target; and (f) amplifying the nucleic acids with specific affinity only to the target molecule to yield a mixture of nucleic acids enriched for nucleic acid sequences with a relatively higher affinity and specificity for binding to the target molecule. As described above for SELEX, cycles of selection and amplification are repeated as necessary until a desired goal is achieved.

One potential problem encountered in the use of nucleic acids as therapeutics is that oligonucleotides in their phosphodiester form may be quickly degraded in body fluids by intracellular and extracellular enzymes such as endonucleases and exonuclease before the desired effect is manifest. The SELEX method thus encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. One of ordinary skill in the art will appreciate that one or more of the modifications described herein can be included in the desired aptamer and that the modified aptamer can be tested for binding using any method known in the art. For example, oligonucleotides can contain nucleotide derivatives chemically modified at the 2' position of ribose, 5' position of pyrimidines, and 8' position of purines, 2'-modified pyrimidines, and nucleotides modified with 2'-amino (2'-NH2), T-fluoro (2'-F), and/or 2'-O-methyl (2'-OMe) substituents.

In some embodiments, one or more modifications of the aptamers contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Modifications to generate oligonucleotide populations which are resistant to nucleases can also include one or more substitute internucleotide linkages, altered sugars, altered bases, or combinations thereof. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, and unusual base-pairing combinations such as the isobases—isocytidine and isoguanosine. Modifications can also include 3' and 5' modifications such as capping.

Pre-SELEX process modifications or those made by incorporation into the SELEX process can, for example, yield nucleic acid ligands with both specificity for their SELEX target and improved stability, e.g., in vivo stability. Post-SELEX process modifications made to nucleic acid ligands can, for example, result in improved stability, e.g., in vivo stability without adversely affecting the binding capacity of the nucleic acid ligand. The SELEX method encompasses combining selected oligonucleotides with other selected oligonucleotides and non-oligonucleotide functional units as described in U.S. Pat. Nos. 5,637,459 and 5,683,867. The SELEX method further encompasses combining selected nucleic acid ligands with lipophilic or non-immunogenic high molecular weight compounds in a diagnostic or therapeutic complex, as described, e.g., in U.S. Pat. Nos. 6,011,020, 6,051,698, and PCT Publication No. WO 98/18480. These patents and applications teach the combination of a broad array of shapes and other properties, with the efficient amplification and replication properties of oligonucleotides, and with the desirable properties of other molecules.

The aptamers with specificity and binding affinity to the target(s) of the present invention are typically selected by the SELEX process as described herein. As part of the SELEX process, the sequences selected to bind to the target can then optionally be minimized to determine the minimal sequence having the desired binding affinity. The selected sequences and/or the minimized sequences are optionally optimized by performing random or directed mutagenesis of the sequence to increase binding affinity or alternatively to determine which positions in the sequence are essential for binding activity. Additionally, selections can be performed with sequences incorporating modified nucleotides to stabilize the aptamer molecules against degradation in vivo.

Molecules Linked to Aptamers

The aptamers of the present invention can be operably linked to one or more entities. In certain embodiments, the entity is a fluorescent tag, affinity tag, a protein, a solid substrate, a cell surface, or a cellular component. In certain embodiments, the cellular component is a cell wall or cell membrane. In certain embodiments, the solid substrate is a component of polysaccharide, silica, cellulose, cellulose acetate, nitrocellulose, nylon, polyester, polyethersulfone, polyolefin, or polyvinylidene fluoride, or combinations thereof. In certain embodiments, the solid substrate is a filter, magnetic bead, metal oxide, latex particle, microtiter plate, polystyrene bead, or medical device. In certain embodiments the aptamer is linked to a solid substrate, such as agarose, sepharose, or nanoparticles. In certain embodiments, the solid substrate is a stent or other medical device, filter, magnetic bead, metal oxide, latex particle, microtiter plates, or polystyrene bead.

In certain embodiments, the aptamer is linked to the entity by means of a linker. In certain embodiments, the linker is a binding pair. In certain embodiments, the "binding pair" refers to two molecules which interact with each other through any of a variety of molecular forces including, for example, ionic, covalent, hydrophobic, van der Waals, and hydrogen bonding, so that the pair have the property of binding specifically to each other. "Specific" binding means that the binding pair members exhibit binding to each other under conditions where they do not bind to one of any number of other molecules. Examples of binding pairs are biotin-avidin, hormone-receptor, receptor-ligand, enzyme-substrate, IgG-protein A, antigen-antibody, and the like. In certain embodiments, a first member of the binding pair comprises avidin or streptavidin and a second member of the binding pair comprises biotin. In certain embodiments, the aptamer is linked to the entity by means of a covalent bond.

The entity, for example, may additionally or alternatively, be a detection means. A number of "molecular beacons" (such as fluorescence compounds) can be attached to aptamers to provide a means for signaling the presence of and/or quantifying a target chemical or biological agent. Other exemplary detection labels that could be attached to the aptamers include biotin, any fluorescent dye or tracer, amine modification, horseradish peroxidase, alkaline phosphatase, etc.

In certain embodiments, the aptamer is operably linked to a detection means and to a solid substrate. For example, the aptamer may be linked to a fluorescent dye and to a magnetic bead.

Small molecules can be linked to the aptamer. These include but are not limited to siRNA sequences, miRNAs, small molecule inhibitors, cytotoxic chemicals, chelators for housing radionuclides (for diagnostic/imaging applications as well as development of targeted radiotherapies, see, e.g., Bioorg Med Chem. 2011 Jul. 1; 19(13):4080-90), nanoparticles containing all of the above plus DNA vectors and/or mRNA sequences or other types of small molecule, depending on the use of the ligand as a diagnostic agent or as a therapeutic agent. In certain embodiments, the small molecule is a molecule capable of modulating cell activity, including but not limited to biologic and pharmacologic inhibitors/agonists, siRNA, or miRNA. In certain embodiments, the small molecules are biologic or pharmacologic agents that can influence Treg activity.

Chemistries that can be used to link molecules to the aptamer are known in the art, such as disulfide linkages, amino linkages, covalent linkages, etc.

Amplification Methods

In one embodiment of the present invention, the method involves the amplification of selected RNAs. "Amplifying" utilizes methods such as the polymerase chain reaction (PCR), ligation amplification (or ligase chain reaction, LCR), strand displacement amplification, nucleic acid sequence-based amplification, and amplification methods based on the use of Q-beta replicase. These methods are well known and widely practiced in the art. Reagents and hardware for conducting PCR are commercially available. One of ordinary skill in the art will appreciate that in some methods of amplification at least one type of aptamer can be immobilized on a solid surface.

According to the methods of the present invention, the amplification may be carried out by any means known to the art. Examples of suitable amplification techniques include, but are not limited to, polymerase chain reaction (including, for RNA amplification, reverse-transcriptase polymerase chain reaction), ligase chain reaction, strand displacement amplification, transcription-based amplification, self-sustained sequence replication (or "3 SR"), the Qβ replicase system, nucleic acid sequence-based amplification (or "NASBA"), the repair chain reaction (or "RCR"), and boomerang DNA amplification (or "BDA").

The nucleotides incorporated into the amplification product may be natural or modified nucleotides (modified before or after amplification), and the nucleotides may be selected to optimize subsequent electrochemical detection steps.

Polymerase chain reaction (PCR) may be carried out in accordance with known techniques. See, e.g., U.S. Pat. Nos. 4,683,195; 4,683,202; 4,800,159; and 4,965,188. In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized that is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps are cyclically repeated until the desired degree of amplification is obtained. Detection of the amplified sequence may be carried out by adding to the reaction product an oligonucleotide probe capable of hybridizing to the reaction product (e.g., an oligonucleotide probe of the present invention), the probe carrying a detectable label, and then detecting the label in accordance with known techniques. Where the nucleic acid to be amplified is RNA, amplification may be carried out by initial conversion to DNA by reverse transcriptase in accordance with known techniques.

Strand displacement amplification (SDA) may be carried out in accordance with known techniques. For example, SDA may be carried out with a single amplification primer or a pair of amplification primers, with exponential amplification being achieved with the latter. In general, SDA amplification primers comprise, in the 5' to 3' direction, a flanking sequence (the DNA sequence of which is noncritical), a restriction site for the restriction enzyme employed in the reaction, and an oligonucleotide sequence (e.g., an oligonucleotide probe of the present invention) that hybridizes to the target sequence to be amplified and/or detected. The flanking sequence, which serves to facilitate binding of the restriction enzyme to the recognition site and provides a DNA polymerase priming site after the restriction site has been nicked, is about 15 to 20 nucleotides in length in one embodiment. The restriction site is functional in the SDA reaction. The oligonucleotide probe portion is about 13 to 15 nucleotides in length in one embodiment of the invention.

Ligase chain reaction (LCR) is also carried out in accordance with known techniques. In general, the reaction is carried out with two pairs of oligonucleotide probes: one pair binds to one strand of the sequence to be detected; the other pair binds to the other strand of the sequence to be detected. Each pair together completely overlaps the strand to which it corresponds. The reaction is carried out by, first, denaturing (e.g., separating) the strands of the sequence to be detected, then reacting the strands with the two pairs of oligonucleotide probes in the presence of a heat stable ligase so that each pair of oligonucleotide probes is ligated together, then separating the reaction product, and then cyclically repeating the process until the sequence has been amplified to the desired degree. Detection may then be carried out in like manner as described above with respect to PCR.

For the diagnostic and research tool methods described herein the aptamers that specifically bind to complexes can be included in the sample that is to be tested and the aptamers that specifically bind to one or more members of a complex can also be included in the same sample. In instances where the aptamers with different selectivity are introduced into the same sample, the aptamers can be associated with distinct tags. The distinct tags can be used to quantify the amount of each aptamer that is bound to the complex or to an unbound member of the complex. Tags, such as fluorescent moieties are well known in the art. Similarly, a sample can be divided and aptamers with various specific binding activities can be introduced singly into the sample. One of ordinary skill in the art will appreciate that there are number of variations that can be made to methods of using the disclosed aptamers for diagnostic and research purposes.

The sample may be contacted with the aptamer in any suitable manner known to those ordinarily skilled in the art. For example, the sample may be solubilized in solution, and contacted with the aptamer by solubilizing the aptamer in solution with the sample under conditions that permit binding. Suitable conditions are well known to those ordinarily skilled in the art. Alternatively, the sample may be solubilized in solution with the aptamer immobilized on a solid support, whereby the sample may be contacted with the aptamer by immersing the solid support having the aptamer immobilized thereon in the solution containing the sample.

Diseases and Conditions Amendable to the Methods of the Invention

In certain embodiments of the present invention, a mammalian recipient to an embodiment of the invention has a condition that is amenable to detection or therapy using the aptamers of the present invention. For example, the aptamers described herein can be used to modulate diseases that are preferentially treated by targeting cells where a complex is the target. An example of such a disease is wherein a given endogenous population of cells is hyperactive and the aptamers of the invention selectively target the subset of cells that have receptors bound to ligands.

In certain embodiments, the mammal has or is suspected of having cancer. In certain embodiments, the cancer is suspected to be amenable to treatment with immunotherapy. These diseases include but are not necessary limited to B cell lymphomas and breast cancer. In certain embodiments, the efficacy of immunotherapy is suspected to be amenable to improvement by modulation of regulatory T cells.

In certain embodiments, the mammal has or is suspected of having autoimmune disease. In certain embodiments, the autoimmune disease is suspected to be amenable to treatment modulation of regulatory T cells. These diseases include but are not necessary limited to scurfy syndrome and IPEX syndrome.

In certain embodiments, the mammal is at elevated risk or is suspected of being at elevated risk of having rejection of a transplant. Types of transplant include but are not limited to organ, such as kidney, liver, heart, or lung, and tissue, such as skin, bone, or heart valve. In certain embodiments, the transplant rejection is suspected to be amenable to treatment by modulation of regulatory T cells. These diseases include but are not necessary limited to islet transplantation for Type I diabetes or pancreatic transplantation for Type I diabetes.

As used herein, the term "therapeutic molecule" refers to any small molecule that has a beneficial effect on the recipient. Thus, "therapeutic molecule" embraces both therapeutic and prophylactic small molecules.

Dosages, Formulations and Routes of Administration of the Agents of the Invention Aptamers designed to be therapeutic (agents) can be administered so as to result in a reduction of at least one symptom associated with a disease. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems, which are well known to the art.

Certain embodiments of the present invention envision treating a disease, for example, cancer, autoimmune disease, transplant rejection disease (e.g. host-versus-graft disease), or other diseases, in a mammal by the administration of an agent, e.g., a nucleic acid composition, an expression vector, or a viral particle of the invention. Administration of the therapeutic agents in accordance with the present invention may be continuous or intermittent, depending, for example, upon the recipient's physiological condition, whether the purpose of the administration is therapeutic or prophylactic, and other factors known to ordinarily skilled practitioners. The administration of the agents of the invention may be essentially continuous over a preselected period of time or may be in a series of spaced doses. Both local and systemic administration is contemplated.

One or more suitable unit dosage forms having the therapeutic agent(s) of the invention, which, as discussed below, may optionally be formulated for sustained release (for example using microencapsulation), can be administered by a variety of routes including parenteral, including by intravenous and intramuscular routes, as well as by direct injection into the diseased tissue. In another example, the therapeutic agent may be introduced intramuscularly for viruses that traffic back to affected neurons from muscle, such as AAV, lentivirus and adenovirus. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. Pharmaceutically acceptable, as used herein, refers to a carrier, diluent, excipient, and/or salt that is compatible with the other ingredients of the formulation, and is not deleterious to the recipient thereof. The active ingredient for administration may be present as a powder or as granules, as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for example by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions such as phosphate buffered saline solutions pH 7.0-8.0, saline solutions, and water.

Methods of Detection for Research or Diagnostics

As described herein, in some embodiments the aptamers are used to determine the relative amount of bound and unbound members of a complex. These methods involve using at least two aptamers with different specificity. One aptamer preferentially binds to the complex and the second aptamer preferentially binds to a member of the complex when that member is not bound to the complex. By measuring the amount of each aptamer that binds in a sample a determination of the relative amount of complexes and unbound members can be made. This information is useful for determining complex formation under various test conditions, such as at various acidity levels, temperatures, relative concentrations, as well as under physiological conditions such as in the context of saliva, blood, tissue samples, etc. In some instances, the amount of bound and unbound members of a complex can be determined by alternatively using a specific binding agent such as an antibody that specifically binds to the unbound member and detecting the antibody.

In additional embodiments the aptamers described herein can be used to mark cells or tissues using standard techniques that are familiar to one ordinarily skilled in the art (PLoS One. 2017 Feb. 24; 12(2):e0173050; Nucleic Acids Res. 1998 Sep. 1; 26(17):3915-24; Nucleic Acid Ther. 2016 June; 26(3):120-6). The aptamers described herein can be substituted for antibodies in commonly used assays including flow cytometry, fluorescence microscopy and immunohistochemistry.

In embodiments of the present invention, molecular beacons are attached to aptamers to provide a means for signaling and detecting target complexes and unbound members of complexes. Molecular beacons, for example, can employ fluorescence resonance energy transfer-based methods to provide fluorescence signals in the presence of a particular analyte/biomarker of interest (see J Am Chem Soc. 2001 May 30; 123(21):4928-31). The aptamer acts as a sensor to detect the presence of a specific target analyte/biomarker. Upon detection of the analyte/biomarker, the aptamer communicates with a molecular beacon to generate a detectable signal.

Similarly, amplifying fluorescent polymers (AFPs) can be utilized in the present invention. An AFP is a polymer containing several chromophores that are linked together. As opposed to isolated chromophores that require 1:1 interaction with an analyte in conventional fluorescence detection, the fluorescence of many chromophores in an AFP can be influenced by a single molecule. For example, a single binding event to an AFP can quench the fluorescence of many polymer repeat units, resulting in an amplification of the quenching. Quenching is a process which decreases the intensity of the fluorescence emission.

Molecular beacons and AFPs, including their methods for preparation, that can be used in the present invention are described in numerous patents and publications, including U.S. Pat. No. 6,261,783 and Fisher, M. et al., "A Man-Portable Chemical Sniffer Utilizing Novel Fluorescent Polymers for Detection of Ultra-Trace Concentrations of Explosives Emanating from Landmines," Paper from the 4th International Symposium on "Technology and the Mine Problem" held at the Naval Postgraduate School in Monterey, Calif., on Mar. 12-16, 2000, Nomadics, Inc. Staining of tumor samples for Tregs for research or diagnostics Aptamers such as those described herein can be used to image living tissue of humans or mammals in vivo or ex vivo (PLoS One. 2016 Feb. 22; 11(2):e0149387). One of ordinary skill in the art would know to link a molecule that can be visualized to an aptamer described herein. The aptamer can then be contacted to cells suspected to contain a complex of interest. The presence of the aptamer linked to a molecule to be detected and bound to a complex of interest thus shows where the complex of interest is located (Theranostics. 2014 Jul. 19; 4(9):945-52; Osong Public Health Res Perspect. 2012 March; 3(1):48-59).

Methods of Delivering Aptamer-Linked Molecules to Cells

The present invention in certain embodiments provides systems for selectively delivering therapeutic or diagnostic agents to particular organs, tissues, cells, and/or intracellular compartments using an aptamer described herein for targeting. In certain embodiments, therapeutic or diagnostic agents are specifically delivered to diseased organs, tissues, cells, and/or intracellular compartments based on targeting directed by nucleic acid targeting moieties. In certain specific embodiments, therapeutic or diagnostic agents are specifically delivered to T cells or tumors (e.g. malignant tumors or benign tumors).

The aptamers described herein can be delivered to an organism by various means including but not limited to by injection, topically, orally, or by a rinse, such as a rinse of a body cavity during surgery. One of ordinary skill in the art would know of many methods of delivering aptamers to an organism.

Methods of Treatment

In some embodiments, complexes or targeted particles in accordance with the present invention may be used to treat, alleviate, ameliorate, relieve, delay onset of, inhibit progression of, reduce severity of, and/or reduce incidence of one or more symptoms or features of a disease, disorder, and/or condition. In some embodiments, aptamers described herein can be used to treat cancer.

In one aspect of the invention, a method for the treatment of cancer (e.g. a cancer susceptible to treatment by immunotherapy) is provided. In some embodiments, the treatment of cancer comprises administering a therapeutically effective amount of aptamers or aptamers linked to other molecules to a subject in need thereof, in such amounts and for such time as is necessary to achieve the desired result. In certain embodiments of the present invention a "therapeutically effective amount" of an inventive complexes or targeted particle is that amount effective for treating, alleviating, ameliorating, relieving, delaying onset of, inhibiting progression of, reducing severity of, and/or reducing incidence of one or more symptoms or features of cancer.

The present invention provides methods for treating cancer, immune disorders, or other diseases generally comprising targeted delivery of inventive complexes or targeted particles. Such targeted delivery can be useful for delivery of one or more therapeutic agents that are capable of intercalating between the base pairs of a nucleic acid targeting moiety. Alternatively or additionally, such targeted delivery can be useful for co-delivery of multiple therapeutic agents. For example, targeted particles may comprise at least a second therapeutic agent (e.g. one that is useful for treatment and/or diagnosis of cancer) that is encapsulated within the polymeric matrix of a particle.

Methods of Isolating Cells for Treatment

Circulating cells or other types of cells can be isolated from body fluid by adapting commonly used techniques to the use of an aptamer or aptamers described herein. "Circulating cells" includes cells that normally circulate, such as T cells or red blood cells, or they can be cells that do not normally circulate, such as circulating tumor cells. The term "circulating tumor cells" or "CTCs" relates to cells that have detached from a primary tumor or tumor metastases and circulate in the bloodstream. CTCs may constitute seeds for subsequent growth of additional tumors (metastasis) in different tissues. Circulating tumor cells are found in frequencies in the order of 1-10 CTC per mL of whole blood in patients with metastatic disease. Research methods have been developed to isolate circulating cells, CTC, or other cells from body fluid. Several research methods have been described in the art to isolate CTCs, e.g. techniques which exploit the fact that epithelial cells commonly express the cell adhesion protein EpCAM, which is absent in normal blood cells. Immunomagnetic bead-based capture involves treating blood specimens with antibody to EpCAM that has been conjugated with magnetic particles, followed by separation of tagged cells in a magnetic field. The EpCAM antibody can be substituted with an aptamer or aptamers that are described herein. Isolated cells are then stained with antibody to another epithelial marker, cytokeratin, as well as a common leukocyte marker CD45, so as to distinguish rare CTCs from contaminating white blood cells. This robust and semi-automated approach identifies CTCs with an average yield of approximately 1 CTC/mL and a purity of 0.1% (Clin Cancer Res. 2004 Oct. 15; 10(20):6897-6904). This technique can be adapted to use other reagents or to isolate other types of cells, e.g. to use an aptamer described herein that specifically binds the CD25-IL2 complex to isolate regulatory T cells. A second method for isolating CTCs uses a microfluidic-based CTC capture device which involves flowing whole blood through a chamber embedded with 80,000 microposts that have been rendered functional by coating with antibody to EpCAM. This can be adapted by substituting the EpCAM antibody with an aptamer or aptamers described herein. CTCs are then stained with secondary antibodies against either cytokeratin or tissue specific markers, such as PSA in prostate cancer or HER2 in breast cancer and are visualized by automated scanning of microposts in multiple planes along three dimensional coordinates. CTC-chips are able to identifying cytokeratin-positive circulating tumor cells in patients with a median yield of 50 cells/ml and purity ranging from 1-80% (Nature. 2007 Dec. 20; 450 (7173):1235-9). This technique can be adapted to use other reagents or to isolate other types of cells, e.g. to use an aptamer described herein that specifically binds the CD25-IL2 complex to isolate regulatory T cells. Another possibility for isolating CTCs is using the CellSearch™ Circulating Tumor Cell (CTC) Test from Veridex, LLC (Raritan, N.J.) which captures, identifies, and counts CTCs in a tube of blood. The CellSearch™ system is a U.S. Food and Drug Administration (FDA) approved methodology for enumeration of CTC in whole blood which is based on a combination of immunomagnetic labeling and automated digital microscopy. There are other methods for isolating circulating cells, CTCs, or other cells from body fluid described in the literature all of which can be used in conjunction with the present invention.

Cells can be isolated from a patient or donor human or mammal for chemical treatment and transplantation to treat disease or as a research tool. Using the aptamers described herein, one of ordinary skill in the art could isolate cells suspected to contain complexes of interest as described herein. One of ordinary skill in the art could then use widely known chemical treatment techniques to alter the biology of the cells suspected to contain the complexes of interest (Methods Mol Biol. 2016; 1434:169-83). Treated cells can then be transplanted into a patient or recipient human or mammal (J Clin Oncol. 2015 Feb. 20; 33(6):540-9; Lancet. 2015 Feb. 7; 385(9967):517-28).

Cells can be isolated from a patient or donor human or mammal for genome editing and transplantation to treat disease or as a research tool. Using the aptamers described herein, one of ordinary skill in the art could isolate cells suspected to contain complexes of interest as described herein. One of ordinary skill in the art could then use widely known genome editing techniques to edit the genomes of the cells suspected to contain the complexes of interest (Nat Med. 2016 September; 22(9):987-90; Proc Natl Acad Sci USA. 2017 Feb. 14; 114(7):1660-1665; N Engl J Med. 2014 Oct. 16; 371(16):1507-17; J Clin Oncol. 2015 Feb. 20; 33(6):540-9; Lancet. 2015 Feb. 7; 385(9967):517-28). Genome-edited cells can then be transplanted into a patient or recipient human or mammal (J Clin Oncol. 2015 Feb. 20; 33(6):540-9; Lancet. 2015 Feb. 7; 385(9967):517-28).

Tregs are a unique subset of $CD4^+$ T cells responsible for self-tolerance and for the prevention of autoimmune disease (Immunity. 2009 May; 30(5):636-45). Adoptive Treg infusion has been suggested as a potential therapy for the prevention of Graft versus Host Disease (GVHD) following stem cell transplantation, organ allograft rejection, and for the treatment of autoimmune diseases such as type I diabetes and multiple sclerosis (Nat Rev Immunol. 2007 August; 7(8):585-98; Immunity. 2009 May; 30(5):656-65). Adoptive transfer of $Foxp3^+$ Tregs in mouse models has been shown to prevent acute and chronic GVHD without negative effects on the graft versus leukemia response (J Exp Med. 2002 Aug. 5; 196(3):389-99). More recently, a number of groups have reported that co-transfer of expanded Tregs from umbilical cord samples (Blood. 2011 Jan. 20; 117(3):1061-70) or from peripheral blood appears to be both safe (Clin Immunol. 2009 October; 133(1):22-6) and in one study remarkably effective in preventing acute GVHD following stem cell transplantation (Blood. 2011 Apr. 7; 117(14):3921-8).

The present invention in certain embodiments relates to methods for producing a population of cells enriched for Tregs from a patient or other mammal. One of ordinary skill in the art can use methods described herein to use the described aptamer or aptamers to isolate regulatory T cells. One of ordinary skill in the art can then use known techniques to expand the number of Tregs (U.S. Pat. No. 9,481,866; U.S. Ser. No. 14/382,537). The resulting Tregs can then be transplanted back into the patient or other mammal. This method can be used to treat diseases such as graft-versus-host disease, autoimmune diseases, or other diseases.

Method of Modulating Cells for Immunotherapy

Regulatory T cells and other types of cells, for example those listed in Tables 12 and 13, can be targeted for immunotherapy of cancer in humans or mammals. The aptamers described herein can be used to direct treatments to cells suspected to contain complexes of interest, as described in Example 12. Such techniques and other techniques can be used to deliver molecules that influence immune function, such as by inhibiting the activity of Tregs or other types of cells, increasing the activity of Tregs or other types of cells, or causing cytotoxicity to Tregs.

Regulatory T cells or other types of cells, for example those listed in Tables 12 and 13, can be removed or depleted from a human or other mammal for reasons including to influence immunotherapy. For example, removal or depletion of Tregs can be used to increase the efficacy of cancer immunotherapy. Example 12 describes techniques to isolate cells containing complexes of interest using aptamers described herein. Such techniques can be adapted by one of ordinary skill in the art to remove cells from a mixture to the extent that there are few enough of the cells of interest to influence immunotherapy. For example, enough Tregs can be removed from a patient that there is an increased efficacy of other immunotherapy treatment or treatments in the patient.

General Terminology

"Synthetic" aptamers are those prepared by chemical synthesis. The aptamers may also be produced by recombinant nucleic acid methods. "Recombinant nucleic acid molecule" is a combination of nucleic acid sequences that are joined together using recombinant nucleic acid technology and procedures used to join together nucleic acid sequences known in the art.

As used herein, the term "nucleic acid" and "polynucleotide" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides such those that containing the modifications described herein.

The term "nucleotide sequence" refers to a polymer of DNA or RNA which can be single- or double-stranded, optionally containing synthetic, non-natural or altered nucleotide bases capable of incorporation into DNA or RNA polymers. A "nucleic acid fragment" is a portion of a given nucleic acid molecule.

The terms "nucleic acid," "nucleic acid molecule," "nucleic acid fragment," "nucleic acid sequence or segment," or "polynucleotide" may also be used interchangeably with gene, cDNA, DNA and RNA encoded by a gene, e.g., genomic DNA, and even synthetic DNA sequences. The term also includes sequences that include any of the known base analogs of DNA and RNA.

By "fragment" or "portion" is meant a full length or less than full length of the nucleotide sequence.

As used herein, the terms "sequence identity" or "identity" in the context of two nucleic acid sequences make reference to a specified percentage of residues in the two sequences that are the same when aligned by sequence comparison algorithms or by visual inspection.

As used herein, "percentage of sequence identity" means the value determined by comparing two optimally aligned sequences, wherein the portion of the polynucleotide sequence may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 70%, 71%, 72%, 73%, 74%, 75%, 76%, 77%, 78%, or 79%; at least 80%, 81%, 82%, 83%, 84%, 85%, 86%, 87%, 88%, or 89%; at least 90%, 91%, 92%, 93%, or 94%; or even at least 95%, 96%, 97%, 98%, or 99% sequence identity, compared to a reference sequence using one of the alignment programs described using standard parameters.

"Treating" as used herein refers to ameliorating at least one symptom of, curing and/or preventing the development of a disease or a condition.

The terms "protein," "peptide" and "polypeptide" are used interchangeably herein.

A "vector" is defined to include, inter alia, any viral vector, as well as any plasmid, cosmid, phage or binary vector in double or single stranded linear or circular form that may or may not be self-transmissible or mobilizable, and that can transform prokaryotic or eukaryotic host either by integration into the cellular genome or exist extrachromosomally (e.g., autonomous replicating plasmid with an origin of replication).

The term "immunotherapy" relates to a treatment involving activation of a specific immune reaction. In the context of the present invention, terms such as "protect", "prevent", "prophylactic", "preventive", or "protective" relate to the prevention or treatment or both of the occurrence and/or the propagation of a disease in a subject and, in particular, to minimizing the chance that a subject will develop a disease or to delaying the development of a disease. For example, a person at risk for a tumor, as described above, would be a candidate for therapy to prevent a tumor.

The term "molecule" refers to an atom or atoms held together by chemical bonds, including chemical compounds. Chemical bonds include covalent bonds, ionic bonds, metallic bonds, and coordinate covalent bonds. Examples of a molecule include but are not limited to a protein, DNA, RNA, nucleic acids, and certain fluorescent dyes.

The term "pool" refers to a collection of any number of things of a type or types that is separated from other things of the same or different type or types. For example, a collection of polynucleotides can be split into two or more pools of polynucleotides that are separate from each other, in which the sequence or sequences of polynucleotides in a pool may be identical or different from another pool or other pools.

The terms "bind" or "bound" refers to two or more molecules that are in contact through various types of non-covalent interactions that do not involve the sharing of electrons, but rather involve more dispersed variations of electromagnetic interactions between molecules or within a molecule. Examples of such interactions are electrostatic interactions (e.g. ionic bonds, hydrogen bonds and halogen binding), Van der Waals forces (e.g. dipole-dipole, dipole-induced dipole and London dispersion forces), π-effects (e.g. π-π interactions, cation-π and anion-π interactions, and polar-π interactions), and the hydrophobic effect.

The term "complex" refers to two or more molecules that are bound to each other, e.g protein-protein, protein-DNA, and protein-RNA complexes.

The term "endogenous" refers to a molecule or molecules that are normally produced or synthesized within a cells, system, or organism. An endogenous molecule is native to the cell, system, or organism and not heterologous. For example, an endogenous gene is one that naturally occurs within the genomic or mitochondrial-genomic context of the cell, system, or organism.

The term "selective" refers to something that has some degree of specificity for one or more things over one or more other things. For example, an aptamer that is selective can bind preferentially, more stably, more strongly, more quickly, with higher affinity, or with higher avidity or with slower reversal of binding to one or more molecules relative to one or more other molecules.

The term "linked" refers to two or more molecules that associated with each other in such a way so that they stay associated with each other or disassociate with each other as desired to at least a certain extent. Such associations can be covalent or non-covalent binding.

The term "mixture" refers to a collection of things, e.g. molecules, of one or more types.

The term "body fluid" refers to liquids originating from the body of a human or other animal. Body fluids include but are not limited to those that are retained in, excreted from, and secreted from the body. Body fluids include but are not limited to intracellular fluid, extracellular fluid, intravascular fluid, interstitial fluid, lymphatic fluid, transcellular fluid, blood, cerebrospinal fluid, lymph, pericardial fluid, peritoneal fluid, pleural fluid, and urine.

EXAMPLES

The following examples are intended to illustrate various embodiments of the invention. As such, the specific embodiments discussed are not to be construed as limitations on the scope of the invention. It will be apparent to one ordinarily skilled in the art that various equivalents, changes, and modifications may be made without departing from the scope of invention, and it is understood that such equivalent embodiments are to be included herein. For example, although the Examples describe studies related to aptamers that bind CD25 and IL2, one ordinarily skilled in the art would understand that any aptamer may be conjugated to any applicable other molecule based on the methods described below in order to recognize a target complex or complexes or cell or cells. Non-limiting examples of aptamers and other molecules that may be used are described above. Further, all references cited in the disclosure are hereby incorporated by reference in their entirety, as if fully set forth herein.

Example 1

Figure 1:
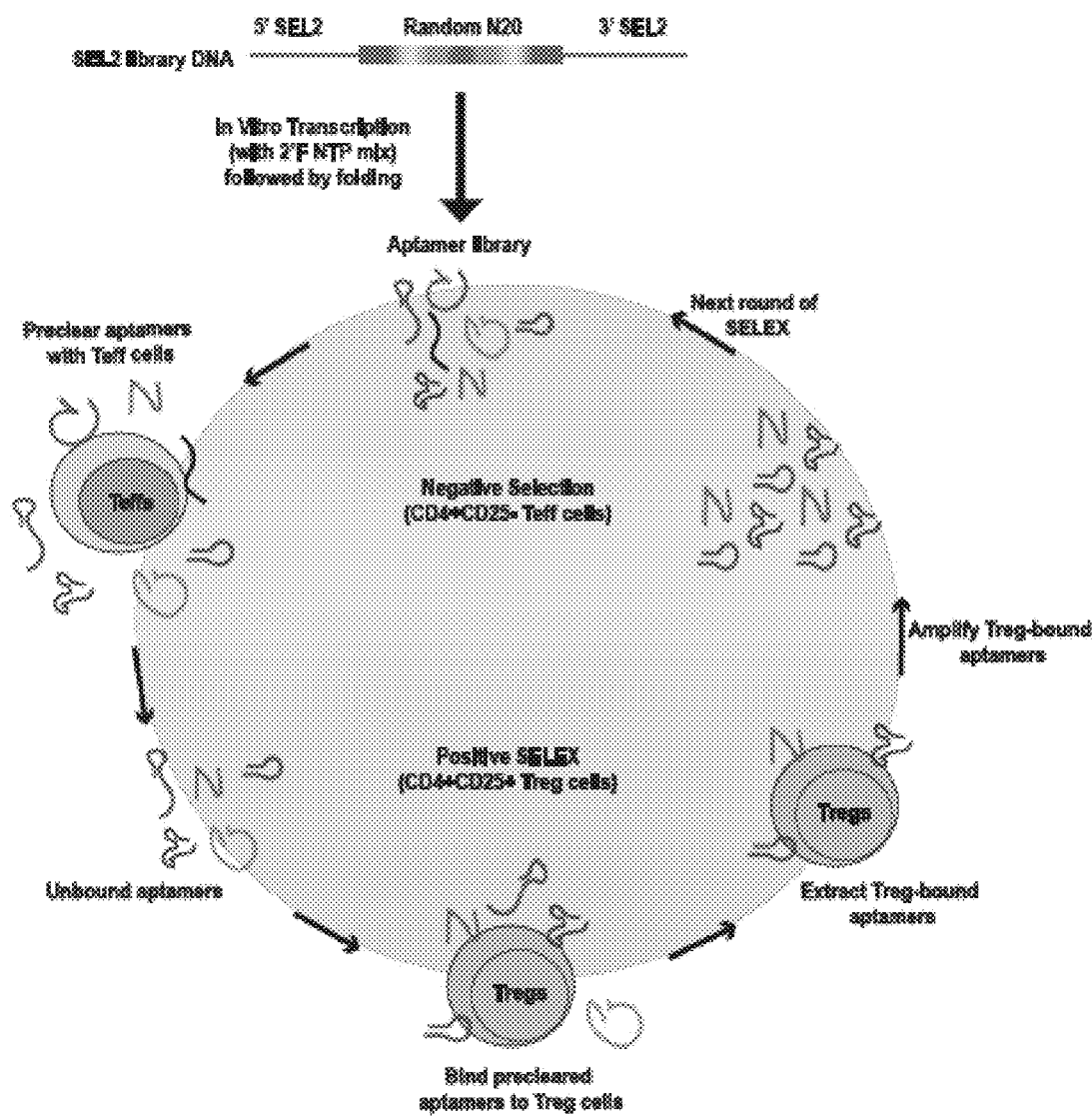
FIG. 1. Schematic representation of enrichment of RNA aptamers that bind regulatory T cells (Tregs). Enrichment of Treg-binding RNA aptamers was performed using a cell-based SELEX approach. SEL2-based library (Nucleic Acid Ther. 2011 August; 21(4):253-63) was synthesized as template DNA (Integrated DNA Technologies, USA) which was transcribed in vitro to generate 2'-fluoro-modified RNA library (also identified as Rd 0). Each round of SELEX consisted of a negative selection step with effector T cells (Teffs) that were both positive for CD4 and negative for cell surface CD25 ($CD4^+CD25^{neg}$) to preclear aptamers that bound to common T cell antigens and a positive selection step with Tregs that were both positive for CD4 and contained high levels of cell surface CD25 ($CD4^+CD25^{high}$) to select for Treg-specific binders. Treg-bound aptamers were then extracted using Trizol method and then amplified by RT-PCR, techniques known to those of ordinary skill in the art. Amplified DNA template (now identified as Rd 1) was transcribed in vitro and used for the next round of SELEX. A total of eight rounds of SELEX was done (Table 2) and by the end of eighth round, aptamers from each round were subjected to Illumina-based high-throughput sequencing and bioinformatics analysis.

Methods of Making Aptamers that Bind to Cells Expressing Complexes or Cells Expressing Receptor Ligand Complexes RNA aptamers that recognized human Treg cells were generated using a cell-based SELEX strategy with modifications needed to incorporate primary Treg and Teff cells (summarized in FIG. 1) (*PLoS One. 2012; 7(9):e43836). The sequences of SEL2-based DNA library and the primers used are shown in Table 1 and were synthesized (IDT, Coralville, Iowa, USA). DNA template for SEL2 RNA library, primers, silencing RNA (siRNA) were chemically synthesized (Integrated DNA technologies, USA). Starting RNA library was created by transcribing the double-stranded DNA templates with a mutant T7 RNA polymerase (*PLoS One. 2012; 7(9):e43836) and 2' fluoro-modified CTPs and UTPs to incorporate RNase resistance. SELEX was performed with 1.5 nanomoles of RNA library (containing a calculated representation of ~903 copies per sequence in the unenriched starting library) that was folded at a concentration of 2 µM in AIM-V (BSA) media (*PLoS One. 2012; 7(9):e43836; FIG. 1). Peripheral blood mononuclear cells (PBMCs) and primary human T cell subsets, including CD4+CD25high Treg cells and CD4+CD25neg Teff cells, from healthy human donors were isolated from the leucocyte retention system cones (LRS) (DeGowin blood donor center, University of Iowa) using commercially-available magnetic cell separation kits (Miltenyi Biotech, USA). Primary cells were incubated in AIM-V medium containing BSA (Thermo Fisher, USA) for cell-based SELEX and cell binding assays. At the time of SELEX, folded aptamer library was diluted to 100 nM concentration and was pre-cleared using primary human Teff cells (CD4+CD25neg T cells) for 15 minutes at 37 degrees Celsius to remove aptamers that bound to common T cell antigens. Pre-cleared aptamer library was then bound to autologous primary human Tregs (CD4+CD25high T cells) (Table 2). One ordinarily skilled in the art would recognize that, because Tregs express high levels of CD25, which is a high affinity receptor for interleukin-2 (IL-2), Tregs purified from human donors contain high levels of IL-2 ligand-bound CD25. The unbound aptamer fraction, which mostly contained aptamers that did not react with any Treg-specific antigens, was discarded. After three washings with AIM-V (BSA) medium at 37 degrees Celsius (Table 2), Treg-bound aptamer fraction was extracted using Trizol and amplified by RT-PCR using the SEL-2 primers. Purified PCR products were then subjected to in vitro transcription to create the RNA aptamer pool for the second round of SELEX. The SELEX was repeated for a total of eight rounds, each round done with T cells obtained from different human donors. Donors could be other primates, mammals, vertebrates, multicellular organisms, or, in some cases, eukaryotes or other single-celled organisms. RNA and DNA-modifying enzymes, qPCR kits and general molecular biology products were obtained from Thermo Fisher, Promega and New England Biolabs (USA).

DNA Melt Assay:

We monitored the change in the complexity of aptamer pools after select rounds of enrichment using a DNA melt assay (*PLoS One. 2012; 7(9):e43836). The complexity of nucleotide sequences in the aptamer library progressively decreases after each round of SELEX when non-specific sequences are precleared and Treg binders get enriched. This results in increase in the copy number of specific sequences resulting in a shift in their overall melting curve towards right (higher Tm). Unenriched aptamers that are high complex show a left shift in their melting curve indicating a lower average Tm. To perform this, 20 pmoles of PCR DNA generated from Treg-bound RNA pool after SELEX (Rounds 2, 4, 6 and 8) was separately mixed with equal amounts of 2× SyBR green PCR mix (Promega, USA). The samples were then subjected to a standard DNA melt curve analysis (95*C to 25*C over 20 min ramp time). SyBR green fluorescence was plotted against the temperature and the melt curve was generated.

As shown in FIG. 6A, subsequent rounds of SELEX resulted in a progressive rightward shift in the DNA melt curve suggesting effective selection resulted in reduced complexity of the aptamer pool with advancing SELEX rounds.

High-Throughput Sequencing and Bioinformatics Analysis:

During each round of SELEX, aliquots of RNA aptamer pool and its corresponding PCR product were saved and subjected to Illumina-based high-throughput sequencing (HTS) (Genomics Division, University of Iowa) at the end. A total of 77.1 million sequences were analyzed using a series of standardized bioinformatics workflows (*Nucleic Acid Ther. 2011 August; 21(4):253-63) to analyze the enrichment efficiency, cluster size and copy numbers. Individual sequences were ranked based on their copy numbers in the final round of SELEX. Sequences were then selected for further binding analysis, if they satisfied the following conditions:

1. They were enriched to higher copy numbers in the final rounds
2. They showed a progressive enrichment across all or majority of the rounds
3. The represented the members of unique structure and sequence families found in the final pool.

Figures 2A, 2B, 2C, 2D:
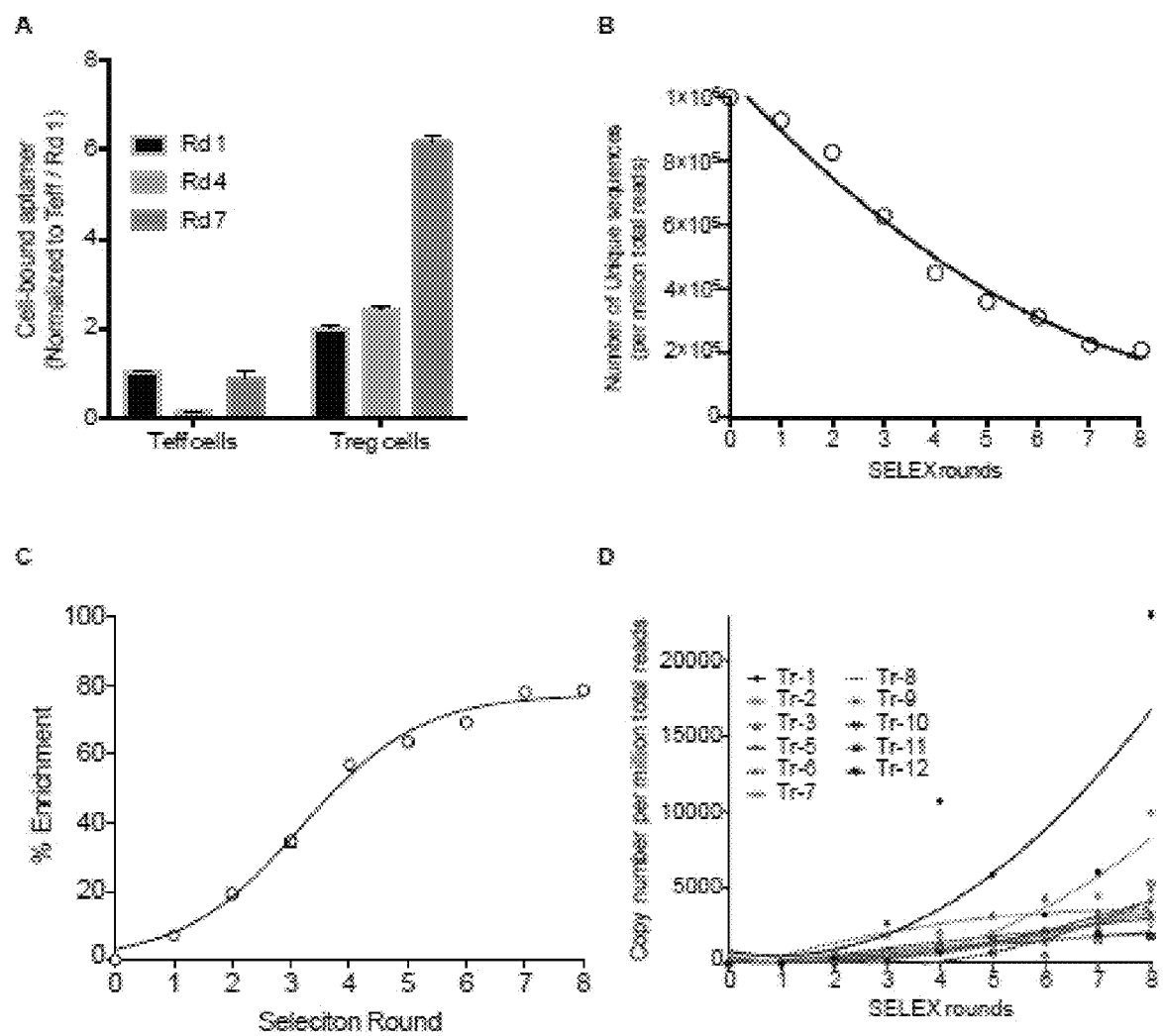
FIGS. 2A-2D. Evaluation of progression of cell-based SELEX. (A) Evaluation of binding to $CD4^+CD25^{neg}$ Teff and $CD4^+CD25^{high}$ Treg cells demonstrating predominant binding of the enriched aptamer pool to Tregs with subsequent rounds of SELEX. A representative plot of two independent sets is shown (Mean+/−SEM). (B) High-throughput sequencing of enriched aptamers from each round of SELEX demonstrating a progressive decrease in the number of unique sequences (per million total reads)

Aptamer DNA and RNA pools were evaluated by high-throughput sequencing. The sequences obtained were filtered for aptamer sequences that were devoid of unknown nucleotides (N), with intact constant regions and with variable regions+/−5 nucleotides. 157 million reads with an average 3.9 million reads per SELEX round revealed 77 million different aptamer sequences (data not shown). For each selection round, the total number of reads to the number of unique aptamer sequences was compared to determine the degree of enrichment [(1-unique)/total] (*PLoS One. 2012; 7(9):e43836). This revealed a significant decrease in the sequence complexity (FIG. 2B) and sequence enrichment (FIG. 2C) following progressive rounds of selection. For example, there was approximately 50% enrichment between rounds three and four. The sequences enrichment exhibits a plateau from round seven through eight, indicating that no additional selection (FIG. 2C).

Next, the abundance (FIG. 6B) and persistence (FIG. 6C) of 42.5 million unique aptamer sequences from various rounds were compared to the aptamer sequences found within the non-selected round 0 (negative control) (*Mol Ther. 2016 April; 24(4):779-787). This allowed for identification of aptamer sequences that were observed in at least four rounds of selection and had an abundance of at least 50 reads. Based on this preliminary metric, 4,500 aptamer sequences were identified for further analysis. These were clustered by sequence similarity (edit distance) and structure similarity (tree distance) (*PLoS One. 2012; 7(9):e43836). Next, aptamers were ranked based upon their Log 2 fold change in abundance across multiple rounds of selection (e.g. rounds 2 to 7, 1 to 4, 4 to 8). The final panel used for biological screening consisted of top candidate aptamers from different sequence and structure families that showed highest abundance with significant Log 2 fold enrichment across selection rounds. The overall copy numbers of the ten most highly enriched aptamers and their progression in each round is illustrated in FIG. 2D.

TABLE 1

Template and primers used for SELEX

| SEQ ID NO: | Sequences |
|---|---|
| 12 | Forward primer taatacgact cactataggg aggacgatgc gg |
| 13 | Reverse primer tcgggcgagt cgtctg |
| 14 | Template tcgggcgagt cgtctg-N20-ccgcatcgtc ctccc |

TABLE 2

Binding conditions used for Treg cell-based SELEX

| Rounds | Binding medium | [RNA] | Preclearing (CD4+CD25$^{neg}$ Teff cells) | Binding (CD4+CD25$^{high}$ Treg cells) |
|---|---|---|---|---|
| 1 | AIM-V (BSA) | 100 nM | 15 minutes, once | 30 minutes |
| 2 | AIM-V (BSA) | 100 nM | 15 minutes, once | 30 minutes |
| 3 | AIM-V (BSA) | 100 nM | 15 minutes, once | 30 minutes |
| 4 | AIM-V (BSA) | 100 nM | 15 minutes, once | 30 minutes |
| 5 | AIM-V (BSA) | 100 nM | 15 minutes, twice | 30 minutes |
| 6 | AIM-V (BSA) | 100 nM | 15 minutes, twice | 30 minutes |
| 7 | AIM-V (BSA) | 100 nM | 15 minutes, twice | 30 minutes |
| 8 | AIM-V (BSA) | 100 nM | 15 minutes, twice | 30 minutes |

Cell-Based SELEX Enriches Human Treg-Binding RNA Aptamers:

The SELEX approach designed to enrich RNA aptamers that bound to human Tregs is shown in FIG. 1. The starting library consisted of SEL2-based RNA aptamers containing 20 random nucleotide sequence (N20) spanned by SEL2-specific primer-binding region. Preclearing was done with CD4+CD25neg Teff cells before binding to CD4+CD25high Treg cells obtained from the same donor. SELEX was done using freshly-obtained T cell subsets from a different healthy donor for each round to ensure that the aptamers recognized Treg antigens from across diverse subjects. The preclearing and binding conditions used for each round of SELEX are outlined in Table 2.

Figures 5A, 5B, 5C, 5D, 5E:
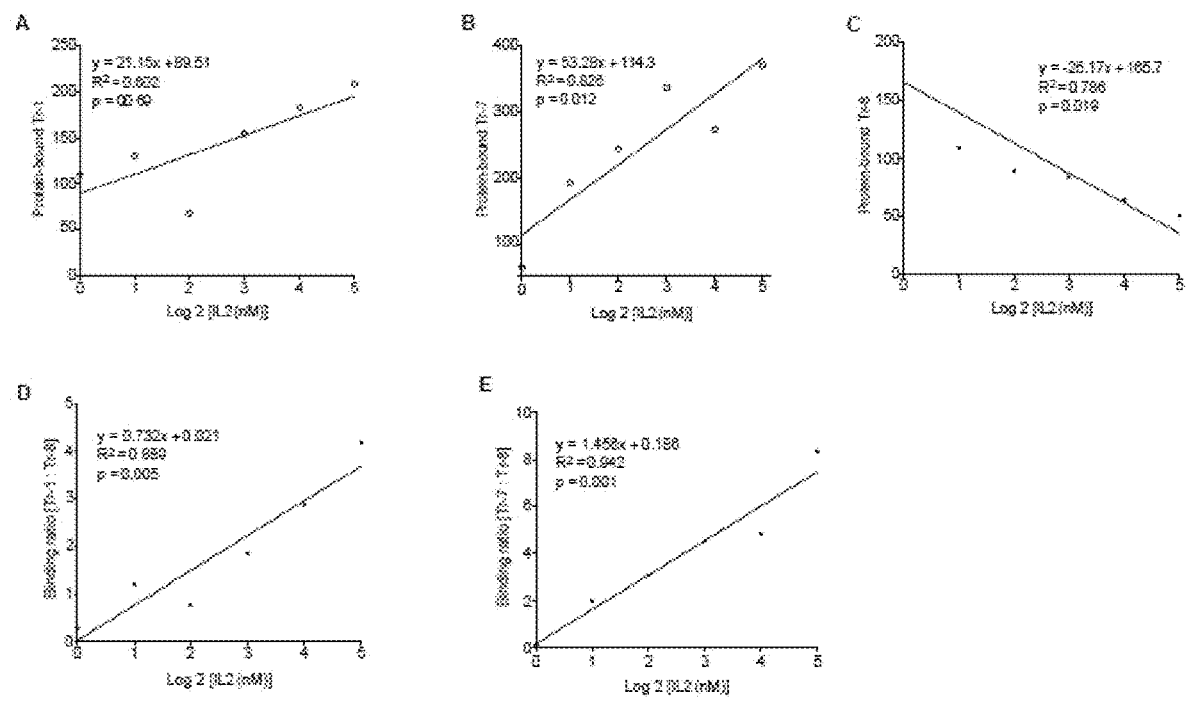

The status of the aptamer pool enrichment during SELEX was initially monitored using a DNA melt assay as a measure of decreasing complexity of the library (*PLoS One. 2012; 7(9):e43836). As shown in FIG. 5A, there was a progressive shift of DNA melt curve towards right in the later rounds of SELEX when compared to earlier rounds. This suggested that the complexity of the aptamer pool decreased with advancing SELEX rounds.

High-throughput sequencing and bioinformatics analysis was also used to assess aptamer diversity in all the rounds to SELEX. An average of ~3.3 million aptamers were sequenced per round. Following conditions were used to further select the unique sequences enriched during SELEX:

1. Sequences that did not contain the full SEL2-primer binding region (FIG. 1) were rejected. Because the initial library consisted of aptamers with approximately 20mer random region (N20), only those aptamers whose random region was 20+/−1 nucleotide long were selected for further analysis.

2. Unique sequences in each round were identified and their progression across rounds were determined. A progressive drop in the number of unique sequences was seen over SELEX (FIG. 2B).

3. This was seen in parallel with a gradual increase in the enrichment of unique sequences (FIG. 2C) in later rounds of SELEX.

4. Furthermore, an increase in the cluster size of sequences due to enrichment of homologous sequences was seen in the later rounds of SELEX (Rd 4 and 8).

Based on the cluster size in the initial library, we selected aptamer sequences that had >10 copies in any of the rounds for further analysis. Based on this preliminary metric, we chose approximately 4,500 aptamers for further analysis. The final panel used for biological screening consisted of top candidate aptamers that showed highest copy numbers and that were representatives of their sequence and structure families. The overall copy numbers of the ten most highly enriched aptamers and their progression in each round is illustrated in FIG. 2D.

Example 2

Method to Detect Aptamer Binding to Cells Containing a Complex or Cells Containing a Receptor Ligand Complex Cell-Based Aptamer Binding Assays:

We measured the aptamer binding to CD4+ T cell subsets or the HEK cells using an RT-qPCR assay. Briefly, primary human CD4+CD25$^{high}$ Treg and CD4+CD25$^{neg}$ Teff cells were enriched from healthy donors using commercially available Treg isolation kit (Miltenyi Biotech, USA). For HEK cells, parental HEK293 cells and HEK-CD25 cells were plated for 24 hours in D-MEM growth medium and washed with AIM-V (BSA) medium just before the assay. Established HEK293 and HEK-CD25 (HEK293 overexpressing human CD25) was maintained in DMEM growth medium and was resuspended in AIM-V (BSA) medium just before binding assays. Cells were blocked with 0.1 mg/ml tRNA in AIM-V (BSA) medium for 15 minutes at 37 degrees Celsius before incubating with 100 nM folded RNA aptamers. After 30 minutes of aptamer binding at 37 degrees Celsius, cells were washed thrice with AIM-V (BSA) medium and total RNA was extracted with Trizol spiked with a reference control RNA (M12-23 aptamer) to normalize for the variations in the efficiency of the RNA extraction procedure (*Nat Biotechnol. 2006 August; 24(8):1005-15; PLoS One. 2012; 7(9):e43836). Endogenous cellular RNA was digested with RNase A and RNA aptamers were precipitated with ice-cold ethanol. T cellbound RNA aptamers were quantified by a SyBR green-based RT-qPCR assay (Promega, USA). T cell-bound RNA aptamers were normalized to the reference M12-23 control before further analysis. The values obtained for CD25-binding individual aptamers were normalized to the negative control aptamer, C-248, or Rd 0 (if SELEX rounds were tested) and plotted.

Detecting Aptamer Binding to Cells:

To directly assess the enrichment of Treg-binding aptamers after SELEX, we used T cell-based binding assay. As illustrated in FIG. 2A, aptamer pools from rounds 1, 4 and 7 were incubated with Tregs and Teff cells from the same donor and aptamer binding was measured using RT-qPCR.

An increased binding of aptamer pools to Tregs was seen in Rd 7 when compared to rounds 1 and 4 indicating enrichment of Treg-binding aptamers. No increase in binding to Teff was seen with aptamers from progressive rounds (FIG. 2B). These results suggest that the SELEX process enriched RNA aptamers that bound preferentially to antigens expressed by Tregs.

Figures 3A, 3B, 3C, 3D:
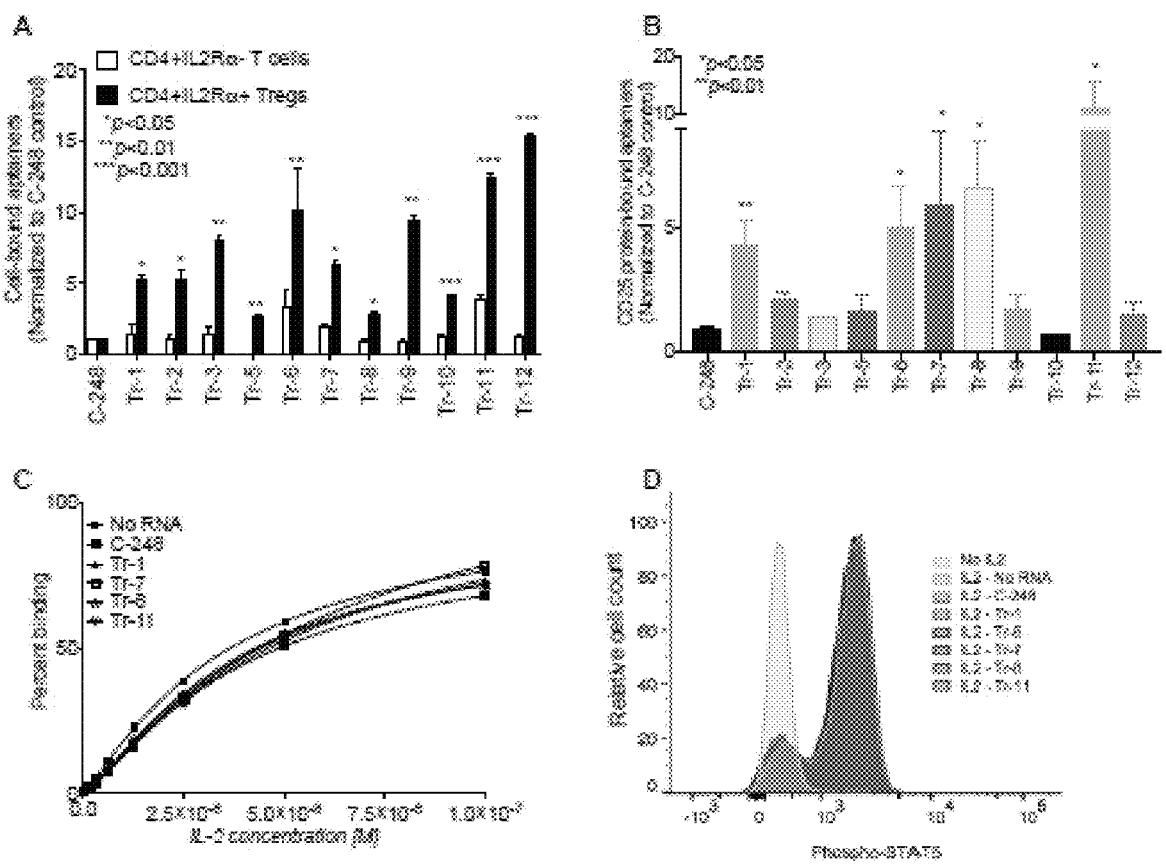

The most highly enriched RNA aptamers were synthesized as 2' fluoro-modified RNA (TriLink, USA) and folded at 2 uM concentration in AIM-V (BSA) medium (for cell binding assays) or binding buffer (protein-binding assays). Folded aptamers were then tested for their ability to bind to CD4+CD25high Tregs and CD4+CD25neg Teff cells. Aptamers were incubated with enriched primary human Tregs and Teff cells and bound aptamers were quantified using RT-qPCR. Data indicated that all selected aptamers bound in higher quantities to Tregs than to Teff cells (FIG. 3A). The negative control aptamer (C-248), which was a randomly selected aptamer lost early in the SELEX, did not bind to either T cell subset.

Example 3

Methods to Identify Aptamers that Bind to a Complex and to Detect Complexes

CD25 and CD25-IL2 Protein-Based Binding Assays:

Aptamer binding to recombinant CD25 protein or CD25-IL2 receptor-ligand complex-coated Dynabeads was measured as follows. Streptavidin-coated Dynabeads, antibody-coupling kit, and Dynabeads for His-tagged protein binding were obtained from Thermo Fisher. Histidine-tagged recombinant human CD25 (Thermo Fisher, USA) was coated onto His-tag-binding Dynabeads (Thermo Fisher, USA). Protein coated beads were blocked with binding buffer [HEPES-buffered saline with 2 mM CaCl2) containing 0.1 mg/ml BSA and tRNA. In cases where CD25-IL2 complexes were tested, equimolar amounts of IL2 was incubated with CD25-coated beads for 30 minutes at 37 degrees Celsius and the unbound IL2 was washed away. Folded aptamers were then incubated with CD25- or CD25-IL2-coated beads at a concentration of 100 nM for 30 minutes at 37 degrees Celsius under rotation. Beads were then washed thrice with binding buffer at 37 degrees Celsius. Bound RNA aptamers were extracted using Trizol spiked with M12-23 reference control and were quantified using SyBR green-based RT-qPCR assay. The bead-bound SEL2 aptamers were normalized to M12-23 reference control before further analysis. The values obtained for Treg-binding aptamers were normalized to the negative control aptamer, C-248, and plotted. CD25-binding and control RNA aptamers identified in this study are listed in Table 1. Nucleotides corresponding to the N20 region are underlined and italicized.

Statistical Analysis:

All the experiments, unless specifically mentioned, were repeated at least twice to ensure reproducibility. Data points from multiple assays, done with similar conditions, were pooled and mean and standard error of mean (SEM) were calculated. Significance of the mean (P value) were analyzed using student t-test using the GraphPad Prism software and a P value of >0.05 was considered significant.

Enzyme-Linked Aptamer Sorbent Assay (ELASA):

Enzyme-linked aptamer sorbent assay (ELASA) was performed to analyze the EC50 of aptamer binding to CD25 or the CD25-IL2 complexes. Briefly, recombinant histidine-tagged CD25 was coated on an ELISA plate (Corning, USA) at a concentration of 1 mg/ml and incubated at 4 degrees Celsius overnight. The plate was then blocked in the blocking buffer (Binding buffer containing 3% BSA and 0.1 mg/ml tRNA). For making IL2-CD25 complexes, equimolar concentrations of IL2 was added to CD25-coated plates and incubated for 30 minutes at 37 degrees Celsius. Plates were washed in wash buffer (Binding buffer containing 0.01% Tween-20) and were incubated with serially diluted, folded biotin-labeled synthetic aptamers for 30 minutes at 37 degrees Celsius. Plates were washed thrice and were further incubated with diluted HRP-conjugated streptavidin (eBiosciences, USA). Plates were then washed in wash buffer and developed using the TMB+H2O2 substrate solution (eBiosciences, USA). Color development was read at 450 nm with the background subtraction at 650 nm. The absorbance values were used to calculated percentage of IL2-occupied CD25 using Hills equation in the GraphPad Prism software (GraphPad software, USA) and plotted.

Identification of RNA Aptamers that Recognize CD25:

Tregs have high expression of surface CD25 when compared to resting Teff cells (*Scand J Immunol. 2007 January; 65(1):63-9), thus we hypothesized that some of aptamers recognize CD25. A protein binding assay using recombinant human CD25-coated dynabeads demonstrated that five of the eleven aptamers tested (Tr-1, Tr-6, Tr-7, Tr-8 and Tr-11) showed high binding to CD25 than the negative control C-248 aptamer (FIG. 3B). The sequences of the abovementioned five aptamers are shown in Table 3. All nucleotide sequences contained herein are represented as set forth in WIPO Standard ST.25 (1998), Appendix 2, Table 1. CD25 binding aptamers also bound in significantly higher quantities to human HEK293 cells overexpressing CD25 (HEK-CD25) when compared they did to parental CD25neg HEK (HEK 293) cells (FIG. 3C). The negative control aptamer, C-248, bound to HEK-CD25 significantly lower levels than Tr-1 aptamer (FIG. 3C). Thus, many but not all of the aptamers identified as Treg binders are specific for CD25.

TABLE 3

CD25-binding aptamers used in this study
RNA sequence of human CD25-binding aptamers identified in this study is given below. The nucleotides corresponding to the N20 region is underlined.

| SEQ ID | Name | Sequence |
| --- | --- | --- |
| SEQ ID NO: 1 | C-248 | gggaggacga ugcgg<u>cacac cgaaauqucc cgacu</u>cagac gacucgcccg a |
| SEQ ID NO: 2 | Tr-1 | gggaggacga ugcgg<u>uccug ucgucuguuc guccc</u>cagac gacucgcccg a |
| SEQ ID NO: 3 | Tr-6 | gggaggacga ugcgg<u>cquuu ccucugguuc guccc</u>cagac gacucgcccg a |
| SEQ ID NO: 4 | Tr-7 | gggaggacga ugcgg<u>ugagu cguucccuuc guccc</u>cagac gacucgcccg a |
| SEQ ID NO: 5 | Tr-8 | gggaggacga ugcgg<u>ccgu uguuguguge cgccc</u>cagac gacucgcccg a |
| SEQ ID NO: 6 | Tr-11 | gggaggacga ugcgg<u>auucu gguuacuggc cgccc</u>cagac gacucgcccg a |
| SEQ ID NO: 7 | 1/7a | gggaggacga ugcgg<u>usmkk yskucysuuc guccc</u>cagac gacucgcccg a |
| SEQ ID NO: 8 | 1/7b | gggaggacga ugcgg<u>unnnn nnnucnnuuc guccc</u>cagac gacucgcccg a |
| SEQ ID NO: 9 | 6/8/11a | gggaggacga ugcgg<u>vbybu bsuydbkkkc skccc</u>cagac gacucgcccg a |
| SEQ ID NO: 10 | 6/8/11b | gggaggacga ugcgg<u>nnynu nsuynnkkkc skccc</u>cagac gacucgcccg a |
| SEQ ID NO: 11 | 6/8/11c | gggaggacga ugcgg<u>nnnnu nnuunnnnnc nnccc</u>cagac gacucgcccg a |

Example 4

Methods to Detect Complexes, Receptor Ligand Complexes, Cells Containing Complexes, or Cells Containing Receptor Ligand Complexes and to Analyze Complexes, Receptor Ligand Complexes, Cells Containing Complexes, or Cells Containing Receptor Ligand Complexes CD25-IL2 Enzyme-Linked Immunosorbent Assay:

The effect of aptamer binding on the interaction between CD25 and IL2 was determined by an ELISA-based assay. Briefly, recombinant histidine-tagged CD25 was coated on an ELISA plate (Corning, USA) at a concentration of 1 mg/ml and incubated at 4 degrees Celsius overnight. The plate was then blocked in the blocking buffer (Binding buffer containing 3% BSA and 0.1 mg/ml tRNA). Plates were washed in wash buffer (Binding buffer containing 0.01% Tween-20) thrice. Plates were then incubated with 400 nM folded synthetic aptamers for 15 minutes at 37 degrees Celsius. Serially diluted human IL2 was added to the wells containing the aptamers. The incubation was prolonged for additional 30 minutes at 37 degrees Celsius. Plates were washed thrice and were further incubated with 1:2000 diluted anti-human IL2 polyclonal IgG (R&D System, USA). Plates were then washed in wash buffer and developed using HRP-conjugated anti-goat IgG antibody followed by incubation with TMB+H2O2 substrate solution (eBiosciences, USA). Color development was read at 450 nm with the background subtraction at 650 nm. The absorbance values were used to calculated percentage of IL2-occupied CD25 using Hills equation in the GraphPad Prism software and plotted.

Flow Cytometry:

Binding of A647-labeled aptamers to Tregs was determined by flow cytometry method. Briefly, Tregs were enriched from the blood of healthy volunteers and blocked with AIM-V (BSA) medium containing 0.1 mg/ml tRNA for 15 minutes at 37 degrees Celsius. Tregs were then treated with 2 nM IL2 (corresponding to 300 U/mL) or just PBS along with the indicated RNA aptamers for 30 minutes at 37 degrees Celsius. Cells were then washed thrice with binding buffer containing tRNA at 37 degrees Celsius. For phospho-STAT5 staining, cells were fixed in 1× Foxp3 fixation buffer (eBiosciences, USA) and were permeabilized with ice-cold methanol. Cells were then washed thoroughly with PBS containing 0.1% BSA and stained with FITC-conjugated anti-human phospho-STAT5 antibody (eBiosciences, USA) for 30 minutes. Cells were washed and read using the LSR II-UV flow cytometer. Histograms of phospho-STAT5 fluorescence was plotted using FlowJo v10 software.

Aptamer Binding to the CD25-IL2 Complex:

While aptamers did not impact on IL2 binding to Tregs or IL2-mediated signaling, IL2 did have an impact on the ability of anti-CD25 aptamers to bind to CD25. Addition of IL2 to CD25, which leads to the formation of IL2-CD25 ligand-receptor complexes, resulted in increased binding to CD25 of some of the aptamers (Tr-1 and Tr-7) and reduced binding of others (Tr-6 and Tr-8) (FIG. 4A). Results with a Treg cell-based binding assay were similar to those seen with the cell-free protein-based assays. Tr-1 and Tr-7 bound in higher quantities, while Tr-6 and Tr-8 bound in lower quantities to IL2-treated Tregs (FIG. 4B). Tr-11 bound to both IL2-treated and untreated Tregs equally. Thus, some of the CD25-binding aptamers bind preferentially to the IL2-CD25 complex, while others show preferential binding to the unoccupied CD25.

Aptamers do not Interfere with IL2-CD25 Interaction:

IL2 is a natural ligand for CD25. We therefore questioned whether the CD25-binding aptamers interfered with the binding of IL2 to CD25. This hypothesis was assessed using an ELISA-based assay to measure IL2 binding to CD25 in the presence or absence of aptamers. As shown in FIG. 3C, none of the aptamers altered the ability of IL2 to bind CD25. The inability of aptamers to interfere with IL2 binding was irrespective of the order of addition of aptamers (prior to or during the CD25-IL2 complex formation) or the quantity of aptamers (200 nM and 400 nM) (data not shown).

Similar results were found in a functional system exploring the impact of aptamer on T cell signaling mediated by IL2. This was done by assessing the effect of IL2 on Treg expression of tyrosine phosphorylation of STAT5 (*Blood. 2011 Sep. 8; 118(10):2809-20). Up to a 10-fold increase in phospho-STAT5 levels was observed 30 minutes after addition of IL2 as measured by flow cytometry. CD25-binding aptamers did not significantly alter the levels of phospho-STAT5 induced by IL2 in Tregs (FIG. 3D). Thus, none of the CD25 aptamers impacted on IL2 binding to CD25 as well as their signaling.

Example 5

Methods to Measure Complex Formation, Molecule-Molecule Interactions, or Receptor-Ligand Interactions Aptamer-Based Assay to Measure IL2 Occupancy on CD25

The panel of CD25-binding aptamers we generated show differential binding towards unoccupied CD25 and IL2- occupied CD25. Exploiting this differential binding, we developed a TaqMan RT-qPCR-based binding assay to specifically quantify the fraction of CD25 that is occupied by IL2 by multiplexing two aptamers with contrasting binding affinities to the complex. The primer and probe sequences used for the TaqMan RT-qPCR is given in Table 4. Double-quenched probes were used that consisted of the indicated nucleotides conjugated to FAM, HEX, or TET dyes at the 5' terminus, ZEN quencher internally, and IBFQ quencher at the 3' terminus (IDT, Coralville, Iowa, USA). Briefly, we coated Dynabeads with recombinant histidine-tagged human CD25 [25 nM]. CD25-coated beads were then incubated with two-fold serially diluted IL2 concentrations [160 nM to 5 nM] to create various fractions of CD25 occupied by IL2. To perform the binding assay, aptamers showing contrasting binding preferences were multiplexed in equimolar concentrations (Tr-8 with Tr-1 or Tr-7). Aptamer pairs were then incubated Dynabeads coated with various fractions of IL2-occupied CD25, as described above. After washing, bound aptamers were extracted and the quantities of each aptamer bound to the complex was measured using TaqMan probe-based RT-qPCR. The ratio of bound aptamers at each IL2 concentration was calculated by dividing the quantity of bound Tr-1 or Tr-7 aptamer by the quantity of bound Tr-8 aptamers. A standard curve was then generated by plotting the binding ratio against the logarithmic concentrations of IL2 (Log 2[IL2] added during the complex formation. The standard curves were then used to measure IL2 occupancy of CD25 from blindfolded samples containing various fractions of IL2-bound CD25.

Aptamers Specific for the IL2-CD25 Complex can be Used to Quantify IL2 Occupancy Based on the finding that the CD25-binding aptamers display differential binding preferences towards unoccupied CD25 versus the IL2-occupied CD25 yet have the same 5 prime and 3 prime sequences, an aptamer-based RT-qPCR assay was developed to measure the level of IL2 occupancy of CD25 receptors. Equimolar concentrations of complex-preferring aptamers (e.g. Tr-1) and receptor-preferring aptamers (e.g. Tr-8) were added to CD25-coated Dynabeads pre-incubated with serial dilutions of IL2 to create various percentages of IL2-occupied CD25 receptors. Binding of individual aptamers to the protein-coated beads was quantified using TaqMan-based RT-qPCR by probing with different fluorochromes. As shown in FIGS. 5A and 5B, binding levels of Tr-1 (p=0.069) and Tr-7 (0.012) showed a positive correlation with increasing levels of IL2-occupied receptors. Conversely, Tr-8 displayed an inverse correlation with increasing levels of IL2-occupied receptors (p=0.019; FIG. 5C). To create regression curves that can deduce the receptor occupancy, the ratios of bound Tr-1 or Tr-7 to bound Tr-8 was determined at each receptor occupancy level. There was a strong linear relationship (p<0.01) between aptamer binding ratios when plotted against logarithmic concentrations of IL2 ($Log_2[IL2]$) added to CD25 (FIGS. 5D and 5E).

TABLE 4

TaqMan primers and probes used in this study

| SEQ ID NO: | Name | Sequence |
|---|---|---|
| 15 | Forward Primer | tatagggagg acgatgcgg |
| 13 | Reverse Primer | tcgggcgagt cgtctg |
| 16 | Tr-1 Probe | FAM/tctgggac/ZEN/gaacagacga cagga/IBFQ |
| 17 | Tr-6 Probe | HEX/tctgggac/ZEN/gaaccagagg aaac/IBFQ |
| 18 | Tr-7 Probe | FAM/tctgggac/ZEN/gaagggaacg actca/IBFQ |
| 19 | Tr-11 Probe | TET/tctgggcg/ZEN/gcacacaaca acggc/IBFQ |

TABLE 5

Receptor ligand pairs

| Receptor | Ligand | Journal article describing biological significance of pair |
|---|---|---|
| CD25/CD122/CD132 (IL2Rs) | IL2 | * Immunity. 2010 Aug 27; 33(2): 153-65 |
| Cytokine receptors (IL1bR, IL3R-IL35Rs, CSFRs, Chemokines receptors, TNFRs, etc) | Cytokines (IL1b, IL3-IL35, CSFs, Chemokines, TNFs etc) | *Cancers (Basel). 2011 Oct 13; 3(4): 3856-93 |
| Growth factor receptors (EGF, FGF, PDGF, TGF-b, etc) | Growth factors (EGFR, FGFR, PDGFR, TGF-b RI/II, etc) | *Expert Opin Emerg Drugs. 2017 Jun; 22(2): 165-174 |
| Immune receptors (eg. PD1, CTLA4, CD28, ICOS, TCR, LAG3, CD137, OX40, CD40L, etc) | Immune ligands (PD-L1, CD80/CD86, B7RP1, B7-H3, B7-H4, MHC I/II, CD137L, OX40L, CD40, etc) | *Nat Rev Cancer. 2012 Mar 22; 12(4): 252-64 |

Example 6

Method of Determining the Fraction of a Type or Types of Molecule in a Sample that is Bound to Another Specified Type or Types of Molecule in the Sample

Determining IL2 Occupancy in Unknown Samples
As exemplified in FIG. 7A, this involves:
1. Adding two aptamers simultaneously to a biological specimen
   a. One that binds preferentially to the ligand-receptor complex (IL2 bound to CD25)
   b. One that binds preferentially to the uncomplexed receptor (CD25 alone)
2. Washing off unbound aptamer
3. Expanding the bound aptamers by PCR using primers that are the same for both aptamer A and aptamer B
4. Quantifying the amount of aptamer A and aptamer B using probes such as florescent probes
5. Comparing the results of the unknown to standard curves to determine the percent of the receptor occupied by the ligand FIG. 7B depicts the results of an example use of the method. Dynabeads were coated with 25 nM CD25. Blinded preparations of IL2 concentrations were added to CD25-coated beads and incubated for 30 minutes at 37*C. The IL2 occupancy assay as outlined above was performed by incubating the blindly-prepared complexes with equimolar concentrations of Tr-7 and Tr-8. The bound aptamers and the aptamer binding ratios were calculated for the unknown samples, as described above. IL2 occupancy or the fraction of the ligand-bound receptor was derived using the standard curve generated using known standards.

One of ordinary skill in the art would know the above method can be used to study not only on the immune system. For example, it can be used to determine the binding of complexes that have a major impact on the growth, differentiation or death of cells in myriad settings or complexes involved in any other process. This can, for example, include cancer cells or stromal cells that support the growth of cancer cells such as in the endothelium. The method not only apply to complexes on the cell surface. I can used to probe intracellular complexes, soluble complexes, or any other type of complexes as well.

Example 7

Method of Making Aptamers that Bind to Receptor-Small Molecule Complexes

One embodiment of the invention is a method to obtain aptamers that bind to small molecule ligand-bound receptor complexes but not ligand-unbound receptor complexes. One ordinarily skilled in the art would recognize the method in example 1 can be adapted to make aptamers that bind to receptors only when bound to a small molecule ligand. A pool of cells of a single type that contain the receptor of interest can be split into two pools. One pool can be treated with the small molecule and the other pool left untreated, yielding one pool with receptor-small molecule complexes and the other without receptor-small molecule complexes. The two pools of cells can then be substituted for the two types of T cells used in Example 1 for the method of making of making aptamers that only bind to ligand-bound receptor complexes described in Example 1. Alternatively, two different types of cells with what one ordinarily skilled in the art would recognize as similar but distinct surface receptors can be substituted as in the example described immediately above.

TABLE 6

Receptor small molecule pairs

| Receptor | Small molecule | Journal article describing biological significance of pair |
|---|---|---|
| CD25 | Ro26-4550 | *Tiley et al., 1997; *Wilson and Arkin, 2010. Small-Molecule Inhibitors of IL-2/IL-2R: Lessons Learned and Applied. Small-Molecule Inhibitors of Protein-Protein Interactions. Current Topics in Microbiology and Immunology book series (CT MICROBIOLOGY, volume 348) p25-59 |
| PDGFR | SU9518 | *BMC Cancer. 2006; 6: 79 |
| EGFR | Gefitinib | *J Clin Oncol. 2003 Jun 15; 21(12): 2237-46 |
| PDGFR | Imatinib mesylate | *Nat Rev Cancer. 2006 Sep; 6(9): 714-27 |
| VEGFR, PDGFR, KIT, FLT3 | Sunitinib | *Nat Rev Cancer. 2006 Sep; 6(9): 714-27 |
| B-Raf, VEGFR2, EGFR, PDGFR | Sorafenib | *Nat Rev Cancer. 2006 Sep; 6(9): 714-27 |
| B cell and T cell receptor pathway | Dasatinib | *Drugs. 2011 Sep 10; 71(13): 1771-95 |

Example 8

Method of Making Aptamers that Bind to a Complex Only when One of the Molecules is a Therapeutic Molecule

One ordinarily skilled in the art would recognize that the methods of making aptamers that bind complexes as described in Examples 1 and 2 could be adapted to bind to complexes containing therapeutic molecules. One set of donors could be treated with the therapeutic molecule prior to donation of their cells, or one pool of cells could be treated with the therapeutic molecule. Aptamer selection would then be done by the SELEX methods described in Examples 1 and 2.

TABLE 7

Receptor therapeutic molecule pairs

| Receptor | Ligand | Journal article describing biological significance of pair |
|---|---|---|
| EGFR | Gefitinib | *J Clin Oncol. 2003 Jun 15; 21(12): 2237-46 |

TABLE 7-continued

Receptor therapeutic molecule pairs

| Receptor | Ligand | Journal article describing biological significance of pair |
|---|---|---|
| PDGFR | Imatinib mesylate | *Nat Rev Cancer. 2006 Sep; 6(9): 714-27 |
| VEGFR, PDGFR, KIT, FLT3 | Sunitinib | *Nat Rev Cancer. 2006 Sep; 6(9): 714-27 |
| B-Raf, VEGFR2, EGFR, PDGFR | Sorafenib | *Nat Rev Cancer. 2006 Sep; 6(9): 714-27 |
| B cell and T cell receptor pathway | Dasatinib | *Drugs. 2011 Sep 10; 71(13): 1771-95 |
| Her 2 | Transtuzumab and Pertuzumab | *MAbs. 2014 Jul-Aug; 6(4): 838-51 |
| CD20 | Rituximab | *Future Oncol. 2015; 11(9): 1327-42 |
| EGFR | Cetuximab, Panitumumab, Nimotuzumab | *MAbs. 2014 Jul-Aug; 6(4): 838-51 |
| PD-1 | Pembrolizumab, Nivolumab, | *Int Immunol. 2015 Jan; 27(1): 39-46 |
| PD-L1 | Atezolizumab, Avelumab and Durvalumab | *Int Immunol. 2015 Jan; 27(1): 39-46 |

Example 9

Method of Detecting Complex Formation or a Complex with an Aptamer

The complexes described in Examples 1-8 can be detected using the aptamers described in Examples 1-9. One of ordinarily skilled in the art would know there are many ways to detect a molecule bound to a complex. Those methods will involve contacting the aptamer to a sample suspected to contain the complex of interest.

The aptamer can be conjugated directly to a fluorescent molecule, such as fluorescein isothiocyanate (FITC), or it can be conjugated to an intermediate molecule such as biotin. The fluorescently conjugated aptamer can be directly detected by a technique such as fluorescence microscopy (Proc Natl Acad Sci USA. 2006 Aug. 8; 103(32):11838-43) or flow cytometry (PNAS, 103(32):11838-43, 2006). Alternatively the aptamer conjugated to an intermediate molecule, such as biotin, can be contacted with a secondary fluorescently conjugated molecule, such as an antibody that specifically binds to biotin and is conjugated to a fluorescent molecule, such as fluorescein isothiocyanate. Alternatively, the aptamer can be conjugated with an intermediate molecule. The conjugated aptamer can then be contacted with a secondary molecule that binds to the intermediate molecule, such as a biotinylated secondary antibody. The secondary antibody can then be contacted with a tertiary molecule conjugated to a molecule that facilitates recognition of the tertiary molecule, such as streptavidin conjugated to horseradish peroxidase that can act on a detectable substrate.

Complexes to be detected can be in many different forms that would be known to one ordinarily skilled in the art. In one embodiment the complexes are purified, such as in an assay to quantify the number of complexes. In another embodiment the complexes are attached to cells, such as tissue culture cells. The cells can be in many different states including but not limited to being live, permeabilized with a reagent such as a detergent, fixed by precipitation such as with methanol, or fixed by cross-linking reagent such as formalin (Mod Pathol. 2010 December; 23(12):1553-8). In another embodiment the complexes are attached to a biological sample, such as surgically removed tissue, an explant, body fluid, a xenograft, or an intact organism (Anal Chem. 2011 Feb. 1; 83(3):727-34).

One ordinarily skilled in the art would know that complex formation can be detected by monitoring the number of complexes throughout a period of time or at a specific time. Complexes, rather than complex formation, can be quantified at any time.

TABLE 8

Methods of detection

| Methods of detection using aptamers | Journal article describing method |
|---|---|
| Flow cytometry and microscopy | *Appl Microbiol Biotechnol. 2013 Aug; 97(16): 7097-109; *Nat Methods. 2012 Oct; 9(10): 938-9 |
| RT-PCR | *Bioconjug Chem. 2010 Dec 15; 21(12): 2183-9 |
| Enzyme-based assay | *Biosens Bioelectron. 2015 Feb 15; 64: 392-403 |
| Immunohistochemistry | *Nucleic Acid Ther. 2016 Jun; 26(3): 120-6 |
| Imaging and tracking | *J Nucl Med. 2014 Mar; 55(3): 353-6 *PLoS One. 2016 Feb 22; 11(2): e0149387 |

Example 10

Method of Detecting Complexes Comprising at Least One Therapeutic Molecule and One Endogenous Molecule One ordinarily skilled in the art upon reading this disclosure will appreciate that the method of complex detection described in Example 9 can be used to detect complexes containing a therapeutic molecule such an antibody or antibody fragment, with aptamers made as described herein.

Example 11

Method of Purifying Complexes of Interest or Cells Containing Complexes of Interest In one embodiment aptamers that bind to a complex are used to purify the complex by affinity capture (see, e.g. Cold Spring Harb Protoc. 2016 Jul. 1; 2016(7):pdb.top077545).

One ordinarily skilled in the art would recognize this is conceptually similar to antibody-based co-immunoprecipitation. In one embodiment (PLoS One. 2010 Dec. 7; 5(12): e15004) an aptamer that binds to a complex is conjugated to biotin. The biotinylated aptamer is contacted to a sample suspected to contain the complex of interest. Magnetic beads conjugated with streptavidin are added to the sample to allow the beads to contact the aptamer. The beads are then collected by applied a magnet to the sample. Allowing the beads to be immobilized by the magnet, and washing away any unbound sample to leave only or mostly magnetic beads bound to the complex of interest. Alternatively, the above method can be modified to bind the biotinylated aptamer to the streptavidin-conjugated magnetic beads prior to addition to the sample suspected to contain the complex of interest.

TABLE 9

Methods of complex purification

| Methods of complex purification using aptamers | Journal article describing method |
|---|---|
| Affinity purification | *Biotechnol Rep (Amst). 2015 Dec; 8: 16-23 |
| Affinity chromatography | *J Chromatogr B Biomed Sci Appl. 1999 Aug 20; 731(2): 275-84 |
| Magnetic bead-based affinity separation | *Methods Mol Biol. 2015; 1286: 67-82 |

In one embodiment the aptamers that bind to a complex are used to purify cells that contain that complex. This can be accomplished using fluorescence-activated cell sorting (FACS) (Biol Pharm Bull. 2014; 37(11):1742-9). Cells suspected to contain the complex of interest are contacted with an aptamer that binds the complex and is conjugated to a fluorophore, such as FITC. The resulting mixture is then sorted by FACS to isolate only cells that contain or are enriched in the complex of interest. Alternatively, the aptamer that binds to the complex of interest can be conjugated with an intermediate molecule, such as biotin, and then used to purify the cells containing the complex of interest using a support, such as magnetic nanoparticles, conjugated to a molecule that binds to the intermediate molecule, such as streptavidin (Anal Chem. 2006 May 1; 78(9):2918-24).

TABLE 10

Methods of cell purification

| Methods of cell purification using aptamers | Journal article describing method |
|---|---|
| Circulating tumor cell isolation | * Cancer Res. 2010 Nov 15; 70(22): 9371-80; * Anal Chem. 2012 May 1; 84(9): 4199-206 |

Example 12

Method of Using an Aptamer to Deliver a Molecule to a Cell that Contains the Complex of Interest In one embodiment aptamers that bind to a complex of interest are used to deliver a molecule or molecules conjugated to the aptamers (conjugated aptamers) to a specific cell type or specific cell types. The molecule or molecules can be selected from the list containing siRNA, miRNA, morpholino, DNA plasmid, mRNA, antisense oligonucleotide, other oligonucleotide, other polynucleotide, small molecule, polypeptide, protein, protein fragment, antibody, antibody fragment, or chemotherapeutic.

More specifically, Treg cell-targeting aptamer-siRNA chimeras (AsiCs) were used to deliver siRNAs capable of knocking down Foxp3 mRNA in Tregs. The aptamer arm binds to the target complex on the Tregs and the aptamer is internalized into the cells and delivers the siRNA sequences. The siRNA sequence is processed by the cells and results in knock down of Foxp3 mRNA. See FIGS. 8A and 8B. Results showed that the chimeric aptamer treatment decreased Foxp3 mRNA.

The aptamers and molecule or molecules can be delivered to cells suspected to contain the complex of interest in many ways that are evident to one ordinarily skilled in the art. Preferred embodiments will accomplish delivery by applying the conjugated aptamers to the media of cells in cell, or tissue culture, or by injecting the aptamers into a biological sample, such as into the bloodstream of an organism (*Nat Biotechnol. 2009 September; 27(9):839-49).

Additional examples of aptamers linked to therapeutic moieties can be prepared by linking aptamers to the molecules identified in Table 11. Tables 12 and 13 describe additional genes that can be targeted.

TABLE 11

Methods of molecule delivery using aptamers

| Target | Delivered molecule | Journal article describing method |
|---|---|---|
| HIV-infected CD4+ T cells | HIV gp120 siRNA | *Adv Exp Med Biol. 2015; 848: 211-34 |
| PSMA-positive mouse prostate tumors | Plk1 siRNA | *Nat Biotechnol. 2009 Sep; 27(9): 839-49 |
| PSMA-positive tumors | Gelonin Toxin | *Cancer Res. 2006 Jun 15; 66(12): 5989-92 |
| Matrix metalloproteinase 2 | Fluorescent Nanoprobe | *Nanoscale Res Lett. 2014; 9(1): 104 |

TABLE 12

List of Cluster of Differentiation (CD) molecule genes

| | | | | | | | |
|---|---|---|---|---|---|---|---|
| ABCB1 | CD200 | CD81 | F11R | IL10RA | KIR2DS2 | NCR2 | SLC4A1 |
| ABCG2 | CD207 | CD82 | F3 | IL10RB | KIR2DS4 | NCR3 | SLC7A5 |
| ACE | CD209 | CD83 | FAS | IL12RB1 | KIR2DS5 | NGFR | SPN |
| ACKR1 | CD22 | CD84 | FASLG | IL13RA1 | KIR3DL1 | NRP1 | TEK |
| ADAM10 | CD226 | CD86 | FCAMR | IL13RA2 | KIR3DL2 | NT5E | TFRC |
| ADAM17 | CD24 | CD8A | FCAR | IL15RA | KIR3DL3 | PDCD1 | THBD |
| ADAM8 | CD244 | CD8B | FCER2 | IL17RA | KIR3DP1 | PDCD1LG2 | THY1 |
| ADGRE2 | CD247 | CD9 | FCGR1A | IL18R1 | KIT | PDGFRA | TLR1 |
| ADGRE5 | CD248 | CD93 | FCGR2A | IL18RAP | KLRB1 | PDGFRB | TLR10 |

TABLE 12-continued

List of Cluster of Differentiation (CD) molecule genes

| | | | | | | | |
|---|---|---|---|---|---|---|---|
| ALCAM | CD27 | CD96 | FCGR2B | IL1R1 | KLRC1 | PECAM1 | TLR2 |
| ALK | CD274 | CD99 | FCGR2C | IL1R2 | KLRC2 | PI16 | TLR3 |
| ANPEP | CD276 | CDCP1 | FCGR3A | IL21R | KLRD1 | PLAUR | TLR4 |
| ART1 | CD28 | CDH1 | FCGR3B | IL2RA | KLRK1 | PLXNC1 | TLR6 |
| ART4 | CD300A | CDH2 | FCRL1 | IL2RB | L1CAM | PRNP | TLR8 |
| ATP1B3 | CD300C | CDH5 | FCRL2 | IL2RG | LAG3 | PROCR | TLR9 |
| B3GAT1 | CD300E | CEACAM1 | FCRL3 | IL3RA | LAIR1 | PROM1 | TNFRSF10A |
| BCAM | CD302 | CEACAM3 | FCRL4 | IL4R | LAIR2 | PSG1 | TNFRSF10B |
| BMPR1A | CD320 | CEACAM5 | FCRL5 | IL5RA | LAMP1 | PTGDR2 | TNFRSF10C |
| BMPR1B | CD33 | CEACAM6 | FGFR1 | IL6R | LAMP2 | PTGFRN | TNFRSF10D |
| BSG | CD34 | CEACAM8 | FGFR2 | IL6ST | LAMP3 | PTPRC | TNFRSF11A |
| BST1 | CD36 | CLEC10A | FGFR3 | IL7R | LEPR | PTPRJ | TNFRSF12A |
| BST2 | CD37 | CLEC4A | FGFR4 | IL9R | LIF'R | PVR | TNFRSF13B |
| BTLA | CD38 | CLEC4C | FLT3 | INSR | LILRA1 | NECTIN1 | TNFRSF13C |
| BTN3A1 | CD3D | CLEC4D | FUT3 | ITGA1 | LILRA2 | NECTIN2 | TNFRSF14 |
| C5AR1 | CD3E | CLEC4M | FUT4 | ITGA2 | LILRA3 | NECTIN3 | TNFRSF17 |
| CCR1 | CD3G | CLEC7A | FZD10 | ITGA2B | LILRA4 | RHAG | TNFRSF18 |
| CCR2 | CD4 | CLEC9A | FZD4 | ITGA3 | LILRA5 | RHCE | TNFRSF1A |
| CCR3 | CD40 | CR1 | FZD9 | ITGA4 | LILRA6 | RHD | TNFRSF1B |
| CCR4 | CD40LG | CR2 | GGT1 | ITGA5 | LILRB1 | S1PR1 | TNFRSF21 |
| CCR5 | CD44 | CRTAM | GP1BA | ITGA6 | LILRB2 | SDC1 | TNFRSF4 |
| CCR6 | CD46 | CSF1R | GP1BB | ITGAD | LILRB3 | SDC2 | TNFRSF8 |
| CCR7 | CD47 | CSF2RA | GP5 | ITGAE | LILRB4 | SELE | TNFRSF9 |
| CCR8 | CD48 | CSF2RB | GP9 | ITGAL | LILRB5 | SELL | TNFSF10 |
| CCR9 | CD5 | CSF3R | GYPA | ITGAM | LILRP1 | SELP | TNFSF11 |
| CD101 | CD52 | CTLA4 | GYPB | ITGAV | LILRP2 | SELPLG | TNFSF13 |
| CD109 | CD53 | CXCR1 | GYPC | ITGAX | LRP1 | SEMA4D | TNFSF13B |
| CD14 | CD55 | CXCR2 | HAVCR1 | ITGB1 | LY75 | SEMA7A | TNFSF14 |
| CD151 | CD58 | CXCR3 | HMMR | ITGB2 | LY9 | SIGLEC1 | TNFSF4 |
| CD160 | CD59 | CXCR4 | ICAM1 | ITGB3 | MCAM | SIGLEC5 | TNFSF8 |
| CD163 | CD6 | CXCR5 | ICAM2 | ITGB4 | MELTF | SIGLEC6 | TREM1 |
| CD164 | CD63 | CXCR6 | ICAM3 | JAG1 | MME | SIGLEC7 | TSPAN7 |
| CD177 | CD68 | DDR1 | ICAM4 | JAM2 | MPL | SIGLEC9 | VCAM1 |
| CD180 | CD69 | DPP4 | ICOS | KDR | MRC1 | SIRPA | VPREB1 |
| CD19 | CD7 | ENG | ICOSLG | KEL | MRC2 | SIRPB1 | CLEC12A |
| CD1A | CD70 | ENPEP | IFITM1 | KIR2DL1 | MS4A1 | SIRPG | GARP |
| CD1B | CD72 | ENPP3 | IFNGR1 | KIR2DL2 | MSR1 | SLAMF1 | |
| CD1C | CD74 | ENTPD1 | IGF1R | KIR2DL3 | MST1R | SLAMF6 | |
| CD1D | CD79A | EPCAM | IGF2R | KIR2DL4 | MUC1 | SLAMF7 | |
| CD1E | CD79B | ERBB2 | IGLL1 | KIR2DL5A | NCAM1 | SLAMF8 | |
| CD2 | CD80 | EVI2B | IGSF8 | KIR2DS1 | NCR1 | SLC44A1 | |

TABLE 13

List of Interleukin receptor genes

CXCR1
CXCR2
IL10RA
IL10RB
IL11RA
IL12RB1
IL12RB2
IL13RA1
IL13RA2
IL15RA
IL17RA
IL17RB
IL17RC
IL17RD
IL17RE
IL18R1
IL18RAP
IL1R1
IL1R2
IL1RAP
IL1RAPL1
IL1RAPL2
IL1RL1
IL1RL2
IL1RN
IL20RA
IL20RB
IL21R
IL22RA1

TABLE 13-continued

List of Interleukin receptor genes

IL22RA2
IL27RA
IL2RA
IL2RB
IL2RG
IL31RA
IL3RA
IL4R
IL5RA
IL6R
IL6ST
IL7R
IL9R

TABLE 14

List of Interleukin genes

IL10
IL11
IL12A
IL12B
IL13
IL15
IL16
IL17A
IL17B

TABLE 14-continued

List of Interleukin genes

IL17C
IL17D
IL17F
IL18
IL19
IL1A
IL1B
IL1F10
IL1RN
IL2
IL20
IL21
IL22
IL23A
IL24
IL25
IL26
IL27
IL3
IL31
IL32
IL33
IL34
IL36A
IL36B
IL36G
IL36RN
IL37
IL4
IL5
IL6
IL7
CXCL8
IL9

TABLE 15

List of immune cell types

| B Cells | innate lymphoid cells (ILCs) | macrophages | platelets | thymocytes | eosinophils |
|---|---|---|---|---|---|
| dendritic Cells | megakaryocytes | myeloid-derived suppressor cells (MDSC) | red blood cells (RBCs) | plasma cells | basophils |
| granulocytes | monocytes | natural killer (NK) cells | T cells | neutrophils | mast cells |

TABLE 16

List of T cell types

| regulatory T cells (Tregs) | gamma delta T cells | effector T cells | memory T cells |
|---|---|---|---|
| helper T cells (Th cells) | natural killer T cells (NKT cells) | cytotoxic T cells | mucosal associated invariant T cells |

Example 13

Identification of Aptamers

Using a system such as the SELEX system described herein to identify aptamers that specifically bind to complexes allows for the identification of conserved sequences within an aptamer pool. The conserved sequences can be used to generate additional aptamers that selectively bind to the desired complex.

Clusters of aptamers associated with each Treg aptamer were identified (see, Table 17 in FIG. 9A). Some Treg aptamers did not associate with clusters and are identified as "orphans." Other aptamers clustered with groups >30 sequences. Only the first 30 sequences were used for the alignment as 30 sequences is the maximum input for LocARNA.

Each cluster was aligned using LocARNA algorithm with a fixed structure predicted by RNAfold from the Vienna Package 2.0. The LocARNA alignment generated a consensus structure with sequence (see, Table 18 in FIG. 9B for the code legend), which was used to generate the alignment/consensus sequences for cluster. The consensus sequences are shown in FIGS. 10A, 10B and 10C.

The Vienna Package 2.0 (RNAfold) was used to generate the folding (Lorenz, Ronny and Bernhart, Stephan H. and Höner zu Siederdissen, Christian and Tafer, Hakim and Flamm, Christoph and Stadler, Peter F. and Hofacker, Ivo L. "ViennaRNA Package 2.0." Algorithms for Molecular Biology, 6:1 26, 2011, doi:10.1186/1748-7188-6-26).

The alignments were prepared using LocARNA (Sebastian Will, Tejal Joshi, Ivo L. Hofacker, Peter F. Stadler, and Rolf Backofen. "LocARNA-P: Accurate boundary prediction and improved detection of structural RNAs." RNA, 18 no. 5, pp. 900-14, 2012: Sebastian Will, Kristin Reiche, Ivo L. Hofacker, Peter F. Stadler, and Rolf Backofen. "Inferring non-coding RNA families and classes by means of genome-scale structure-based clustering." PLoS Computational Biology, 3 no. 4, pp. e65, 2007: Cameron Smith, Steffen Heyne, Andreas S. Richter, Sebastian Will, and Rolf Backofen "Freiburg RNA Tools: a web server integrating IntaRNA, ExpaRNA and LocARNA." Nucleic Acids Research, 38, Suppl pp. W373-7, 2010).

Example 14

Quantifying the Fraction of Receptors Occupied by Ligand Using Ligand-Receptor Complex-Binding Aptamers A novel cancer biomarker platform, designated as the "LIgand-REceptor Complex-binding APtamers" (LIRE-CAP) assay, was developed that determines the fraction of a given receptor occupied by ligand. This technology is based upon pairs of RNA aptamers with one aptamer binding preferentially to the unoccupied receptor and the other binding preferentially to the ligand-receptor complex. These two aptamers are added to a biospecimen, bound aptamers are expanded using RT-PCR, and the binding ratio assessed with colorimetric probes specific for each aptamer. The IL2-CD25 ligand-receptor complex was used as a model to develop and validate this assay. A similar approach could be applied to a broad range of molecular complexes that could serve as biomarkers in cancer. We conclude the LIRECAP assay approach has the potential to serve as a novel, high-throughput and inexpensive biomarker platform for cancer research and clinical care based on its ability to determine receptor occupancy by ligand.

Introduction

Multi-molecular complexes, including ligand-receptor complexes and receptor multimers, play a central role in mediating a broad range of processes in cancer biology and impact on cancer cell growth, differentiation and survival as well as the interaction between the cancer cell and its environment, including the immune response to cancer. One example is regulation of the immune response by the interaction between IL2 with its alpha receptor subunit, IL2Rβ (CD25) that leads to recruitment of additional receptor subunits (IL2Rβ and γ) to mediate activation signals in lymphocytes (1). Numerous studies have illustrated the importance of IL2-CD25 complexes on the immune response in a variety of diseases, including cancer (2-5). Agents that block such interactions have been explored as anti-tumor immune therapeutics (6). Measurement of either the receptors or the ligands involved in these interactions, e.g. IL2 or CD25, has been used as a measure of immune cell activation (1,7-12). In the IL2-CD25 system, as well as other systems involving ligand-receptor interactions, most assays probe separately for the labeled receptors or the ligands. Determining the fraction of receptors occupied by ligand using these assays is indirect and complex. The ability to quantify the fraction of receptors occupied by ligand, as opposed to assessing the concentration of ligand and receptor separately, could provide an additional and valuable tool for assessing whether receptors are occupied by ligand in a variety of biological specimens.

Nucleic acid aptamers are short oligonucleotides that recognize target antigens in a manner analogous to antibodies (13). The specificity of aptamers, including RNA aptamers, is based in large part on their nucleotide sequence, which determines the complementarity of their secondary and tertiary structures against their targets (14). Forces like those seen with antibody-antigen interactions, including van der Waals forces, hydrogen bonding and electrostatic interaction, can stabilize aptamer-target interactions. The affinity of RNA aptamers towards their targets can be similar to those of antibodies (15). RNA aptamers are most commonly generated by a process called SELEX (Systematic Evolution of Ligand by EXponential enrichment) that involves sequential enrichment of a diverse RNA library against a target (16, 17). Through this process, RNA aptamers that bind with high-affinity are selected (18). RNA aptamer selection is generally done using the native primary target and is not based on antigen processing and presentation (19). Thus, unique epitopes that would not be maintained during immunization, such as neo-epitopes formed due to molecular interactions, can be identified by aptamers, which gives them a potential advantage over antibodies. The nucleic acid nature of RNA aptamers allows them to be sequenced, synthesized, multiplied, modified and quantified easily. Although the short half-life of RNA aptamers in vivo can be a factor in their therapeutic utility, this does not impact on use of RNA aptamers as in vitro diagnostic agents.

This study describes a novel RNA aptamer-based assay platform designated as the "LIgand-REceptor Complex-binding APtamers" or "LIRECAP" assay that allows for quantification of the fraction of receptors occupied by ligand. While these studies have focused on the IL2-CD25 ligand-receptor model system, the LIRECAP platform could be applied to measure a broad range of multi-molecular complexes that could serve as biomarkers for cancer progression or response to therapy.

Results

Cell-Based SELEX Identified Human T Regulatory (Treg) Cell-Binding RNA Aptamers:

Treg cell-based SELEX approach was designed to identify RNA aptamers that bind to human Tregs (FIG. 1). The starting library consisted of RNA aptamers containing 20 random nucleotide sequence (N20) flanked by SEL 2 primer-binding regions. Freshly-obtained T cells from a different de-identified healthy donor were used for each round to ensure that the aptamers recognized antigens from across diverse subjects. Aptamers that bound non-specifically to T cells were precleared by removing those that bound to $CD4^+CD25^{neg}$ Teff cells, followed by positive selection with $CD4^+CD25^{high}$ Treg cells from the same donor. The selection conditions used for each round of SELEX is summarized in Supplementary Table S1.

The enrichment of the aptamer pool during SELEX was monitored using a DNA melt assay that relates to the sequence complexity of the aptamer pool (20). Sequential rounds of SELEX resulted in a rightward shift in the DNA melt curve indicating a decrease in library complexity and increased aptamer enrichment with advancing SELEX rounds.

The specificity of aptamer pools for Treg and Teff cells was assessed using a T-cell based binding assay. Aptamer pools from SELEX rounds 1, 4 and 7 were incubated with $CD4^+CD25^{high}$ Tregs and $CD4^+25^{neg}$ Teff cells from the same donor and aptamer binding was measured using SYBR green-based RT-qPCR. As illustrated in FIG. 2A, a significantly increased binding of aptamer pools to Tregs was seen in round 7 when compared to rounds 1 and 4 indicating enrichment of Treg-binding aptamers [p=0.002 (Rd 7 vs. Rd 1 or Rd 4]. These data indicate that the SELEX process enriched for RNA aptamers that bind preferentially to antigens expressed by Tregs relative to Teff cells.

High Throughput Sequencing and Aptamer Bioinformatics to Identify Candidate Treg Aptamers Illumina-based HTS platform was used to sequence aptamers from all rounds including the starting aptamer library (Round 0). HTS across the eight rounds of aptamer selection yielded 157.8 million reads representing 77.1 million different aptamer sequences with an average of 3.9 million unique aptamers identified in each SELEX round. A steady decline in the number of unique aptamer sequences indicative of enrichment of Treg-binding sequences (FIG. 2B) was seen with early rounds of selection (FIG. 2C). Enrichment of 60% was seen by round four with the degree of enrichment slowing at rounds five and six. A plateau was reached between rounds seven and eight (FIG. 2C). This HTS data on library diversity was consistent with data on Treg specificity observed in the T-cell RT-PCR-based binding suggesting more than eight rounds of enrichment were unlikely to have additional benefit.

Aptamers with the potential to be specific for Tregs were identified as those sequences that increased in abundance (50 reads) and persistence (found on at least 4 rounds) above the unselected library. 4,457 unique aptamer sequences represented by 3.5 million reads met these criteria.

To identify the most promising candidate aptamer sequences for validation, aptamer sequences were assessed for a steady increase in abundance across sequential rounds of selection. They were also clustered based on sequence similarity (edit distance) and structural similarity (tree distance) (20). Top aptamers were selected that demonstrated a stepwise increase in abundance over rounds of selection, and that were from different sequence and structure families. The final panel consisting of eleven candidates were synthesized for further evaluation. A control aptamer that was only observed in the unselected starting aptamer library (Round 0) and not in any other selection round was identified (C-248) to serve as a non-selected control aptamer.

Aptamer Specificity for Tregs and Teffs

Synthesized aptamers were tested for their ability to bind to Tregs and Teff cells. Aptamers were incubated with enriched primary human Tregs and Teff cells and bound aptamers were quantified using RT-qPCR. Data indicated that all selected aptamers bound in higher quantities to Tregs than to Teff cells (FIG. 3A). The negative control aptamer (C-248) did not bind to either T cell subset. These data confirmed all candidate aptamers bind more extensively to Tregs than to Teffs.

Identification of Aptamers that Recognize CD25:

Tregs used in the selection process were defined as $CD4^+$ cells expressing high surface levels of CD25 (21), thus the lead aptamers were assessed for binding to the CD25 protein. Five of the top eleven aptamers (Tr-1, Tr-6, Tr-7, Tr-8 and Tr-11) bound to recombinant human CD25-coated Dynabeads demonstrating their target antigen is CD25 (FIG. 3B).

Aptamers do not Interfere with Binding of IL2 to CD25 or IL2-Induced Signaling:

Since IL2 is the natural ligand for CD25, CD25-binding aptamers were assessed for their ability to interfere with the binding of IL2 to CD25. Using an ELISA-based assay, the $EC_{50}$ of IL2 binding to recombinant CD25 was assessed in the presence or absence of aptamers. As shown in FIG. 3C, none of the CD25-binding aptamers significantly altered the ability of IL2 to bind CD25 irrespective of the order of the addition of aptamers (prior to or after addition of IL2 to CD25). Similar results were found in a functional system exploring the impact of aptamer on Treg signaling mediated by IL2 as measured by tyrosine phosphorylation of STAT5 (12). Up to a 10-fold increase in phospho-STAT5 levels was observed 30 minutes after addition of IL2 as measured by flow cytometry. CD25-binding aptamers did not significantly alter the levels of phospho-STAT5 induced by IL2 in Tregs (FIG. 3D). Thus, the CD25-binding aptamers did not alter IL2 binding or signaling through CD25.

Aptamers Display Differential Preference for Unoccupied CD25 and IL2-CD25 Ligand-Receptor Complex:

Although the aptamers did not interfere with IL2 binding to CD25, IL2 did have an impact on the ability of some CD25-binding aptamers to recognize CD25. Pre-incubation of CD25-coated Dynabeads with IL2 resulted in significantly enhanced binding of some aptamers to CD25 (Tr-1 and Tr-7). In contrast, addition of IL2 significantly reduced binding of other aptamers to CD25 (Tr-6 and Tr-8) (FIG. 4A). Results obtained with a Treg cell-based system were similar. IL2 treatment of Tregs led to significantly higher binding of Tr-1 and Tr-7 and lower binding of Tr-6 and Tr-8 (FIG. 4B). Tr-11 showed similar binding to both receptor and ligand-receptor complex (FIGS. 4A and 4B). Thus, some aptamers bind preferentially to the IL2-CD25 ligand-receptor complex, while others bind preferentially to unoccupied CD25.

Figure 11A:
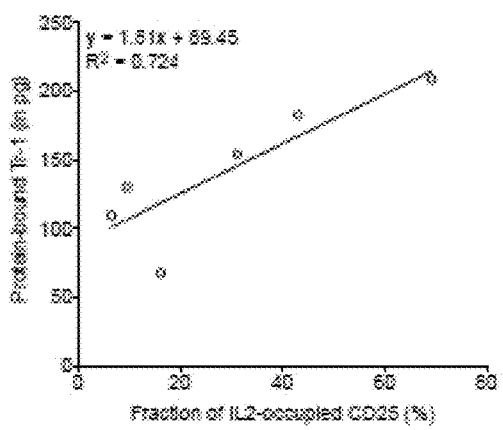
Figure 11B:
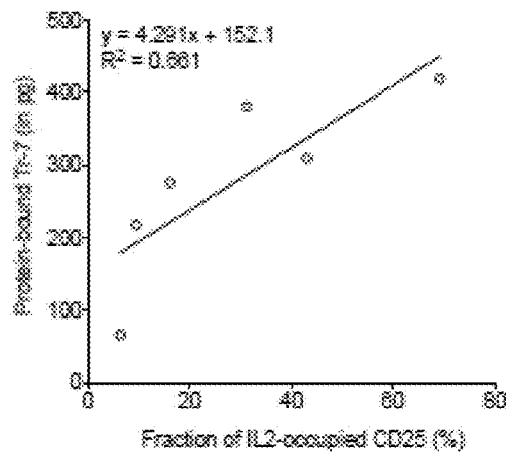
Figure 11C:
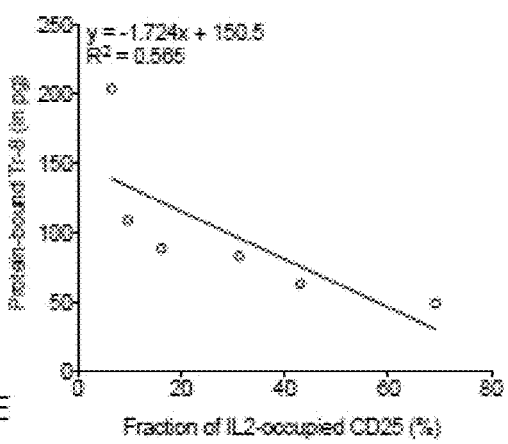
Figure 11D:
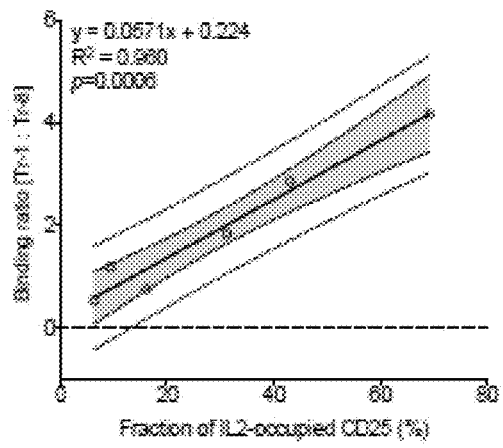
Figure 11E:
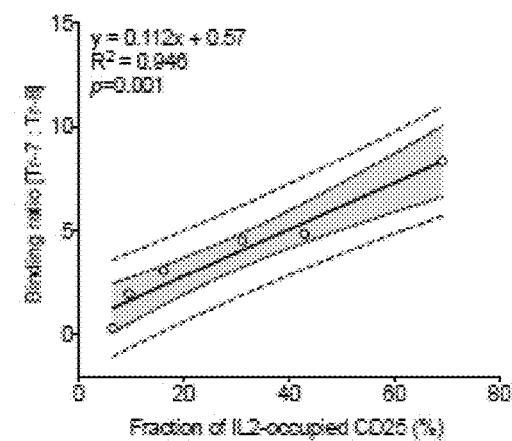

Aptamers with Differential Binding to the IL2-CD25 Complex and Unoccupied CD25 can be Used to Quantify the Fraction of CD25 Occupied by IL2:

If an aptamer with preference for the IL2-CD25 complex (e.g. Tr-1 or Tr-7) paired with an aptamer with preference for unoccupied CD25 (e.g. Tr-8) are added together to a biospecimen predominantly containing the IL2-CD25 complex, more of the aptamer that prefers the IL2-CD25 complex (Tr-1 or Tr-7) would be expected to bind. In contrast, if the same mixture is added to a biospecimen containing largely unoccupied CD25, more of the aptamer that prefers the unoccupied receptor (e.g. Tr-8) should bind. Furthermore, neither aptamer significantly alters IL2 binding to CD25. The use of two different aptamers that can be amplified by same primer set, and evaluation of their binding ratio, provides a robust internal control. These characteristics form the basis for the LIRECAP assay concept that should allow for the measurement of the fraction of receptor (in this case CD25) occupied by ligand (in this case IL2) in a sample. To test this concept, samples with different levels of IL2 occupation of CD25 were created by incubating CD25-coated Dynabeads with various concentrations of IL2. The fraction of CD25 occupied by IL2 was confirmed using an IL2-specific ELISA based on determination of the initial levels of CD25 and IL2 added during the complex formation and the free IL2 detected after incubation (22). Equimolar concentrations of one complex-preferring aptamer (e.g. Tr-1 or Tr-7) and an unoccupied receptor-preferring aptamer (e.g. Tr-8) were added to the samples. Binding of the two distinct aptamers to the protein-coated beads was quantified using TaqMan-based RT-qPCR with fluorochrome-labeled probes specific for the variable regions of each aptamers (Supplementary Table S4). As shown in FIGS. 11A and 11B, binding levels of Tr-1 ($R^2=0.724$) and Tr-7 ($R^2=0.661$) correlated with increasing levels of IL2-occupied CD25. Conversely, Tr-8 displayed an inverse correlation with increasing levels of IL2-occupied CD25 ($R^2=0.565$; FIG. 11C). The ratio of bound Tr-1 or Tr-7 to bound Tr-8 was determined at each receptor occupancy level to create regression curves illustrating receptor occupancy. There was a strong linear relationship [$R^2=0.960$; p=0.0006 (Tr-1:Tr-8) and $R^2=0.946$; p=0.001 (Tr-7:Tr-8)] between aptamer binding ratios when plotted against the fraction of CD25 occupied by IL2 (FIGS. 11D and 11E).

Application of the LIRECAP Assay to Measurement of Soluble Ligand-Receptor Complex in Human Serum:

Similar studies were done in human serum samples containing a range of IL2 occupancies of CD25 created by spiking the serum with recombinant CD25 and various concentrations of IL2. Tr-7 aptamer showed a positive correlation ($R^2=0.609$; FIG. 12A), whereas, Tr-8 showed a negative correlation ($R^2=0.859$; FIG. 12B) with increasing ligand-receptor complex levels. The ratio of bound aptamers (Tr-7:Tr-8) displayed a strong linear relationship with the fraction of IL2-occupied CD25 ($R^2=0.946$; p=0.005; FIG. 12C).

A scheme of LIRECAP assay that provides the ability to measure the ligand occupancy of soluble receptors, such as IL2RA, growth hormone receptors and other cytokine receptors, is provided in FIG. 13.

In certain embodiments, the aptamers detect PD-1 and PD-L1 complexes, or PD-1 and PD-L2 complexes. This allows for prediction of whether monoclonal antibodies directed against these molecules are likely to have a beneficial therapeutic effect in patients with cancer and other disorders.

Discussion

Immunologic, diagnostic and pharmacologic agents, including radiolabeled ligands, monoclonal antibodies, small molecules and RNA aptamers, are used to study receptors and ligands in a broad range of scientific, diagnostic and therapeutic applications in cancer and beyond. Technologies, such as mass spectrometry, FRET, BIAcore, etc., are used to assess ligand-receptor interactions, kinetics and biology (23,24). In general, such technologies rely on recognition of either the receptor or the ligand. Each of these technologies has an important role in cancer research, yet each has its limitations, such as lack of specificity, complexity and cost. This limits their value when it comes to their high-throughput use as biomarkers. Here, we describe a novel technology platform, designated LIRECAP, for determining the fraction of receptors occupied by a given ligand that has the potential to be high throughput and could have unique applicability in cancer research and eventually cancer care.

The studies described here used a whole cell SELEX approach to identify Treg-specific aptamers. It was not the initial intent of these studies to develop an assay for quantifying ligand-receptor complexes. However, given the use of normal donor PBMCs as targets, it is not surprising in retrospect that some of the CD25 molecules expressed by the Tregs used in the selection process were occupied by IL2 while other CD25 molecules were unoccupied. This led to selection of some RNA aptamers that preferentially bind to complexes and some to unoccupied receptor. Once it was determined that RNA aptamers had been identified that bind to the same target but have binding that is differentially influenced by the presence of ligand, it occurred to us that such ligand-receptor complex aptamers could be used for precise quantification of the fraction of receptors occupied by ligand.

The LIRECAP assay described here involves an aptamer pair, one that binds preferentially to the complex and the second that binds preferentially to unoccupied receptor, and adding them together to the sample to be tested. When the receptor is not occupied by ligand, there will be greater binding of the aptamer that preferentially binds to the unoccupied receptor. When ligand-receptor complex is present, there will be a greater binding of the aptamer that preferentially binds to the complex. Importantly, the aptamers do not alter ligand binding to receptor. Aptamer binding can thus be determined using a known set of samples with varying receptor occupancy levels to develop a standard curve. A standard correlation curve generated by plotting the ratio of the aptamers that preferentially bind to ligand-receptor complexes over those that preferentially bind to unoccupied receptor can be used to determine the receptor occupancy in unknown samples. Initial proof of concept studies indicate that this assay can also be performed on human biospecimens, such as human serum samples containing soluble ligand-receptor complexes.

SELEX is based on an aptamer library that includes aptamers of the same length (51 bases in this case), and with the same primers at both ends. This allows for relatively uniform expansion of aptamer pools by RT-PCR. This is important for the application of aptamer technology outlined here. The aptamers that bind preferentially to unoccupied receptors and the aptamers that bind preferentially to complexes are of the same length and can be expanded using the same primers. Expansion should therefore be proportional. Quantification of PCR products following expansion with single set of primers is done using two distinct TaqMan probes specific for the central variable regions of the aptamers. Standard curves where a known concentration of ligand is added to the receptors then allows for quantification of the ratio of ligand-receptor complex to unbound receptor.

The preference of aptamers for unoccupied receptor or complex does not need to be complete as it would for a monoclonal antibody designed to distinguish between the two. Adjustment for background binding results from using two aptamers and a standard curve so the ratio allows for quantitation of the percent of receptor occupied by ligand.

On-going studies are exploring this technology as a way to quantify the fraction of receptors occupied by ligand in clinical biospecimens obtained from patients with cancer and other immune-related diseases. The studies reported here were conducted using recombinant CD25 and IL2 as a model, however a similar approach could be applied to other ligand-receptor systems that may be relevant in cancer biology and cancer therapy. It could be used to quantify the percent of ligand occupied by receptor in soluble fluids, as shown with human serum, cells or tissues. With further refinement, this approach could even be used to visualize receptor occupancy using in situ PCR. It also could be used to assess molecular complexes beyond cytokine-receptor interactions. For example, this technology could be applied to determine the percent of PD-1 molecules occupied by PDL1 or PDL2, or to differentiate receptor homodimers from heterodimers. Using a modification of the SELEX system reported here and with purified receptors and ligands, we are currently working to identify such pairs of aptamers for a variety of different multimolecular complexes.

In summary, this report describes a novel assay platform, designated the LIRECAP assay, which quantifies the fraction of receptors occupied by ligand. The LIRECAP assay is based on pairs of RNA aptamers that bind differentially based on the presence or absence of ligand. Tregs and the IL2-CD25 complex was used as the model for these proof-of-principle studies, however, a similar approach could be applied to a broad variety of molecular complexes with the potential to serve as biomarkers in cancer. A robust comparison of the approach described here to standard approaches to assessing ligand-receptor complexes is needed before the true value of this new approach can be determined. Nevertheless, the LIRECAP assay has the potential to be of considerable scientific and clinical diagnostic use in the study of how ligand-receptor complexes and other multi-molecular complexes impact on cancer biology with the long-term goal of serving as a new class of clinically-valuable biomarkers.

Example 14

References

1. Waldmann T A. The biology of interleukin-2 and interleukin-15: implications for cancer therapy and vaccine design. Nat Rev Immunol 2006; 6(8):595-601 doi 10.1038/nri1901.
2. Ito M, Zhao N, Zeng Z, Zhou X, Chang C C, Zu Y. Interleukin-2 Functions in Anaplastic Large Cell Lymphoma Cells through Augmentation of Extracellular Signal-Regulated Kinases 1/2 Activation. Int J Biomed Sci 2011; 7(3):181-90.
3. Malek T R, Castro I. Interleukin-2 receptor signaling: at the interface between tolerance and immunity. Immunity 2010; 33(2):153-65 doi 10.1016/j.immuni.2010.08.004.
4. Peggs K S, Quezada S A, Chambers C A, Korman A J, Allison J P. Blockade of CTLA-4 on both effector and regulatory T cell compartments contributes to the antitumor activity of anti-CTLA-4 antibodies. J Exp Med 2009; 206(8):1717-25 doi 10.1084/jem.20082492.

5. Whiteside T L, Schuler P, Schilling B. Induced and natural regulatory T cells in human cancer. Expert Opin Biol Ther 2012; 12(10):1383-97 doi 10.1517/14712598.2012.707184.
6. Melero I, Berman D M, Aznar M A, Korman A J, Perez Gracia J L, Haanen J. Evolving synergistic combinations of targeted immunotherapies to combat cancer. Nat Rev Cancer 2015; 15(8):457-72 doi 10.1038/nrc3973.
7. Goyonlo V M E H, Nordlind K. Interleukin-2 expression in lupoid and usual types of old world cutaneous leishmaniasis. Iran Red Crescent Med J 2014; 16(11):5410.
8. Jones D, Ibrahim S, Patel K, Luthra R, Duvic M, Medeiros L J. Degree of CD25 expression in T-cell lymphoma is dependent on tissue site: implications for targeted therapy. Clin Cancer Res 2004; 10(16):5587-94 doi 10.1158/1078-0432.CCR-0721-03.
9. Kasprzak A, Spachacz R, Wachowiak J, Stefanska K, Kaczmarek E, Zabel M. Tissue expression of interleukin 2 (IL-2) and IL-2 receptor (IL-2R(alpha)/CD25) in non-Hodgkin B-cell lymphomas in children: correlations with clinical data. J Pediatr Hematol Oncol 2010; 32(6):462-71 doi 10.1097/MPH.0b013e3181e33f9c.
10. Miyamoto C, Mattos Neto R B, Cesare S D, Belfort Junior R, Burnier M N, Jr. Use of CD25 as an immunohistochemical marker for acquired ocular toxoplasmosis. Arq Bras Oftalmol 2010; 73(5):443-6.
11. Wargo J A R S, Reuben A, Sharma P. Monitoring immune responses in the tumor microenvironment. Curr Opin Immunol 2016; 41:23-31.
12. Yang Z Z, Grote D M, Ziesmer S C, Manske M K, Witzig T E, Novak A J, et al. Soluble IL-2Ralpha facilitates IL-2-mediated immune responses and predicts reduced survival in follicular B-cell non-Hodgkin lymphoma. Blood 2011; 118(10):2809-20 doi 10.1182/blood-2011-03-340885.
13. Ma H, Liu J, Ali M M, Mahmood M A, Labanieh L, Lu M, et al. Nucleic acid aptamers in cancer research, diagnosis and therapy. Chem Soc Rev 2015; 44(5):1240-56 doi 10.1039/c4cs00357h.
14. Zhou J, Rossi J. Aptamers as targeted therapeutics: current potential and challenges. Nat Rev Drug Discov 2017; 16(6):440 doi 10.1038/nrd.2017.86.
15. Sun H Z, Y. A Highlight of Recent Advances in Aptamer Technology and Its Application. Molecules 2015; 20(7): 11959-80.
16. Ellington A D, Szostak J W. In vitro selection of RNA molecules that bind specific ligands. Nature 1990; 346 (6287):818-22 doi 10.1038/346818a0.
17. Tuerk C, Gold L. Systematic evolution of ligands by exponential enrichment: RNA ligands to bacteriophage T4 DNA polymerase. Science 1990; 249(4968):505-10.
18. Stoltenburg R, Reinemann C, Strehlitz B. SELEX—a (r)evolutionary method to generate high-affinity nucleic acid ligands. Biomol Eng 2007; 24(4):381-403 doi 10.1016/j.bioeng.2007.06.001.
19. Keefe A D, Pai S, Ellington A. Aptamers as therapeutics. Nat Rev Drug Discov 2010; 9(7):537-50 doi 10.1038/nrd3141.
20. Thiel W H, Bair T, Peek A S, Liu X, Dassie J, Stockdale K R, et al. Rapid identification of cell-specific, internalizing RNA aptamers with bioinformatics analyses of a cell-based aptamer selection. PLoS One 2012; 7(9): e43836 doi 10.1371/journal.pone.0043836.
21. Yu N, Li X, Song W, Li D, Yu D, Zeng X, et al. CD4(+)CD25 (+)CD127 (low/−) T cells: a more specific Treg population in human peripheral blood. Inflammation 2012; 35(6):1773-80 doi 10.1007/s10753-012-9496-8.
22. Friguet B, Chaffotte A F, Djavadi-Ohaniance L, Goldberg M E. Measurements of the true affinity constant in solution of antigen-antibody complexes by enzyme-linked immunosorbent assay. J Immunol Methods 1985; 77(2):305-19.
23. Abu-Farha M, Elisma F, Figeys D. Identification of protein-protein interactions by mass spectrometry coupled techniques. Adv Biochem Eng Biotechnol 2008; 110:67-80 doi 10.1007/10_2007_091.
24. Stoddart L A, White C W, Nguyen K, Hill S J, Pfleger K D. Fluorescence- and bioluminescence-based approaches to study GPCR ligand binding. Br J Pharmacol 2016; 173(20):3028-37 doi 10.1111/bph.13316.
25. Thiel W H, Esposito C L, Dickey D D, Dassie J P, Long M E, Adam J, et al. Smooth Muscle Cell-targeted RNA Aptamer Inhibits Neointimal Formation. Mol Ther 2016; 24(4):779-87 doi 10.1038/mt.2015.235.
26. McNamara J O, 2nd, Andrechek E R, Wang Y, Viles K D, Rempel R E, Gilboa E, et al. Cell type-specific delivery of siRNAs with aptamer-siRNA chimeras. Nat Biotechnol 2006; 24(8):1005-15 doi 10.1038/nbt1223.

Example 15

LIRECAPs Display Preferential Binding to Unoccupied Vs. IL2-Bound CD25

Molecular complexes, including ligand-receptor complexes, are central to the regulation of a broad range of cellular processes. While existing reagents can be used to study receptors as individual entities, they do not differentiate or quantify unoccupied receptors from ligand-bound receptors. The ability to quantify, simply and directly, the fraction of the receptor in a biological sample occupied by its ligand could give valuable information on ligand-receptor interactions and could lead to identification of multimolecular complexes that are difficult with existing techniques.

RNA aptamers are short oligonucleotides that, similar to antibodies, bind to target antigens. Here, using a T regulatory (Treg) cell-based selection strategy (SELEX), we developed a panel of RNA aptamers that recognize human Interleukin 2 receptor alpha (IL2RA or CD25) protein. The unique aspect of this aptamer set is that some of the aptamers show preferential binding towards the unoccupied IL2RA, while others in the panel show preferential binding towards IL2-occupied IL2RA.

Utilizing their differential binding property, we developed a novel assay that can allow for quantification of IL2-bound IL2RA fractions in biological specimens. Our data shows that the binding of LIRECAP (LIgand-Receptor Complex-binding APtamers), consisting of an aptamer preferring unoccupied IL2RA and an aptamer preferring IL2-occupied IL2RA, is linearly correlated to the fraction of IL2-occupied IL2RA in a given sample and can be used to quantify ligand—the fraction receptors occupied by ligand. The LIRECAP technology can potentially be used to quantify other multimolecular complexes involved in cancer and other diseases.

Treg Cell-Based SELEX of LIRECAPs.

Eight rounds of SELEX (each round was done with T cells from a different normal donor). FIG. 14. Bioinformatic analysis and screening of top candidates was performed, identifying Treg-binding aptamers.

A subset of Treg-binding aptamers recognize human IL2RA. Top RNA aptamers selected by Treg cell SELEX were tested for binding to IL2RA. Recombinant human IL2RA-coated Dynabeads were incubated with RNA aptamers. After extensive washing, bound aptamers were extracted and quantified by RTqPCR. Five RNA aptamers (Tr-1, Tr-6, Tr-7, Tr-8 and Tr-11) bound to IL2RA. FIG. 15.

IL2RA-binding aptamers show differential binding to unoccupied vs IL2-occupied IL2RA IL2RA-binding aptamers were examined for their binding to unoccupied IL2RA vs IL2-occupied IL2RA. Binding of the aptamers to proteins was quantified by RT-qPCR. Some IL2RA-binding aptamers preferentially recognized the unoccupied IL2RA (Tr-6 and Tr-8); while others preferentially recognized IL2-occupied IL2RA (Tr-1 and Tr-7). Tr-11 bound similarly to both unoccupied and IL2-occupied receptors. FIG. 16.

A panel of RNA aptamers (LIRECAPs) recognizing human IL2RA were identified by Treg cell-based SELEX. These aptamers show differential preference in binding to IL2RA occupied with IL2 (Tr-1 and Tr-7) versus unoccupied IL2RA (Tr-6 and Tr-8). A novel LIRECAP-based receptor occupancy assay was designed using these aptamers to quantify the percentage of IL2RA occupied by IL2. LIRECAP technology can be used to evaluate the fraction of a receptor occupied by ligand.

Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

---

What is claimed is:

1. A composition comprising an aptamer bound to a complex, wherein the complex comprises at least two polypeptides, wherein the at least two polypeptides are IL2 and CD25.

2. The composition according to claim 1, wherein the aptamer specifically binds to the complex.

3. The composition according to claim 1, wherein the aptamer bound to the complex additionally comprises a tag.

4. The composition according to claim 3, wherein the tag is selected from a molecule that can be detected using optical sensors, molecular size sensors, or isotopic sensors.

5. The composition according to claim 1, wherein the aptamer is additionally bound to a substrate.

6. The composition according to claim 1, wherein the aptamer additionally comprises a therapeutic moiety.

7. The composition according to claim 6, wherein the therapeutic moiety is selected from nucleic acid based therapeutics, chemotherapeutics, immunotherapeutics, and small molecule therapeutics.

8. A cell comprising the aptamer bound to the complex according to claim 1.

9. A method of quantifying a fraction of CD25 occupied by IL2 in a sample, the method comprising:
   contacting the sample with a first aptamer that specifically binds to an IL2-CD25 complex;
   contacting the sample with a second aptamer that specifically binds to unoccupied CD25; and
   determining the amount of bound first aptamer and second aptamer.

10. The method according to claim 9, wherein the contacting of the sample with the first aptamer and the second aptamer is done simultaneously.

11. The method according to claim 9, wherein the first aptamer and the second aptamer additionally comprise tags.

12. The method according to claim 11, wherein the tag on the first aptamer is distinct from the tag on the second aptamer.

13. A method of isolating the cell according to claim 8, comprising:
   providing a sample comprising the cell;
   contacting the cell with a substrate that binds to the aptamer; and
   separating the cell bound to the substrate from the sample.

14. A method of isolating a complex, comprising:
   providing an aptamer, wherein the aptamer is capable of binding to a complex comprising at least a first polypeptide and a second polypeptide, wherein the first polypeptide is IL2 and the second polypeptide is CD25;
   contacting the aptamer with a sample comprising the at least first polypeptide and second polypeptide to form a bound complex; and
   isolating the bound complex from the sample.

15. The method according to claim 14, wherein the aptamer is attached to a substrate.

16. The method according to claim 14, wherein the at least first polypeptide and second polypeptide are located on the surface of a cell and the cell is isolated from the sample.

17. A method of treating a disease in a mammal, comprising:
   contacting the mammal with the aptamer according to claim 6.

* * * * *